(12) United States Patent
Modlin et al.

(10) Patent No.: US 6,503,719 B2
(45) Date of Patent: Jan. 7, 2003

(54) METHODS AND APPARATUS FOR DETECTING POLYNUCLEOTIDE HYBRIDIZATION

(75) Inventors: Douglas N. Modlin, Palo Alto; Todd E. French, Cupertino; Jon F. Petersen, Redwood City; John C. Owicki, Palo Alto, all of CA (US)

(73) Assignee: LJL BioSystems, Inc., Sunnyvale, CA (US)

(*) Notice: Subject to any disclaimer, the term of this patent is extended or adjusted under 35 U.S.C. 154(b) by 40 days.

(21) Appl. No.: 09/767,316

(22) Filed: Jan. 22, 2001

(65) Prior Publication Data

US 2001/0034025 A1 Oct. 25, 2001

Related U.S. Application Data

(63) Continuation of application No. PCT/US00/00895, filed on Jan. 14, 2000.
(60) Provisional application No. 60/116,113, filed on Jan. 15, 1999, provisional application No. 60/135,284, filed on May 21, 1999, and provisional application No. 60/167,463, filed on Nov. 24, 1999.

(51) Int. Cl.$^7$ .......................... C12Q 1/68; C12P 19/34; C07H 21/02; C07H 21/04
(52) U.S. Cl. .................. 435/6; 435/91.2; 536/23.1; 536/24.3
(58) Field of Search ................... 435/6, 91.2; 536/23.1, 536/24.3

(56) References Cited

U.S. PATENT DOCUMENTS

| | | | |
|---|---|---|---|
| 5,593,867 A | 1/1997 | Walker et al. | 435/91.2 |
| 5,786,139 A | 7/1998 | Burke et al. | 435/6 |
| 5,849,547 A | 12/1998 | Cleuziat et al. | 435/91.21 |
| 5,858,671 A | 1/1999 | Jones | 435/6 |
| 5,981,185 A | 11/1999 | Matson | 435/6 |
| 6,045,996 A | 4/2000 | Cronin | 435/6 |
| 6,297,018 B1 * | 10/2001 | French et al. | 435/6 |

OTHER PUBLICATIONS

*Fixed Polarizer Ellipsometry for Simple and Sensitive Detection of Thin Films Generated by Specific Molecular Interactions: applications in immunoassays and DNA sequence detection*, Ostroff et al., Clinical Chemistry, 44:9, pp. 2031–2035, 1998.
*Processing of cDNA and Genomic Kilobase–Size Clones for Massive Screening, Mapping and Sequencing by Hybridization*. S. Drmanac et al. BiotechniQue, (1994), vol. 17, No. 2, 1988.
*Stratagene* 1988 Catalog excerpt, 1988.

* cited by examiner

Primary Examiner—W. Gary Jones
Assistant Examiner—Arun Charkrabarti
(74) Attorney, Agent, or Firm—Kolisch, Hartwell, Dickinson, McCormack & Heuser

(57) ABSTRACT

Methods and apparatus for detecting polynucleotide hybridization in luminescence-based assays. The methods may include (1) contacting a sample polynucleotide with a reference polynucleotide at an assay site, where at least one of the polynucleotides is capable of emitting luminescence, (2) illuminating the assay site with light capable of stimulating such luminescence, (3) detecting light transmitted from the assay site, and (4) deriving information relating to the extent of hybridization between the sample and reference polynucleotides based on the detected light. The methods may further include (1) illuminating with and/or detecting polarized light, (2) deriving information relating to the sequence of the sample polynucleotide from the extent of hybridization, and (3) converting the light to a signal and distinguishing between a portion of the signal attributable to luminescence and a portion attributable to background.

38 Claims, 20 Drawing Sheets

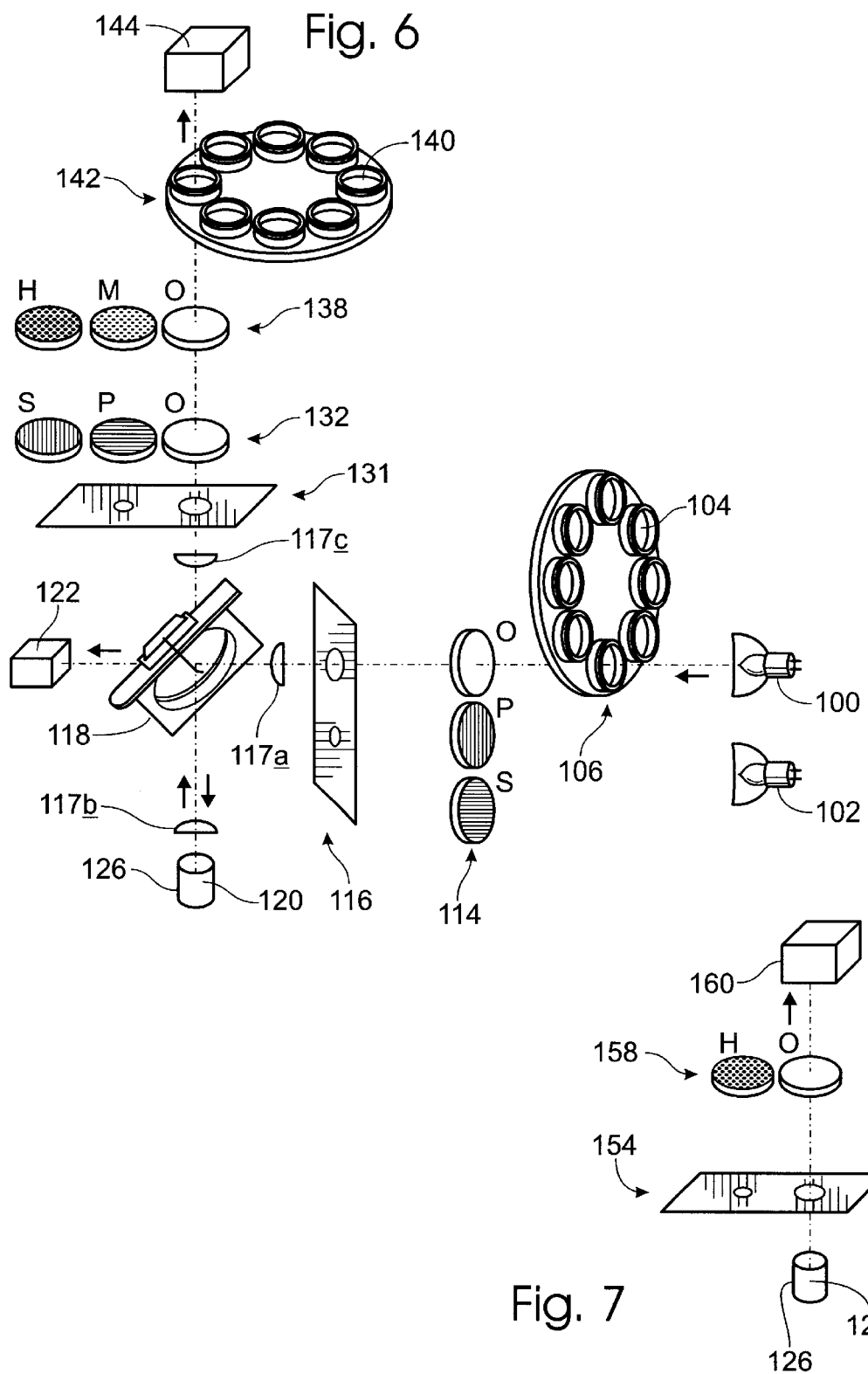

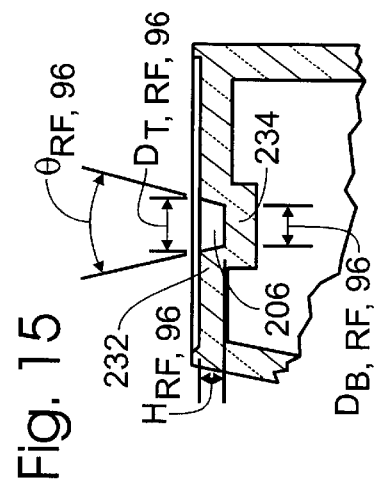
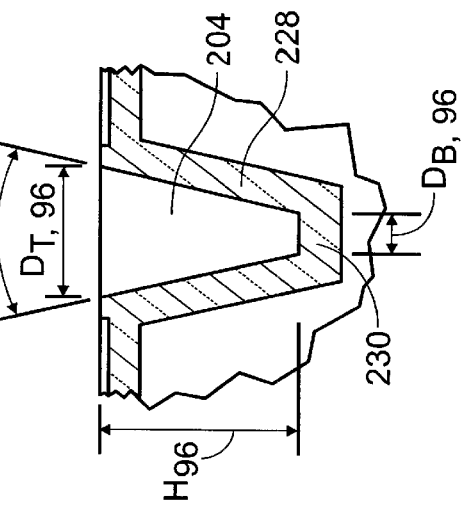
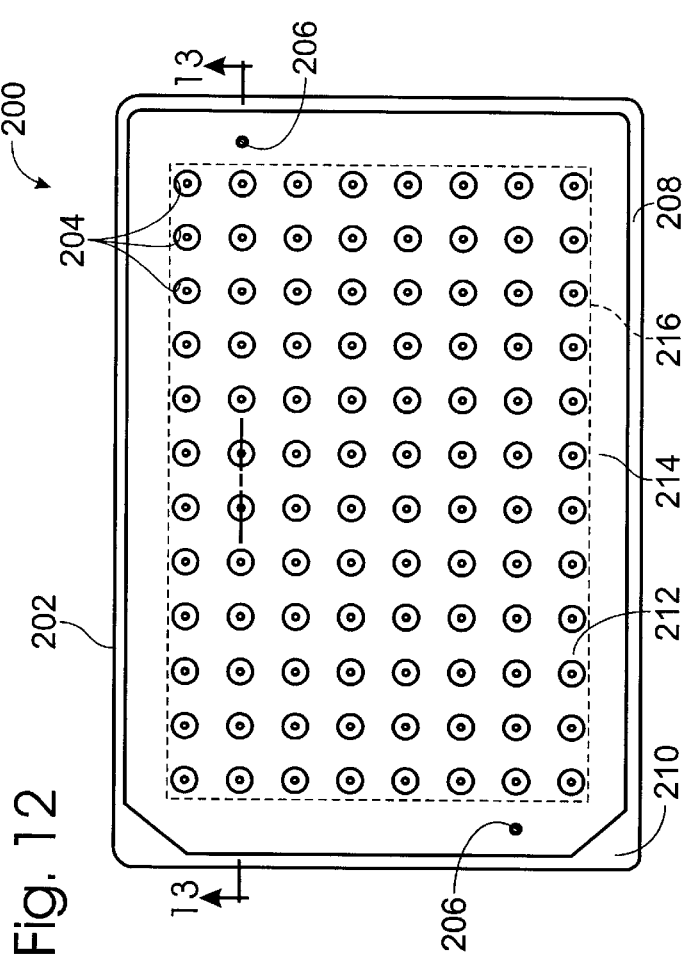
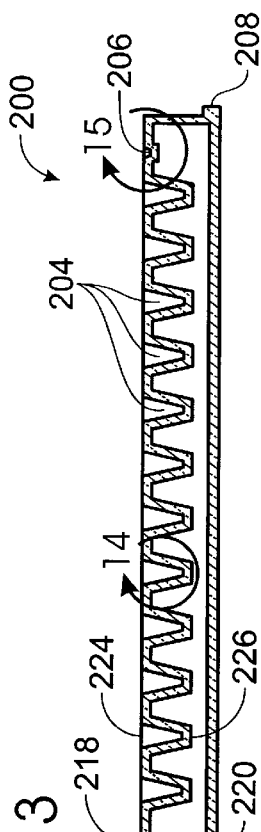

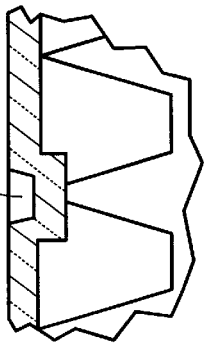
Fig. 19
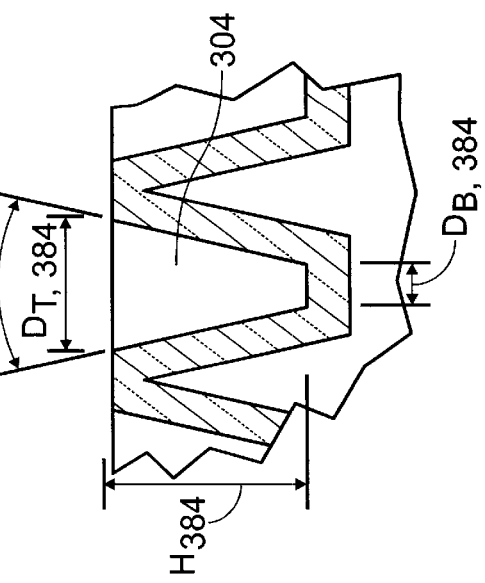
Fig. 18
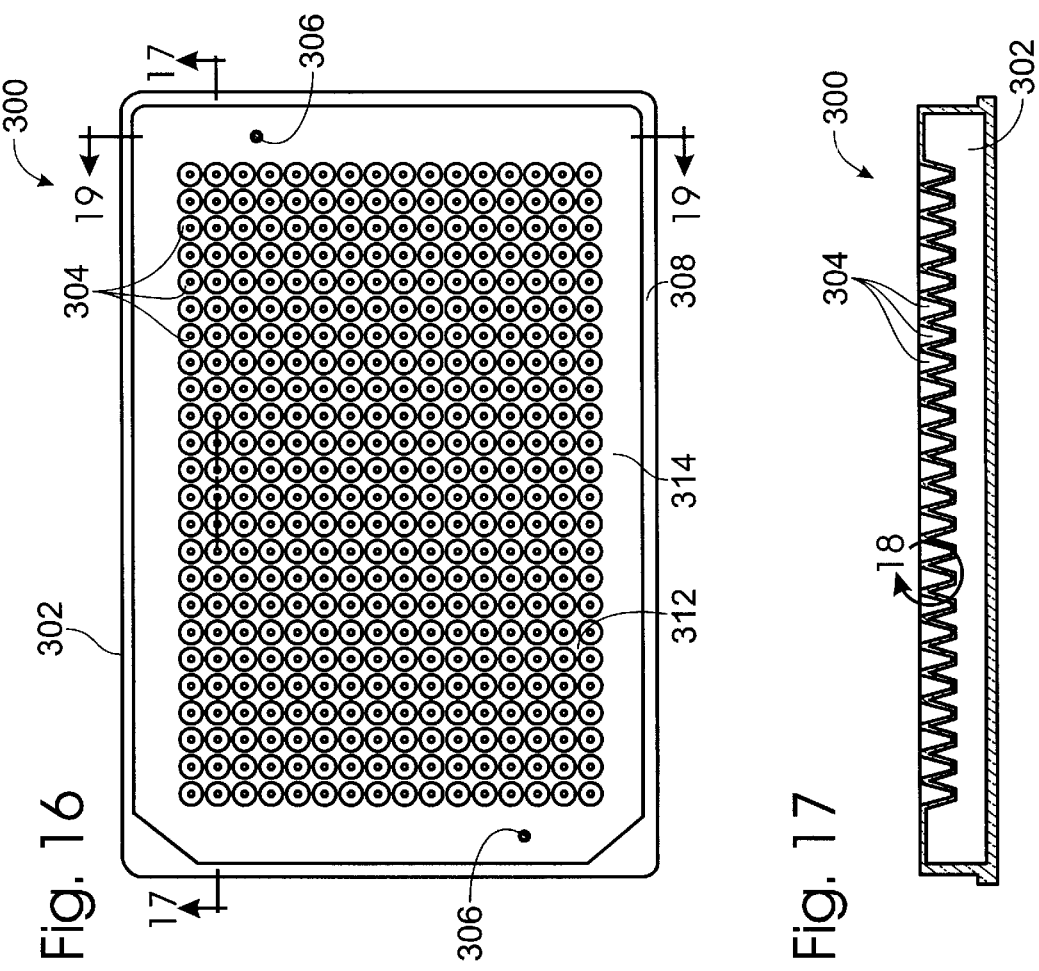
Fig. 16
Fig. 17

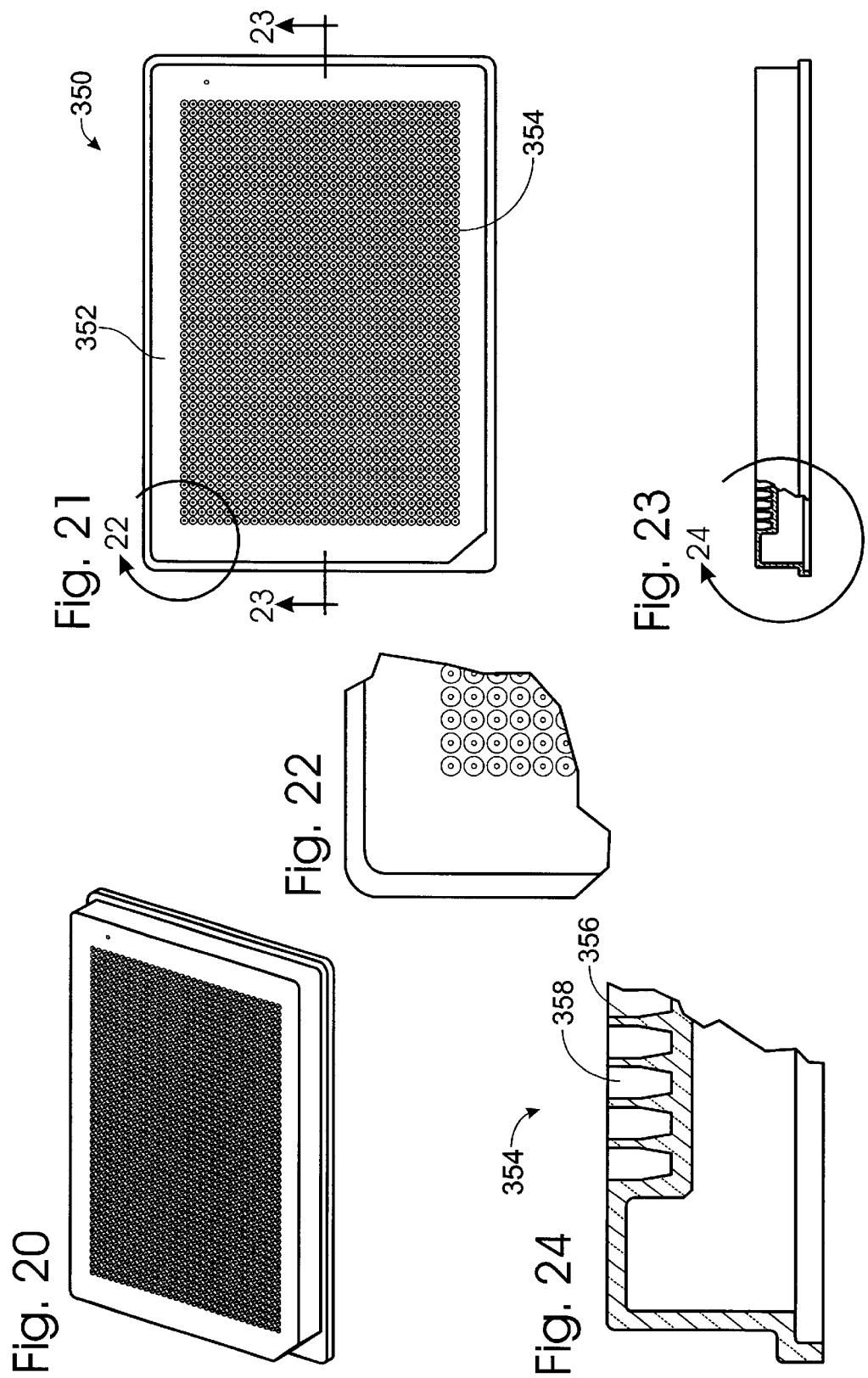

METHODS AND APPARATUS FOR DETECTING POLYNUCLEOTIDE HYBRIDIZATION

CROSS-REFERENCES

This application is a continuation of PCT Patent Application Ser. No. PCT/US00/00895, filed Jan. 14, 2000, published in English as Int. Pub. No. WO 00/42209 (Jul. 20, 2000), which is incorporated herein by reference.

This application claims priority from the following U.S. Provisional Patent Applications: Serial No. 60/116,113, filed Jan. 15, 1999, Serial No. 60/135,284, filed May 21, 1999; and Ser. No. 60/167,463, filed Nov. 24, 1999, all of which are incorporated herein by reference.

This application also claims priority from the following PCT patent applications: Serial No. PCT/US99/01656, filed Jan. 25, 1999; and Serial No. PCT/US99/08410, filed Apr. 16, 1999, both of which are incorporated herein by reference.

This application hereby incorporates the following U.S. patent applications by reference: Ser. No. 09/062,472, filed Apr. 17, 1998; Ser. No. 09/160,533, filed Sep. 24, 1998; Ser. No. 09/349,733, filed Jul. 8, 1999; and Ser. No. 09/468,440, filed Dec. 21, 1999.

This application also hereby incorporates the following PCT patent applications by reference: Serial No. PCT/US98/23095, filed Oct. 30, 1998; Serial No. PCT/US99/03678, filed Feb. 19, 1999; Serial No. PCT/US99/16057, filed Jul. 15, 1999; Serial No. PCT/US99/16453, filed Jul. 21, 1999; Serial No. PCT/US99/16621, filed Jul. 23, 1999; Serial No. PCT/US99/16286, filed Jul. 26, 1999; Ser. No. PCT/US99/16287, filed Jul. 26, 1999; and Ser. No. PCT/US99/24707, filed Oct. 19, 1999.

This application is based upon and claims benefit under 35 U.S.C. § 119 of the following U.S. provisional patent applications, each of which is incorporated herein by reference: Serial No. 60/117,278, filed Jan. 26, 1999; Serial No. 60/119,884, filed Feb. 12, 1999; Serial No. 60/121,229, filed Feb. 23, 1999; Serial No. 60/124,686, filed Mar. 16, 1999; Serial No. 60/125,346, filed Mar. 19, 1999; Serial No. 60/130,149, filed Apr. 20, 1999; Serial No. 60/132,262, filed May 3, 1999; Serial No. 60/132,263, filed May 3, 1999; Serial No. 60/138,311, filed Jun. 9, 1999; Serial No. 60/138,438, filed Jun. 10, 1999; Serial No. 60/138,737, filed Jun. 11, 1999; Serial No. 60/138,893, filed Jun. 11, 1999; Serial No. 60/142,721, filed Jul. 7, 1999; Serial No. 60/153,251, filed Sep. 10, 1999; Serial No. 60/164,633, filed Nov. 10, 1999; Serial No. 60/165,813, filed Nov. 16, 1999; and Ser. No. 60/137,301, filed Nov. 24, 1999.

This application also incorporates by reference the following publications: William Bains, *Biotechnology from A to Z* (1993); Richard P. Haughland, *Handbook of Fluorescent Probes and Research Chemicals* (6$^{th}$ ed. 1996); Joseph R. Lakowicz, *Principles of Fluorescence Spectroscopy* (2$^{nd}$ Edition 1999); and Bob Sinclair, *Everything's Great When it Sits on a Chip: A Bright Future for DNA Arrays*, 13 THE SCIENTIST, May 24, 1999, at 18.

FIELD OF THE INVENTION

The invention relates to polynucleotides. More particularly, the invention relates to methods and apparatus for detecting polynucleotide hybridization in luminescence-based assays.

BACKGROUND OF THE INVENTION

Polynucleotides are linear polymers composed of covalently linked nucleotides, which in turn are composed of purines (such as adenine (A) and guanine (G)), pyrimidines (such as cytosine (C), thymidine (T), and uracil (U)), carbohydrates, and phosphoric acid. Polynucleotides may be single or double-stranded. Double-stranded polynucleotides are formed of two different single-stranded polynucleotides that bind to one another through noncovalent base-pairing interactions to form a hybrid. Such hybridization will occur if the sequences of the single-stranded polynucleotides are "complementary," so that for example wherever there is an A in one strand there is a T or a U in the other, and wherever there is a G in one strand there is a C in the other.

Polynucleotides in the form of deoxyribonucleic acid (DNA) and ribonucleic acid (RNA) encode genetic information that controls cellular function and heredity in biological systems. DNA encodes information at least in part in the form of genes. Genes are sequences of nucleotides that encode information for constructing a polypeptide. The sequence of nucleotides in a gene may vary due to insertions, deletions, repeats, inversions, translocations, and/or single and multiple nucleotide substitutions, among others. These variations may be termed polymorphisms, and genes that differ by polymorphisms may be termed alleles.

Polymorphisms may lead to observable differences in phenotype. Familiar polymorphisms in humans include (1) variations in glycosyltransferase genes associated with the ABO blood groups, (2) variations in the apoE gene associated with Alzheimer's disease, (3) variations in the CCR5 chemokine receptor gene associated with resistance to HIV infection, and (4) variations in the hemoglobin gene associated with sickle cell anemia.

Detection of nucleotide polymorphisms may play an important role in studies of biodiversity, evolution, and bio-identity, as well as in the understanding and treatment of disease. Detection of nucleotide polymorphisms can be facilitated using high-throughput screening (HTS). In HTS, hundreds of thousands of samples may be analyzed. Maximum efficiency in terms of speed and automation are desirable to process as many samples as possible, as rapidly as possible, and accuracy is desirable to avoid registering false positives and false negatives.

Detection of nucleotide polymorphisms also can be facilitated using luminescence assays. Luminescence is the emission of light from an excited electronic state of a "luminophore," i.e., a luminescent atom or molecule. In a luminescence assay, a luminophore is included in a system, and properties of the light emitted by the luminophore are used to characterize components and properties of the system. Such light may include fluorescence and phosphorescence, and such properties may include hybridization/binding reactions and enzymatic activity, among others. In this sense, the analyte may act as a reporter to provide information about another material or target substance that is the focus of the assay. Luminescence assays may use various properties of the luminescence, including its intensity, polarization, and/or lifetime.

Luminescence polarization assays involve the absorption and emission of polarized light. (Here, polarization refers to the direction of light's electric field, which generally is perpendicular to the direction of light's propagation.) In a luminescence polarization assay, a luminescent sample is illuminated with polarized excitation light, which preferentially excites luminophores having absorption dipoles aligned with the polarization of the excitation light. These molecules subsequently decay by preferentially emitting light polarized parallel to their emission dipoles. The extent to which the total emitted light is polarized depends on the extent of molecular reorientation during the lifetime of the excited state, which in turn depends on the size, shape, and environment of the reorienting molecule. Thus, luminescence polarization assays can be used to quantify the extent of hybridization between polynucleotides through the effect of hybridization on the rate of reorientation.

Recently, selected luminescence assays have been used in certain genetic analyses involving microplates and the more exotic DNA chips, the latter being arrays of DNA probes or reference sequences packed together in a small area. However, these assays suffer from a number of shortcomings related in part to shortcomings in available sample holders, luminescence detection devices, and methods of background subtraction, as described below.

Shortcomings in sample holders. Microplates are a preferred sample holder in luminescence analyses. Unfortunately, despite their demonstrated utility, standard microplates suffer from a number of shortcomings. For example, sample wells in microplates and other sample holders for luminescence assays may have regions that are optically inaccessible, from which luminescence can be neither excited nor detected. Sample in such regions effectively is wasted because it does not contribute to the analysis. Wasted sample can translate into significant extra cost, particularly for assays that are performed in large numbers, that use expensive reagents, and/or that are inhomogeneous, requiring washing. Sample wells also may have walls or other regions that are themselves detectable optically, increasing background if such regions luminesce.

Shortcomings in luminescence detection devices. Photoluminescence requires illuminating a sample with light from a light source, and detecting light emitted from the sample. Photoluminescence detection devices may employ various light sources. In academic research laboratories, light sources for luminescence polarization assays have included lasers and arc lamps (e.g., xenon arc lamps). Unfortunately, these light sources suffer from a number of shortcomings. The gas in xenon arc lamps is under high pressure (about 10 atmospheres), so that explosion is always a danger. The power supplies for lasers and xenon arc lamps operate at very high currents (about 25 amps) and voltages (about 20,000 to 40,000 volts), so that electrocution and other health hazards are always a danger. In particular, the power supplies for arc lamps produce ozone and may deliver a lethal shock when the lamps are started. The power supplies also may produce transients that can damage other electronic components of the system. The light emitted by lasers and xenon arc lamps is very intense, so that eye damage is always a danger. In particular, the extreme brightness may damage the retina, and ultraviolet light emitted by xenon arc lamps and some lasers may damage the cornea. The spectral output of lasers and some (e.g., mercury) arc lamps is very limited, so that desired excitation wavelengths may not be available. The lifetime of arc lamps may be very short, typically around 300 hours, so that the lamp must be changed frequently, further exposing the operator to dangers posed by the lamp and power supply.

These shortcomings assume even greater significance outside the research laboratory. For example, in high-throughput screening applications, the light source may be used nearly continuously, so that the dangers posed by lasers and arc lamps are ever present. The light source also may be used by relatively unskilled operators, who may be unfamiliar with or unreceptive to safety issues.

In high-throughput screening laboratories, light sources for luminescence polarization assays have included incandescent (e.g., tungsten) lamps and flash lamps. Incandescent lamps are relatively common and inexpensive, and include lamps from overhead projectors. Incandescent lamps put out broad-spectrum light, so that they may be used with a variety of luminescent compounds. Flash lamps are more exotic, but provide some advantages over incandescent lamps. In particular, flash lamps may be used for both time-resolved and steady-state measurements. This flexibility allows the same light source to be used in instruments that perform multiple assays, such as steady-state and time-resolved luminescence polarization assays. Moreover, flash lamps may have long lifetimes, as long as 10,000 hours.

Shortcomings in methods of background subtraction. Optical spectroscopic assays are subject to artifacts that alter the apparent luminescence of the analyte and thus the accuracy, repeatability, and reliability of the assay. Some artifacts increase the apparent luminescence of the analyte, causing intensity-based assays to overreport the amount of light emitted by the analyte. Such artifacts include background. Other artifacts decrease the apparent luminescence of the analyte, causing intensity-based assays to underreport the amount of light emitted by the analyte. Such artifacts include scattering and absorption. Such artifacts also include changes in the composition that change the optical transfer function (photons collected/photons injected), including changes in index of refraction and surface tension.

Optical spectroscopic assays also are subject to artifacts that alter the apparent polarization of the analyte. Such artifacts also include background, scattering, and absorption, among others, and can increase or decrease the apparent polarization.

Among artifacts that alter polarization while increasing the apparent luminescence of the analyte, background is especially significant. Background refers to light and other signals that do not arise from the analyte, but that can be confused with light that does arise from the analyte. Background may arise from non-analyte luminescent components of the sample (e.g., library compounds, target molecules, etc.). Background also may arise from luminescent components of the sample container and detection system (e.g., microplates, optics, fiber optics, etc.). Background also may arise from scattered excitation light that leaks through the optical filters, which is equivalent to luminescence with a zero lifetime, and from room light.

There is no way to eliminate every source of background, so methods must be used to discriminate between analyte and background. If the analyte and background have different spectra, background may be at least partially discriminated using appropriate optical filters, which pass light emitted by the analyte but block background. If the analyte and background have overlapping spectra, background may be at least partially discriminated in two ways. First, background may be discriminated using a blank. In this method, data such as intensity data are collected for the sample and for a blank that lacks analyte but otherwise resembles the sample. Background is at least partially discriminated by subtracting the data obtained from the blank from the data obtained from the sample. Second, background may be discriminated by gating. In this method, data are collected from the sample only at times when the background is low or nonexistent.

Unfortunately, these methods of rejecting background suffer from a number of shortcomings, especially if the analyte and background have overlapping spectra. The use of blanks requires making two measurements for every sample, at least if the background is different for each sample. Background may be different for each sample if each sample is housed in a different container and/or if each sample contains a different, intrinsically luminescent target molecule, such as a peptide, protein, or nucleic acid, among others. The use of gating requires knowledge of the lifetime and intensity of the background. The use of gating also requires collecting data only over limited times, so that data collection is slowed and potentially useful data is discarded. Gating is especially problematic for short-lifetime background, because luminescence from the analyte is most intense for short times after excitation.

Among artifacts that alter polarization while decreasing the apparent luminescence of the analyte, scattering and absorption are especially significant. Scattering can arise if the composition containing the analyte is turbid, so that excitation and/or emission light are scattered out of the optical path and therefore not detected. Absorption can arise if non-analyte components of the composition can absorb excitation and/or emission light. Absorption of excitation light reduces luminescence indirectly, by reducing the amount of light available to excite luminescence. Absorption of emission light reduces luminescence directly. Collectively, absorption of excitation and emission light is termed "color quenching." Scattering and color quenching may vary from sample to sample and therefore be difficult to characterize.

There is no way to eliminate every source of scattering and absorption. This is especially true in compositions containing biological molecules, because biological molecules such as nucleic acids and proteins may absorb light having wavelengths commonly used in luminescence assays.

Background, scattering, absorption, and other artifacts affecting apparent luminescence are significant shortcomings, even for single measurements. However, they are potentially crippling shortcomings in high-throughput genomics applications, where tens or hundreds of thousands of samples may be analyzed each day. In genomics applications, the use of blanks may double the consumption of reagents and the time required for sample preparation and data collection, as well as associated costs. Moreover, in genomics applications, biological molecules that scatter and absorb light often must be employed.

SUMMARY OF THE INVENTION

The invention provides methods and apparatus for detecting polynucleotide hybridization in luminescence-based assays.

BRIEF DESCRIPTION OF THE DRAWINGS

FIG. 6 is a schematic view of photoluminescence optical components from the apparatus of FIG. 4.

FIG. 7 is a schematic view of chemiluminescence optical components from the apparatus of FIG. 4.

FIG. 12 is a top view of a 96-well microplate constructed in accordance with the invention.

FIG. 13 is a cross-sectional view of the microplate in FIG. 12, taken generally along line 13—13 in FIG. 12.

FIG. 14 is a first enlarged portion of the cross-sectional view in FIG. 13, showing details of a sample well.

FIG. 15 is a second enlarged portion of the cross-sectional view in FIG. 13, showing details of a reference fiducial.

FIG. 16 is a top view of a 384-well microplate constructed in accordance with the invention.

FIG. 17 is a cross-sectional view of the microplate in FIG. 16, taken generally along line 17—17 in FIG. 16.

FIG. 18 is an enlarged portion of the cross-sectional view in FIG. 16, showing details of a sample well.

FIG. 19 is an enlarged cross-sectional view of the microplate in FIG. 16, taken generally along line 19—19 in FIG. 16, showing details of a reference fiducial.

FIG. 20 is a perspective view of a 1536-well microplate constructed in accordance with the invention.

FIG. 21 is a top view of the microplate in FIG. 20.

FIG. 22 is an enlarged portion of the top view in FIG. 21, showing details of the sample wells.

FIG. 23 is a cross-sectional view of the microplate in FIG. 20, taken generally along line 23—23 in FIG. 20.

FIG. 24 is an enlarged portion of the cross-sectional view in FIG. 23, showing details of the sample wells.

DETAILED DESCRIPTION OF THE INVENTION

Figure 1:
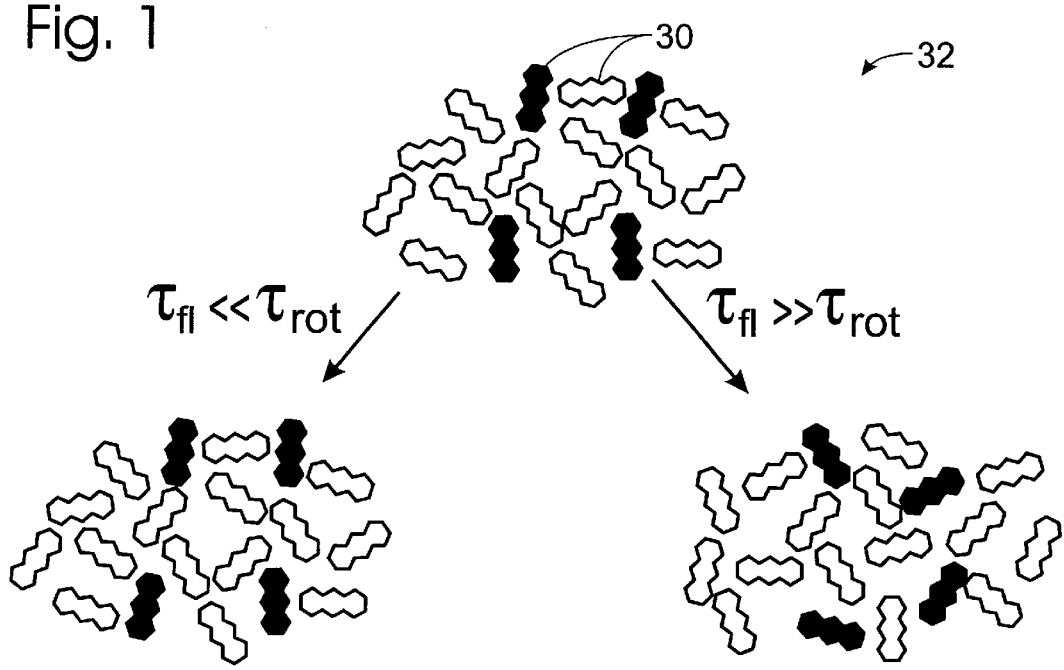
FIG. 1 is a schematic view of luminescently labeled molecules, showing how molecular reorientation affects luminescence polarization.

The invention provides methods and apparatus for detecting polynucleotide hybridization in luminescence-based assays. The methods may include (1) providing a substrate having at least two assay sites, (2) locating a different reference polynucleotide at each assay site, (3) depositing substantially equal amounts of a sample polynucleotide at each assay site under conditions conducive to hybridization, where at least one of the reference and sample polynucleotides at each assay site is labeled with a luminophore, (4) illuminating each assay site with polarized light, (5) detecting polarized light transmitted from each assay site, and (6) deriving information relating to the sequence of the sample polynucleotide by comparing the extent of polarization of the light emitted from each assay site. The kits may include (1) a substrate having plural assay sites, (2) a plurality of reference polynucleotides, each reference polynucleotide having a different sequence, and (3) a luminophore capable of labeling a polynucleotide. The steps, components, and other elements in these and other aspects of the invention are described in detail below.

The invention may have significant advantages over the prior art. For example, the methods may reduce the amounts of sample and reagents required for detecting hybridization and allow the use of relatively standard microplate technology in addition to the more exotic DNA chip technology. Microplate technology may reduce cost and provide faster turn around time for custom DNA arrays, since it is not necessary to produce a chip corresponding to the custom array.

The substrate referred to above includes any material capable of supporting reference and sample polynucleotides for luminescence analysis at one or more assay sites. Suitable substrates include microplates, DNA arrays (such as biochips), and hybridization chambers, among others, where features such as microplate wells and DNA array sites may comprise the assay sites. Preferred microplates are described below in Section 6. Preferred DNA arrays are described in Bob Sinclair, *Everything's Great When It Sits on a Chip: A Bright Future for DNA Arrays,* 13 THE SCIENTIST, May 24, 1999, at 18. Preferred hybridization chambers are described in PCT patent application Ser. No. PCT/US99/03678, which is incorporated herein by reference.

The polynucleotides include any nucleic acid or nucleic acid analog capable of binding or specifically coming together with a complementary polynucleotide to form a hybrid, even if that complementary polynucleotide is not present in the assay. The polynucleotides include deoxyribonucleic acids (DNAs), ribonucleic acids (RNAs), and peptide nucleic acids (PNAs), among others, as well as fragments, derivatives, and analogs thereof. The polynucleotides may be single stranded, double stranded, or multiply stranded. If the polynucleotides are double or multiply stranded, the method may include treating (e.g., heating or otherwise denaturing) the polynucleotides to permit access and/or binding to the polynucleotide by a complementary polynucleotide. The polynucleotides may be of any length, from oligonucleotides having fewer than about 100 bases to long chromosomes having millions of bases.

The reference polynucleotides are used to probe or otherwise gather information about the sample polynucleotide. For this reason, the reference polynucleotides may differ in sequence or other properties from assay site to assay site. Examples of reference polynucleotides include an oligonucleotide library for probing for specific short sequences and a gene library for probing for long sequences.

The sample polynucleotide is the analyte or unknown polynucleotide probed by the reference polynucleotides. The sample polynucleotide may be an unknown nucleic acid whose identity is to be deduced by the reference polynucleotides. The sample polynucleotide also may be a known nucleic acid having a mutation whose identity is to be deduced by the reference polynucleotides. Such mutations may include insertions, deletions, repeats, inversions, translocations, single and multiple nucleotide substitutions, and/or single nucleotide polymorphisms (SNPs), among others.

The reference and sample polynucleotides can be characterized by their sequences. These sequences may be created de novo or copied or patterned after a natural sequence, such as that found in all or part of an exon, intron, gene, gene family, plasmid, cosmid, virus, virion, or chromosome, among others.

The reference and sample polynucleotides can be isolated, synthesized, and/or manipulated using standard techniques from molecular biology. Suitable techniques are described in William Bains, *Biotechnology from A to Z* (1993), which is incorporated herein by reference. For example, polynucleotides can be amplified and/or labeled using the polymerase chain reaction (PCR), among others.

The sample polynucleotide may be deposited at an assay site or otherwise brought into contact with the reference polynucleotide using any method for effectuating such deposit or contact. A preferred method is by mixing the materials in solution, although other methods such as attaching one or more components to a solid support such as a bead or surface also may be used, so long as the polynucleotides retain at least some specificity and binding affinity following such coupling.

The sample and reference polynucleotides may be brought into contact under conditions conducive to hybridization. The conditions conducive to hybridization will vary with the sample and reference polynucleotides due to the unique melting temperatures and hybridization properties of different polynucleotides. Melting temperature is determined largely by quanine/cytosine concentration in the hybrid. Generally, lower temperature and higher ionic strengths favor hybridization. However, higher temperatures and lower ionic strengths can be used to increase specificity at the expense of decreased sensitivity, because these conditions destabilize nonspecific hybrids. Generally, the concentration of reference polynucleotide should be sufficient relative to the concentration of sample polynucleotide to produce detectable hybridization between the reference and sample polynucleotides if such hybridization is appropriate, for example, by using a molar excess of reference polynucleotide.

Additional agents can be used to facilitate hybridization by destabilizing single-stranded polynucleotides, lowering melting temperatures, concentrating polynucleotides, and/or blocking and reducing nonspecific binding to substrate. For example, formamide lowers melting temperatures, so hybridizations can be performed at lower temperatures. Blocking agents (such as bovine serum albumin, sheared/denatured DNA, casein, and nonfat dry milk) reduce nonspecific binding, although they may spuriously increase polarization if they act by binding labeled polynucleotides. Excluding agents (such as dextran) effectively concentrate polynucleotides by excluding them from solution, thereby enhancing hybridization.

The extent of hybridization between the reference and sample polynucleotides can be determined using luminescence assays. In turn, the extent of hybridization can be used to deduce information such as sequence information about the sample polynucleotide. Luminescence assays are performed by illuminating assay sites and detecting light transmitted from assay sites using apparatus and methods such as those described below. The steps of illuminating and detecting may be performed on a site-by-site basis, or on at least two sites simultaneously (e.g., by detecting using a charge-coupled device).

In luminescence assays, luminescence is emitted by luminophores associated with the reference polynucleotide and/or the sample polynucleotide. Luminophores may have short (0.1–10 nanosecond) or long (10 nanosecond–1+second) luminescence lifetimes and be intrinsic or extrinsic to the polynucleotide. Typically, such luminophores will be extrinsic, such as cyanine dyes, phenanthridines (such as ethidium bromide), acridines (such as acridine orange), indoles (such as DAPI), imidazoles, psoralens, and luminescent metal-ligand and lanthanide complexes and cryptates, among others. Additional luminophores are listed in Richard P. Haugland, *Handbook of Fluorescent Probes and Research Chemicals* ($6^{th}$ ed. 1996), which is incorporated herein by reference. Extrinsic luminophores may be associated with the polynucleotides covalently or noncovalently. Luminophores may be associated covalently using various reactive groups, especially if amines or thiols are incorporated into the nucleotides during their synthesis. Luminophores may be associated noncovalently by intercalating into the polynucleotide or by binding to grooves in the polynucleotide. Luminophores also may be associated noncovalently via specific binding pairs, such as avidin and biotin, protein A and immunoglobulins, and lectins and sugars (e.g., concanavalin A and glucose).

In polarization assays, it is preferable to make any linker joining the luminophore and polynucleotide as short and/or rigid as possible, so long as hybridization properties are not significantly affected. Short and/or rigid linkers will restrict luminophore motion relative to the polynucleotide, minimizing the "propeller effect" so that the luminophore more accurately reports the motion of the free and hybridized polynucleotide. The rigidity of the linker may be increased by using amide groups in place of methylene groups, among other mechanisms.

The change in polarization upon hybridization may be increased by including an appropriately positioned energy transfer acceptor on the hybridization binding-partner, so that energy transfer would occur from the luminophore to the acceptor upon hybridization. Such energy transfer would shorten the lifetime of the luminophore, thereby increasing its polarization (because polarization varies inversely with lifetime, all else being equal).

The change in polarization upon hybridization also may be increased by decreasing the mobility of the hybrid. Mobility may be decreased by increasing the size of the hybrid, for example, by forming a complex between the reference polynucleotide, the sample polynucleotide, and a mass label prior to the step of illuminating to increase the effective volume and hence the polarization of the hybrid. Suitable mass labels include other molecules and beads, among others. The mass label approach is described in detail in PCT patent application Ser. No. PCT/US99/24707, which is incorporated herein by reference. Mobility also can be decreased by attaching the unlabeled polynucleotide to a surface, such as the surface of the sample holder. Attachment to other molecules, beads, or surfaces may be accomplished using any of a number of well-known reactive groups. It sometimes may be advantageous to attach or immobilize other reagents to a solid surface. For example, all reagents required for an experiment may be stabilized in microplate wells so that assays can be run simply by adding buffer and sample polynucleotide to the wells and performing the luminescence assay.

Genetic analysis can be performed by detecting mutations or mismatches between two strands of DNA (or other polynucleotides). A first (reference) strand may be synthesized chemically and placed into a microplate (or other substrate), either in solution phase or chemically attached or otherwise immobilized on a surface. A second (sample) strand, typically DNA from a biological sample, may be isolated, amplified by PCR, and luminescently labeled using labeled PCR primers or an equivalent technique. The labeled sample strand is then introduced into the microplate well(s) and allowed to hybridize to the reference polynucleotide(s). Mutations in the sequence of the sample can be detected or the entire sequence can be determined by examining an array of wells with different reference sequences and detecting the extent to which hybridization has occurred in each well. The ease with which mutations can be detected and the number of reference polynucleotides required will be dictated at least in part by the accuracy and precision with which the extent of hybridization can be determined. Data interpretation may be facilitated by using substantially equal amounts of reference polynucleotide at each assay site, although it is possible to compensate for differences in polynucleotide number or concentration.

In a preferred embodiment, the invention may utilize a confocal light detection device capable of detecting light substantially exclusively from a sensed volume and a microplate or other sample holder having a well shape that matches the shape of the sensed volume to detect the extent of DNA hybridization with luminescence polarization or anisotropy measurements. Specifically, the extent of hybridization can be determined using the following steps:

1. Placing the reference sequences into the wells of a "matched" microplate;
2. Dispensing the sample sequence in substantially equal amounts into each well;
3. Allowing the reference and sample sequences to hybridize;
4. Measuring the polarization or anisotropy of light transmitted from each well to determine the extent of hybridization in each well; and
5. Enhancing the sensitivity using background-subtraction methods.

The highest signal for a given sample volume is obtained when the shape of the sensed volume is matched to the shape of the microplate well. Furthermore, if the instrument has confocal optics, any changes in polarization or anisotropy that occur within the sensed volume will be detected. This allows sample volume to be reduced and reference polynucleotides either to be immobilized to the walls of the microplate or dissolved in solution. Immobilization of the reference sequence provides the greatest change in anisotropy upon hybridization, without requiring either very long reference sequences or chemical attachment of the reference sequence to a large chemical entity.

With matching between the shapes of the sensed volume and sample holder, the sample volume can be reduced to 5–10 $\mu L$. Typical samples taken from humans contain $10^6$ cells. Typical PCR amplification factors are in the range $10^{6-10^{12}}$. Simple calculations show that the number of luminescent molecules obtained from a typical PCR reaction is sufficiently high that the resulting luminescence signal will be considerably above the lower detection limit for polarization measurements in the light detection device described below, even after the sample is divided substantially equally between 96 to 1536 wells. This permits sensitive polarization measurements to be carried out, so long as the background level can be either controlled or eliminated.

The sensitivity of anisotropy or polarization measurements can be reduced by unwanted background signals. This background can be represented as a combination of (1) a relatively constant background luminescence (from well to well) having a relatively constant anisotropy and (2) random fluctuations in both the luminescence level and its anisotropy caused by luminescent contamination ("hot wells"). Background may be reduced or subtracted using various methods, including:

1. Conventional background subtraction using control wells.
2. Premeasuring the microplate and subtracting the background after the reagents are added and the measurement is completed.
3. Using FLARe technology to perform the measurement and FLAMe methods to subtract background in polarization measurements.
4. Premeasuring the background anisotropy; performing a total intensity measurement on each well; using the average value of the total intensity for all wells to determine the fractional intensity of the background of each well, because all wells should have the same total intensity; and using the anisotropy-based method for background-subtraction of polarization data described below to perform the background subtraction.

The latter methods may involve converting detected light to a signal, and discriminating between a first portion of the signal that is attributable to light emitted by the luminophore and a second portion of the signal that is attributable to a background. The discriminating step may be performed using a processor, as described below in Section 8. The processor may discriminate between the first and second portions of the signal without requiring a determination of the lifetime or intensity of the background, or without requiring the use of information obtained from a blank (irrespective of whether a significant amount of the background is being detected by a detector at the same time that light emitted by the analyte is being detected). The processor also may discriminate between the first and second portions in the frequency domain without requiring a determination of the intensity of the background, or without requiring the use of information obtained from a blank.

The invention includes additional aspects that are described below and in the several patent applications that are cross-referenced and incorporated herein by reference. For example, the invention may include combining the sample and reference polynucleotides with a luminescent reference compound, and determining the intensity of light emitted from the luminophore as a function of the intensity of light emitted from the reference compound.

The remainder of the detailed description is divided into eight sections, as follows: (1) description of selected luminescence assays, (2) description of luminescence apparatus, (3) methods of measuring luminescence, (4) signal enhancement, (5) description of preferred light sources, (6) description of microplates, (7) application of sensed volumes, and (8) background subtraction.

1. Description of Selected Luminescence Assays

Luminescence is the emission of light from excited electronic states of luminescent atoms or molecules, as described above. Luminescence generally refers to all kinds of light emission, except incandescence, and may include photoluminescence, chemiluminescence, and electrochemiluminescence, among others. In photoluminescence, including fluorescence and phosphorescence, the excited electronic state is created by the absorption of electromagnetic radiation. In chemiluminescence, which includes bioluminescence, the excited electronic state is created by a transfer of chemical energy. In electrochemiluminescence, the excited electronic state is created by an electrochemical process.

Luminescence may be used in a variety of assays, including fluorescence polarization (FP), fluorescence resonance energy transfer (FRET), fluorescence lifetime (FLT), total internal reflection (TIR) fluorescence, fluorescence correlation spectroscopy (FCS), and fluorescence recovery after photobleaching (FRAP), as well as their phosphorescence and higher-transition analogs, among others.

The remainder of this section is divided into three sections: (A) intensity assays, (B) polarization assays, and (C) time-resolved assays.

A. Intensity Assays

Luminescence intensity assays involve monitoring the intensity (or amount) of light emitted from a composition. The intensity of emitted light will depend on the extinction coefficient, quantum yield, and number of luminophores in the composition, among others. These quantities, in turn, will depend on the environment of the luminophore, including the proximity and efficacy of quenchers and energy transfer partners. Thus, luminescence intensity assays may be used to study binding reactions, among other applications.

B. Polarization Assays

Luminescence polarization assays involve monitoring the intensity of polarized light emitted from a composition. (Polarization describes the direction of light's electric field, which generally is perpendicular to the direction of light's propagation.) Luminescence polarization assays may be homogeneous and ratiometric, making them relatively insensitive to sample-to-sample variations in concentration, volume, and meniscus shape.

Luminescence polarization assays typically are used to study molecular rotation. FIG. 1 shows how luminescence polarization is affected by molecular rotation. In a luminescence polarization assay, specific molecules 30 within a composition 32 are labeled with one or more luminophores. The composition then is illuminated with polarized excitation light, which preferentially excites luminophores having absorption dipoles aligned parallel to the polarization of the excitation light. These molecules subsequently decay by preferentially emitting light polarized parallel to their emission dipoles. The extent of polarization of the total emitted light depends on the extent of molecular reorientation during the time interval between luminescence excitation and emission, which is termed the luminescence lifetime, $\tau$. In turn, the extent of molecular reorientation depends on the luminescence lifetime and the size, shape, and environment of the reorienting molecule. Thus, luminescence polarization assays can be used to quantify hybridization/binding reactions and enzymatic activity, among other applications. In particular, molecules commonly rotate via diffusion with a rotational correlation time $\tau_{rot}$ that is proportional to their size. Thus, during their luminescence lifetime, relatively large molecules will not reorient significantly, so that their total luminescence will be relatively polarized. In contrast, during the same time interval, relatively small molecules will reorient significantly, so that their total luminescence will be relatively unpolarized.

The relationship between polarization and intensity is expressed by the following equation:

$$P = \frac{I_{\parallel} - I_{\perp}}{I_{\parallel} + I_{\perp}} \quad (1)$$

Here, P is the polarization, $I_{\parallel}$ is the intensity of luminescence polarized parallel to the polarization of the excitation light, and $I_{\perp}$ is the intensity of luminescence polarized perpendicular to the polarization of the excitation light. P generally varies from zero to one-half for randomly oriented molecules (and zero to one for aligned molecules). If there is little rotation between excitation and emission, $I_{\parallel}$ will be relatively large, $I_{\perp}$ will be relatively small, and P will be close to one-half. (P may be less than one-half even if there is no rotation; for example, P will be less than one if the absorption and emission dipoles are not parallel.) In contrast, if there is significant rotation between absorption and emission, $I_{\parallel}$ will be comparable to $I_{\perp}$, and P will be close to zero. Polarization often is reported in milli-P (mP) units (1000×P), which for randomly oriented molecules will range between 0 and 500, because P will range between zero and one-half.

Polarization also may be described using other equivalent quantities, such as anisotropy. The relationship between anisotropy and intensity is expressed by the following equation:

$$r = \frac{I_{\parallel} - I_{\perp}}{I_{\parallel} + 2I_{\perp}} \quad (2)$$

Here, r is the anisotropy. Polarization and anisotropy include the same information, although anisotropy may be more simply expressed for systems containing more than one luminophore. In the description and claims that follow, these terms may be used interchangeably, and a generic reference to one should be understood to imply a generic reference to the other.

The relationship between polarization, luminescence lifetime, and rotational correlation time is expressed by the Perrin equation:

$$\left(\frac{1}{P} - \frac{1}{3}\right) = \left(\frac{1}{P_0} - \frac{1}{3}\right) \cdot \left(1 + \frac{\tau}{\tau_{rot}}\right) \quad (3)$$

Here, $P_0$ is the polarization in the absence of molecular motion (intrinsic polarization), $\tau$ is the luminescence lifetime (inverse decay rate) as described above, and $\tau_{rot}$ is the rotational correlation time (inverse rotational rate) as described above.

The Perrin equation shows that luminescence polarization assays are most sensitive when the luminescence lifetime and the rotational correlation time are similar. Rotational correlation time is proportional to molecular weight, increasing by about 1 nanosecond for each 2,400 Dalton increase in molecular weight (for a spherical molecule). For shorter lifetime luminophores, such as fluorescein, which has a luminescence lifetime of roughly 4 nanoseconds, luminescence polarization assays are most sensitive for molecular weights less than about 40,000 Daltons. For longer lifetime probes, such as Ru(bpy)$_2$dcbpy (ruthenium 2,2'-dibipyridyl 4,4'-dicarboxyl-2,2'-bipyridine), which has a lifetime of roughly 400 nanoseconds, luminescence polarization assays are most sensitive for molecular weights between about 70,000 Daltons and 4,000,000 Daltons.

C. Steady-State Versus Time-Resolved Assays

Apparatus 50, 90, and 160 may be used to conduct a variety of steady-state and time-resolved luminescence assays. Steady-state assays measure luminescence under constant illumination, using the continuous light source. Time-resolved polarization assays measure luminescence as a function of time, using either the continuous light source, with its intensity appropriately modulated, or the time-varying light source.

Luminescence assays also may use time-independent (steady-state) and/or time-dependent (time-resolved) properties of the luminescence. Steady-state assays generally are less complicated than time-resolved assays, but generally yield less information.

Time-resolved assays involve measuring the time course of luminescence emission, including the time course of luminescence polarization emission. Time-resolved assays may be conducted in the time domain or in the frequency domain, both of which are functionally equivalent.

In a time-domain measurement, the time course of luminescence is monitored directly. Typically, a composition containing a luminescent analyte is illuminated using a narrow pulse of light, and the time dependence of the intensity of the resulting luminescence emission is observed, although other protocols also may be used. For a simple molecule, the luminescence commonly follows a single-exponential decay.

In a frequency-domain measurement, the time course of luminescence is monitored indirectly, in frequency space. Typically, the composition is illuminated using light whose intensity is modulated sinusoidally at a single modulation frequency f, although other protocols (such as transforming time-domain data into the frequency domain) also may be used. The intensity of the resulting luminescence emission is modulated at the same frequency as the excitation light. However, the emission will lag the excitation by a phase angle (phase) φ, and the intensity of the emission will be demodulated relative to the intensity of the excitation by a demodulation factor (modulation) M.

Figure 2:
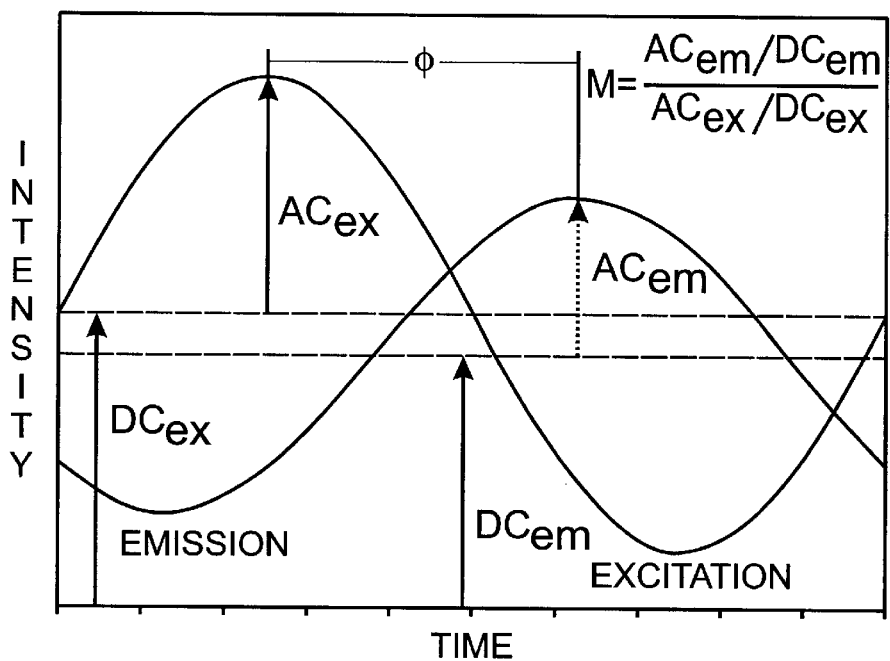
FIG. 2 is a schematic view of a frequency-domain time-resolved measurement, showing the definitions of phase angle (phase) φ and demodulation factor (modulation) M.

FIG. 2 shows the relationship between emission and excitation in a single-frequency frequency-domain experiment. The phase φ is the phase difference between the excitation and emission. The modulation M is the ratio of the AC amplitude to the DC offset for the emission, relative to the ratio of the AC amplitude to the DC offset for the excitation. The phase and modulation are related to the luminescence lifetime τ by the following equations:

$$\omega\tau = \tan(\phi) \quad (4)$$

$$\omega\tau = \sqrt{\frac{1}{M^2} - 1} \quad (5)$$

Here ω is the angular modulation frequency, which equals 2π times the modulation frequency. For maximum sensitivity, the angular modulation frequency should be roughly the inverse of the luminescence lifetime. Lifetimes of interest in high-throughput screening vary from less than 1 nanosecond to greater than 1 millisecond. Therefore, instruments for high-throughput screening should be able to cover modulation frequencies from less than about 200 Hz to greater than about 200 MHz.

2. Description of Luminescence Apparatus

FIGS. 3–9 show apparatus 50, 90, 260 for detecting light transmitted from a composition. These apparatus may include a variety of components, some or all of which may be used in any given assay. These components include (1) a stage for supporting the composition, (2) one or more light sources for delivering light to a composition, (3) one or more detectors for receiving light transmitted from the composition and converting it to a signal, (4) first and second optical relay structures for relaying light between the light source, composition, and detector, and (5) a processor for analyzing the signal from the detector. These apparatus can be used for a variety of assays, including but not limited to the assays described above. Components of the optical system can be chosen to optimize sensitivity and dynamic range for each assay supported by the apparatus. Toward this end, optical components with low intrinsic luminescence are preferred. In addition, some components may be shared by different modes, whereas other components may be unique to a particular mode. For example, in apparatus 90 and 260, absorbance, scattering, photoluminescence intensity and steady-state photoluminescence polarization modes share a light source; time-resolved absorbance and luminescence modes use their own light source; and chemiluminescence modes do not use a light source. Similarly, photoluminescence and chemiluminescence modes use different detectors.

A. Apparatus 50

Figure 3:
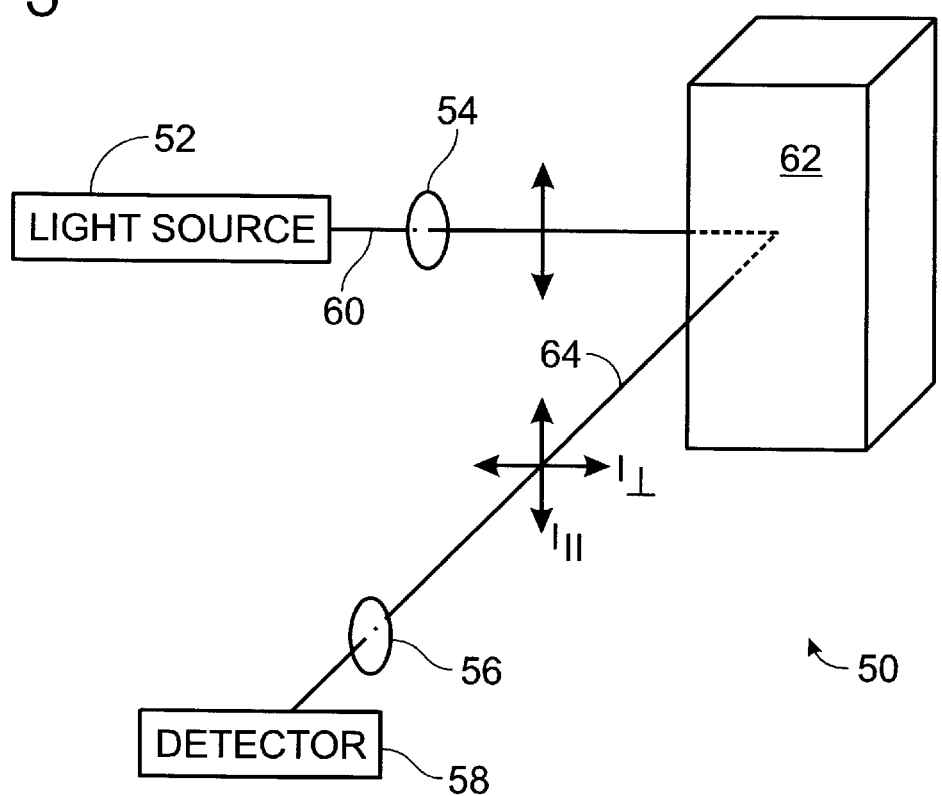
FIG. 3 is a schematic view of an apparatus for detecting light in accordance with the invention.

FIG. 3 shows an apparatus 50 for detecting light (especially polarized light) transmitted from a composition. Apparatus 50 includes a light source 52, an excitation polarizer 54, an emission polarizer 56, and a detector 58. Light 60 produced by light source 52 is directed through excitation polarizer 54, which passes polarized excitation light (indicated by vertical arrow). Polarized excitation light is directed onto a sample 62, which emits light 64 in response. The emitted light may be either some fraction of the incident light or luminescence. Emitted light 64 is directed through emission polarizer 56, which may have components oriented parallel (∥; indicated by vertical arrow) or perpendicular (⊥; indicated by horizontal arrow) to the polarization of excitation light 60. Depending on its orientation, emission polarizer 56 passes parallel ($I_\parallel$) or perpendicular ($I_\perp$) components of emission light 64 for detection by detector 58.

B. Apparatus 90

FIGS. 4–8 show an alternative apparatus 90 for detecting light transmitted from a composition. This apparatus includes (i) a photoluminescence optical system, (ii) a chemiluminescence optical system, and (iii) a housing.

Figure 4:
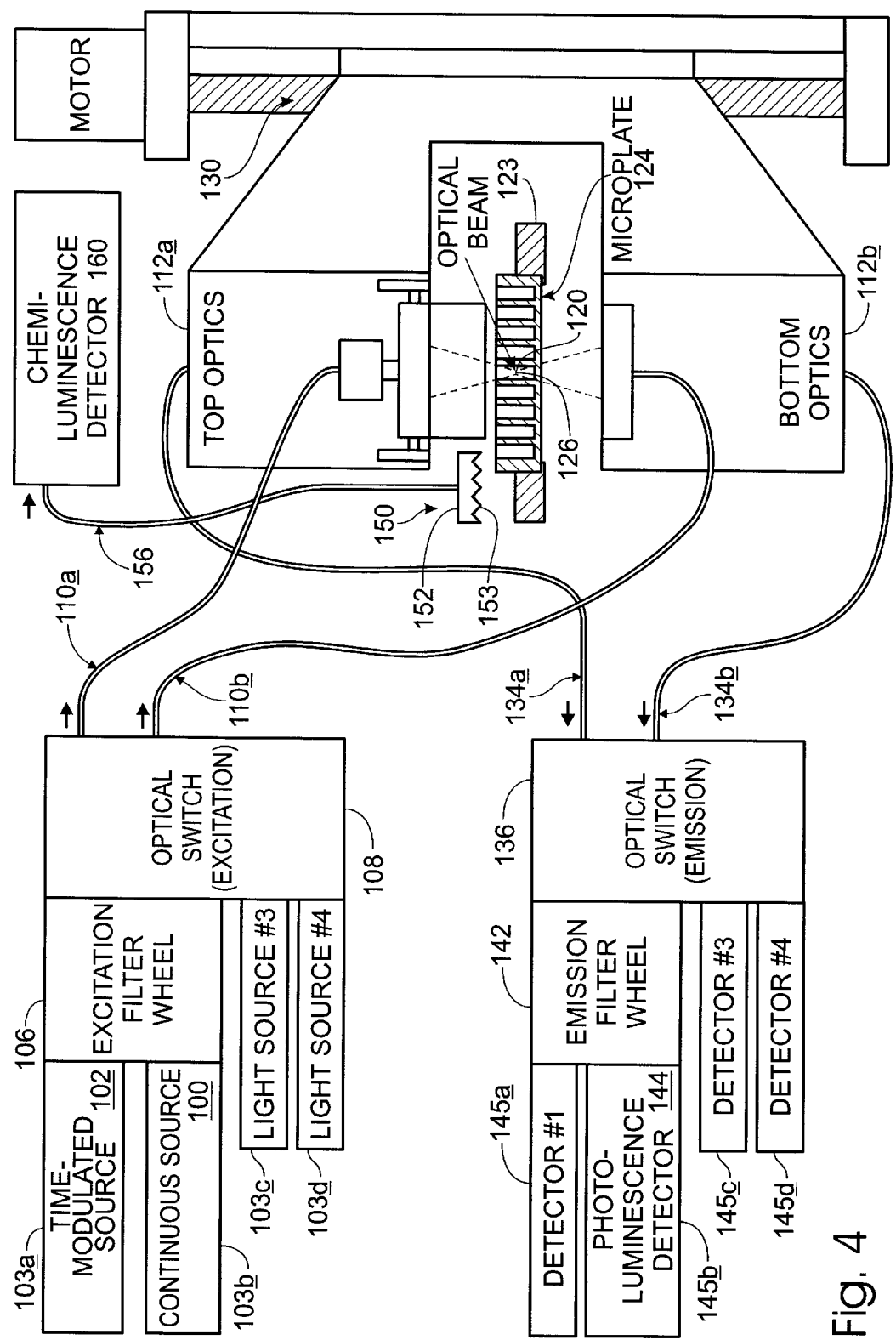
FIG. 4 is a schematic view of an alternative apparatus for detecting light in accordance with the invention.
Figure 5:
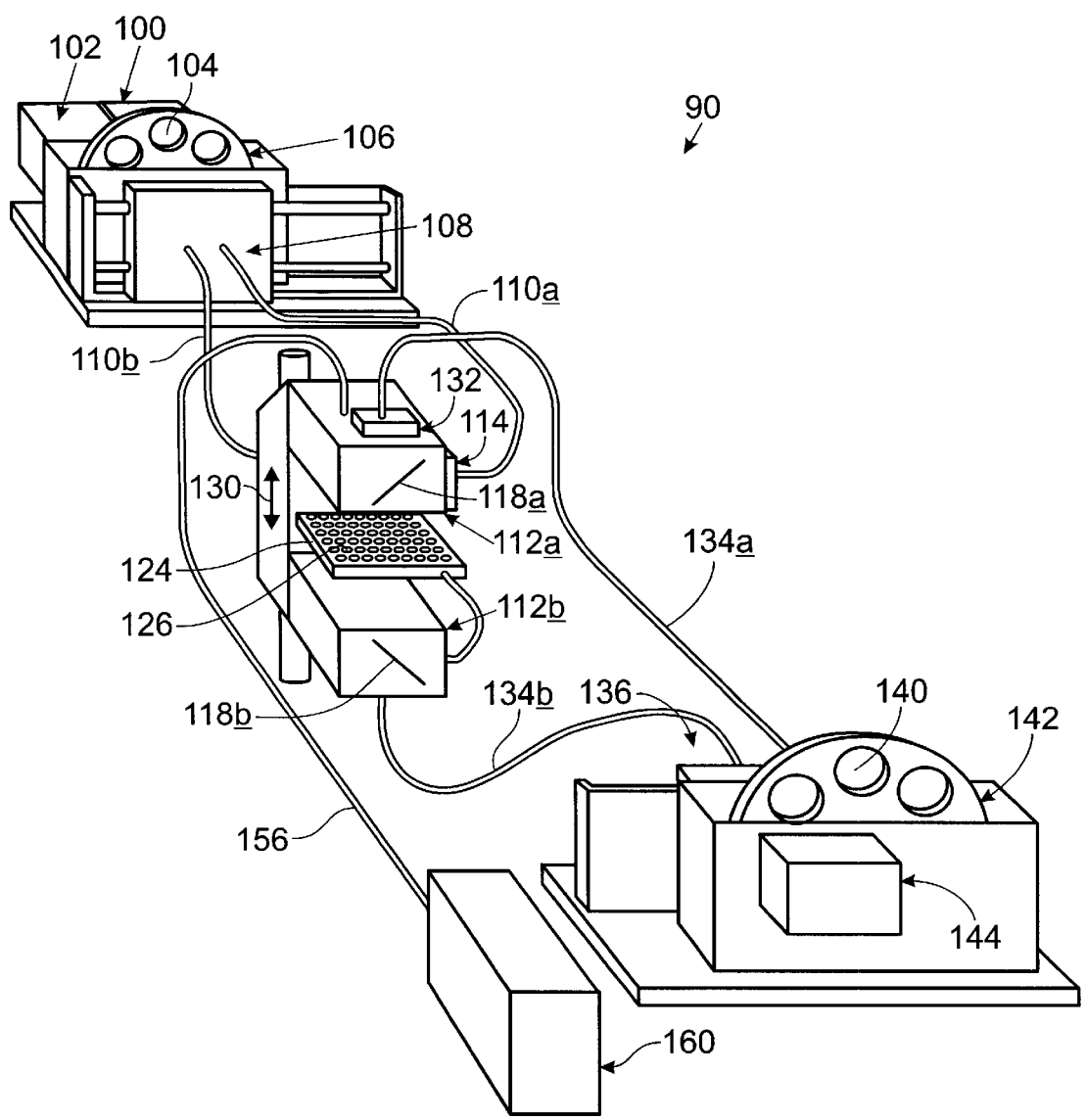
FIG. 5 is a partially schematic perspective view of the apparatus of FIG. 4.

Photoluminescence Optical System. FIGS. 4–6 show the photoluminescence (or incident light-based) optical system of apparatus 90. As configured here, apparatus 90 includes a continuous light source 100 and a time-modulated light source 102. Apparatus 90 includes light source slots 103a–d for four light sources, although other numbers of light source slots and light sources also could be provided. Light source slots 103a–d function as housings that may surround at least a portion of each light source, providing some protection from radiation and explosion. The direction of light transmission through the incident light-based optical system is indicated by arrows.

Continuous source 100 provides light for absorbance, scattering, photoluminescence intensity, and steady-state photoluminescence polarization assays. Continuous light source 100 may include arc lamps, incandescent lamps, fluorescent lamps, electroluminescent devices, lasers, laser diodes, and light-emitting diodes (LEDs), among others. A preferred continuous source is a high-intensity, high color temperature xenon arc lamp, such as a Model LX175F CERMAX xenon lamp from ILC Technology, Inc. Color temperature is the absolute temperature in Kelvin at which a blackbody radiator must be operated to have a chromaticity equal to that of the light source. A high color temperature lamp produces more light than a low color temperature lamp, and it may have a maximum output shifted toward or into visible wavelengths and ultraviolet wavelengths where many luminophores absorb. The preferred continuous source has a color temperature of 5600 Kelvin, greatly exceeding the color temperature of about 3000 Kelvin for a tungsten filament source. The preferred source provides more light per unit time than flash sources, averaged over the flash source duty cycle, increasing sensitivity and reducing read times. Apparatus 90 may include a modulator mechanism configured to vary the intensity of light incident on the composition without varying the intensity of light produced by the light source.

Time-modulated source 102 provides light for time-resolved absorbance and/or photoluminescence assays, such as photoluminescence lifetime and time-resolved photoluminescence polarization assays. A preferred time-modulated source is a xenon flash lamp, such as a Model FX-1160 xenon flash lamp from EG&G Electro-Optics. The preferred source produces a "flash" of light for a brief interval before signal detection and is especially well suited for time-domain measurements. Other time-modulated sources include pulsed lasers, electronically modulated lasers and LEDs, and continuous lamps and other sources whose intensity can be modulated extrinsically using a Pockels cell, Kerr cell, or other mechanism. Such other mechanisms may include an amplitude modulator such as a chopper as described in U.S. Provisional patent application Ser. No. 60/094,276, which is incorporated herein by reference. Extrinsically modulated continuous light sources are especially well suited for frequency-domain measurements.

In apparatus 90, continuous source 100 and time-modulated source 102 produce multichromatic, unpolarized, and incoherent light. Continuous source 100 produces substantially continuous illumination, whereas time-modulated source 102 produces time-modulated illumination. Light from these light sources may be delivered to the sample without modification, or it may be filtered to alter its intensity, spectrum, polarization, or other properties.

Light produced by the light sources follows an excitation optical path to an examination site or measurement region. Such light may pass through one or more "spectral filters," which generally comprise any mechanism for altering the spectrum of light that is delivered to the sample. Spectrum refers to the wavelength composition of light. A spectral filter may be used to convert white or multichromatic light, which includes light of many colors, into red, blue, green, or other substantially monochromatic light, which includes light of one or only a few colors. In apparatus 90, spectrum is altered by an excitation interference filter 104, which preferentially transmits light of preselected wavelengths and preferentially absorbs light of other wavelengths. For convenience, excitation interference filters 104 may be housed in an excitation filter wheel 106, which allows the spectrum of excitation light to be changed by rotating a preselected filter into the optical path. Spectral filters also may separate light spatially by wavelength. Examples include gratings, monochromators, and prisms.

Spectral filters are not required for monochromatic ("single color") light sources, such as certain lasers, which output light of only a single wavelength. Therefore, excitation filter wheel 106 may be mounted in the optical path of some light source slots 103a,b, but not other light source slots 103c,d. Alternatively, the filter wheel may include a blank station that does not affect light passage.

Light next passes through an excitation optical shuttle (or switch) 108, which positions an excitation fiber optic cable 110a,b in front of the appropriate light source to deliver light to top or bottom optics heads 112a,b, respectively. Light is transmitted through a fiber optic cable much like water is transmitted through a garden hose. Fiber optic cables can be used easily to turn light around corners and to route light around opaque components of the apparatus. Moreover, fiber optic cables give the light a more uniform intensity profile. A preferred fiber optic cable is a fused silicon bundle, which has low autoluminescence. Despite these advantages, light also can be delivered to the optics heads using other mechanisms, such as mirrors.

Light arriving at the optics head may pass through one or more excitation "polarization filters," which generally comprise any mechanism for altering the polarization of light. Excitation polarization filters may be included with the top and/or bottom optics head. In apparatus 90, polarization is altered by excitation polarizers 114, which are included only with top optics head 112a for top reading; however, such polarizers also can be included with bottom optics head 112b for bottom reading. Excitation polarization filters 114 may include an s-polarizer S that passes only s-polarized light, a p-polarizer P that passes only p-polarized light, and a blank O that passes substantially all light, when measured relative to the beamsplitter. Excitation polarizers 114 also may include a standard or ferro-electric liquid crystal display (LCD) polarization switching system. Such a system may be faster than a mechanical switcher. Excitation polarizers 114 also may include a continuous mode LCD polarization rotator with synchronous detection to increase the signal-to-noise ratio in polarization assays. Excitation polarizers 114 may be incorporated as an inherent component in some light sources, such as certain lasers, that intrinsically produce polarized light.

Light at one or both optics heads also may pass through an excitation "confocal optics element," which generally comprises any mechanism for focusing light into a "sensed volume." In apparatus 90, the confocal optics element includes a set of lenses 117a–c and an excitation aperture 116 placed in an image plane conjugate to the sensed volume, as shown in FIG. 6. Aperture 116 may be implemented directly, as an aperture, or indirectly, as the end of a fiber optic cable. Preferred apertures have diameters of 1 mm and 1.5 mm. Lenses 117a,b project an image of aperture 116 onto the sample, so that only a preselected or sensed volume of the sample is illuminated. The area of illumination will have a diameter corresponding to the diameter of the excitation aperture.

Light traveling through the optics heads is reflected and transmitted through a beamsplitter 118, which delivers reflected light to a composition 120 and transmitted light to a light monitor 122. Reflected and transmitted light both pass through lens 117b, which is operatively positioned between beamsplitter 118 and composition 120.

Beamsplitter 118 is used to direct excitation or incident light toward the sample and light monitor, and to direct light leaving the sample toward the detector. The beamsplitter is changeable, so that it may be optimized for different assay modes or compositions. If a large number or variety of photoactive molecules are to be studied, the beamsplitter must be able to accommodate light of many wavelengths; in this case, a "50:50" beamsplitter that reflects half and transmits half of the incident light independent of wavelength is optimal. Such a beamsplitter can be used with many types of molecules, while still delivering considerable excitation light onto the composition, and while still transmitting considerable light leaving the sample to the detector. If one or a few related photoactive molecules are to be studied, the beamsplitter needs only to be able to accommodate light at a limited number of wavelengths; in this case, a "dichroic" or "multichroic" beamsplitter is optimal. Such a beamsplitter can be designed with cutoff wavelengths for the appropriate sets of molecules and will reflect most or substantially all of the excitation and background light, while transmitting most or substantially all of the emission light in the case of luminescence. This is possible because the beamsplitter may have a reflectivity and transmissivity that varies with wavelength.

Light monitor 122 is used to correct for fluctuations in the intensity of light provided by the light sources. Such corrections may be performed by reporting detected intensities as a ratio over corresponding times of the luminescence intensity measured by the detector to the excitation light intensity measured by the light monitor. The light monitor also can be programmed to alert the user if the light source fails. A preferred light monitor is a silicon photodiode with a quartz window for low autoluminescence.

The composition (or sample) may be held in a sample holder supported by a stage 123. The composition can include compounds, mixtures, surfaces, solutions, emulsions, suspensions, cell cultures, fermentation cultures, cells, tissues, secretions, and/or derivatives and/or extracts thereof. Analysis of the composition may involve measuring the presence, concentration, or physical properties (including interactions) of a photoactive analyte in such a composition. Composition may refer to the contents of a single microplate well, or several microplate wells, depending on the assay. In some embodiments, such as a portable apparatus, the stage may be intrinsic to the instrument.

The sample holder can include microplates, biochips, or any array of samples in a known format. In apparatus 90, the preferred sample holder is a microplate 124, which includes a plurality of microplate wells 126 for holding compositions. Microplates are typically substantially rectangular holders that include a plurality of sample wells for holding a corresponding plurality of samples. These sample wells are normally cylindrical in shape although rectangular or other shaped wells are sometimes used. The sample wells are typically disposed in regular arrays. The "standard" microplate includes 96 cylindrical sample wells disposed in a 8×12 rectangular array on 9 millimeter centers.

The sensed volume typically has an hourglass shape, with a cone angle of about 25° and a minimum diameter ranging between 0.1 mm and 2.0 mm. For 96-well and 384-well microplates, a preferred minimum diameter is about 1.5 mm. For 1536-well microplates, a preferred minimum diameter is about 1.0 mm. The size and shape of the sample holder may be matched to the size and shape of the sensed volume, as described in PCT patent application Ser. No. PCT/US99/08410, which is incorporated herein by reference.

The position of the sensed volume can be moved precisely within the composition to optimize the signal-to-noise and signal-to-background ratios. For example, the sensed volume may be moved away from walls in the sample holder to optimize signal-to-noise and signal-to-background ratios, reducing spurious signals that might arise from luminophores bound to the walls and thereby immobilized. In apparatus 90, position in the X,Y-plane perpendicular to the optical path is controlled by moving the stage supporting the composition, whereas position along the Z-axis parallel to the optical path is controlled by moving the optics heads using a Z-axis adjustment mechanism 130, as shown in FIGS. 4 and 5. However, any mechanism for bringing the sensed volume into register or alignment with the appropriate portion of the composition also may be employed.

The combination of top and bottom optics permits assays to combine: (1) top illumination and top detection, or (2) top illumination and bottom detection, or (3) bottom illumination and top detection, or (4) bottom illumination and bottom detection. Same-side illumination and detection, (1) and (4), is referred to as "epi" and is preferred for photoluminescence and scattering assays. Opposite-side illumination and detection, (2) and (3), is referred to as "trans" and has been used in the past for absorbance assays. In apparatus 90, epi modes are supported, so the excitation and emission light travel the same path in the optics head, albeit in opposite or anti-parallel directions. However, trans modes also can be used with additional sensors, as described below. In apparatus 90, top and bottom optics heads move together and share a common focal plane. However, in other embodiments, top and bottom optics heads may move independently, so that each can focus independently on the same or different sample planes.

Generally, top optics can be used with any sample holder having an open top, whereas bottom optics can be used only with sample holders having optically transparent bottoms, such as glass or thin plastic bottoms. Clear bottom sample holders are particularly suited for measurements involving analytes that accumulate on the bottom of the holder.

Light is transmitted by the composition in multiple directions. A portion of the transmitted light will follow an emission pathway to a detector. Transmitted light passes through lens 117c and may pass through an emission aperture 131 and/or an emission polarizer 132. In apparatus 90, the emission aperture is placed in an image plane conjugate to the sensed volume and transmits light substantially exclusively from this sensed volume. In apparatus 90, the emission apertures in the top and bottom optical systems are the same size as the associated excitation apertures, although other sizes also may be used. The emission polarizers are included only with top optics head 112a. The emission aperture and emission polarizer are substantially similar to their excitation counterparts. Emission polarizer 132 may be included in detectors that intrinsically detect the polarization of light.

Excitation polarizers 114 and emission polarizers 132 may be used together in nonpolarization assays to reject certain background signals. Luminescence from the sample holder and from luminescent molecules adhered to the sample holder is expected to be polarized, because the rotational mobility of these molecules should be hindered. Such polarized background signals can be eliminated by "crossing" the excitation and emission polarizers, that is, setting the angle between their transmission axes at 90°. As described above, such polarized background signals also can be reduced by moving the sensed volume away from walls of the sample holder. To increase signal level, beamsplitter 118 should be optimized for reflection of one polarization and transmission of the other polarization. This method will work best where the luminescent molecules of interest emit relatively unpolarized light, as will be true for small luminescent molecules in solution.

Transmitted light next passes through an emission fiber optic cable 134a,b to an emission optical shuttle (or switch) 136. This shuttle positions the appropriate emission fiber optic cable in front of the appropriate detector. In apparatus 90, these components are substantially similar to their excitation counterparts, although other mechanisms also could be employed.

Light exiting the fiber optic cable next may pass through one or more emission "intensity filters," which generally comprise any mechanism for reducing the intensity of light. Intensity refers to the amount of light per unit area per unit time. In apparatus 90, intensity is altered by emission neutral density filters 138, which absorb light substantially independent of its wavelength, dissipating the absorbed energy as heat. Emission neutral density filters 138 may include a high-density filter H that absorbs most incident light, a medium-density filter M that absorbs somewhat less incident light, and a blank O that absorbs substantially no incident light. These filters may be changed manually, or they may be changed automatically, for example, by using a filter wheel. Intensity filters also may divert a portion of the light away from the sample without absorption. Examples include beam splitters, which transmit some light along one path and reflect other light along another path, and Pockels cells, which deflect light along different paths through diffraction. Examples also include hot mirrors or windows that transmit light of some wavelengths and absorb light of other wavelengths.

Light next may pass through an emission interference filter 140, which may be housed in an emission filter wheel 142. In apparatus 90, these components are substantially similar to their excitation counterparts, although other mechanisms also could be employed. Emission interference filters block stray excitation light, which may enter the emission path through various mechanisms, including reflection and scattering. If unblocked, such stray excitation light could be detected and misidentified as photoluminescence, decreasing the signal-to-background ratio. Emission interference filters can separate photoluminescence from excitation light because photoluminescence has longer wavelengths than the associated excitation light. Luminescence typically has wavelengths between 200 and 2000 nanometers.

The relative positions of the spectral, intensity, polarization, and other filters presented in this description may be varied without departing from the spirit of the invention. For example, filters used here in only one optical path, such as intensity filters, also may be used in other optical paths. In addition, filters used here in only top or bottom optics, such as polarization filters, may also be used in the other of top or bottom optics or in both top and bottom optics. The optimal positions and combinations of filters for a particular experiment will depend on the assay mode and the composition, among other factors.

Light last passes to a detector, which is used in absorbance, scattering and photoluminescence assays. In apparatus 90, there is one detector 144, which detects light from all modes. A preferred detector is a photomultiplier tube (PMT). Apparatus 90 includes detector slots 145a–d for four detectors, although other numbers of detector slots and detectors also could be provided.

More generally, detectors comprise any mechanism capable of converting energy from detected light into signals that may be processed by the apparatus, and by the processor in particular. Suitable detectors include photomultiplier tubes, photodiodes, avalanche photodiodes, charge-coupled devices (CCDs), and intensified CCDs, among others. Depending on the detector, light source, and assay mode, such detectors may be used in a variety of detection modes. These detection modes include (1) discrete (e.g., photon-counting) modes, (2) analog (e.g., current-integration) modes, and/or (3) imaging modes, among others, as described in PCT patent application Ser. No. PCT/US99/03678.

Chemiluminescence optical system. FIGS. 4, 5, and 7 show the chemiluminescence optical system of apparatus 90. Because chemiluminescence follows a chemical event rather than the absorption of light, the chemiluminescence optical system does not require a light source or other excitation optical components. Instead, the chemiluminescence optical system requires only selected emission optical components. In apparatus 90, a separate lensless chemiluminescence optical system is employed, which is optimized for maximum sensitivity in the detection of chemiluminescence.

Generally, components of the chemiluminescence optical system perform the same functions and are subject to the same caveats and alternatives as their counterparts in the incident light-based optical system. The chemiluminescence optical system also can be used for other assay modes that do not require illumination, such as electrochemiluminescence.

The chemiluminescence optical path begins with a chemiluminescent composition 120 held in a sample holder 126. The composition and sample holder are analogous to those used in photoluminescence assays; however, analysis of the composition involves measuring the intensity of light generated by a chemiluminescence reaction within the composition rather than by light-induced photoluminescence. A familiar example of chemiluminescence is the glow of the firefly.

Chemiluminescence light typically is transmitted from the composition in all directions, although most will be absorbed or reflected by the walls of the sample holder. A portion of the light transmitted through the top of the well is collected using a chemiluminescence head 150, as shown in FIG. 4, and will follow a chemiluminescence optical pathway to a detector. The direction of light transmission through the chemiluminescence optical system is indicated by arrows.

The chemiluminescence head includes a nonconfocal mechanism for transmitting light from a sensed volume within the composition. Detecting from a sensed volume reduces contributions to the chemiluminescence signal resulting from "cross talk," which is pickup from neighboring wells. The nonconfocal mechanism includes a chemiluminescence baffle 152, which includes rugosities 153 that absorb or reflect light from other wells. The nonconfocal mechanism also includes a chemiluminescence aperture 154 that further confines detection to a sensed volume.

Light next passes through a chemiluminescence fiber optic cable 156, which may be replaced by any suitable mechanism for directing light from the composition toward the detector. Fiber optic cable 156 is analogous to excitation and emission fiber optic cables 110a,b and 134a,b in the photoluminescence optical system. Fiber optic cable 156 may include a transparent, open-ended lumen that may be filled with fluid. This lumen would allow the fiber optic to be used both to transmit luminescence from a microplate well and to dispense fluids into the microplate well. The effect of such a lumen on the optical properties of the fiber optic could be minimized by employing transparent fluids having optical indices matched to the optical index of the fiber optic.

Light next passes through one or more chemiluminescence intensity filters, which generally comprise any mechanism for reducing the intensity of light. In apparatus 90, intensity is altered by chemiluminescence neutral density filters 158. Light also may pass through other filters, if desired.

Light last passes to a detector, which converts light into signals that may be processed by the apparatus. In apparatus 90, there is one chemiluminescence detector 160. This detector may be selected to optimize detection of blue/green light, which is the type most often produced in chemiluminescence. A preferred detection is a photomultiplier tube, selected for high quantum efficiency and low dark count at chemiluminescence wavelengths (400–500 nanometers).

Figure 8:
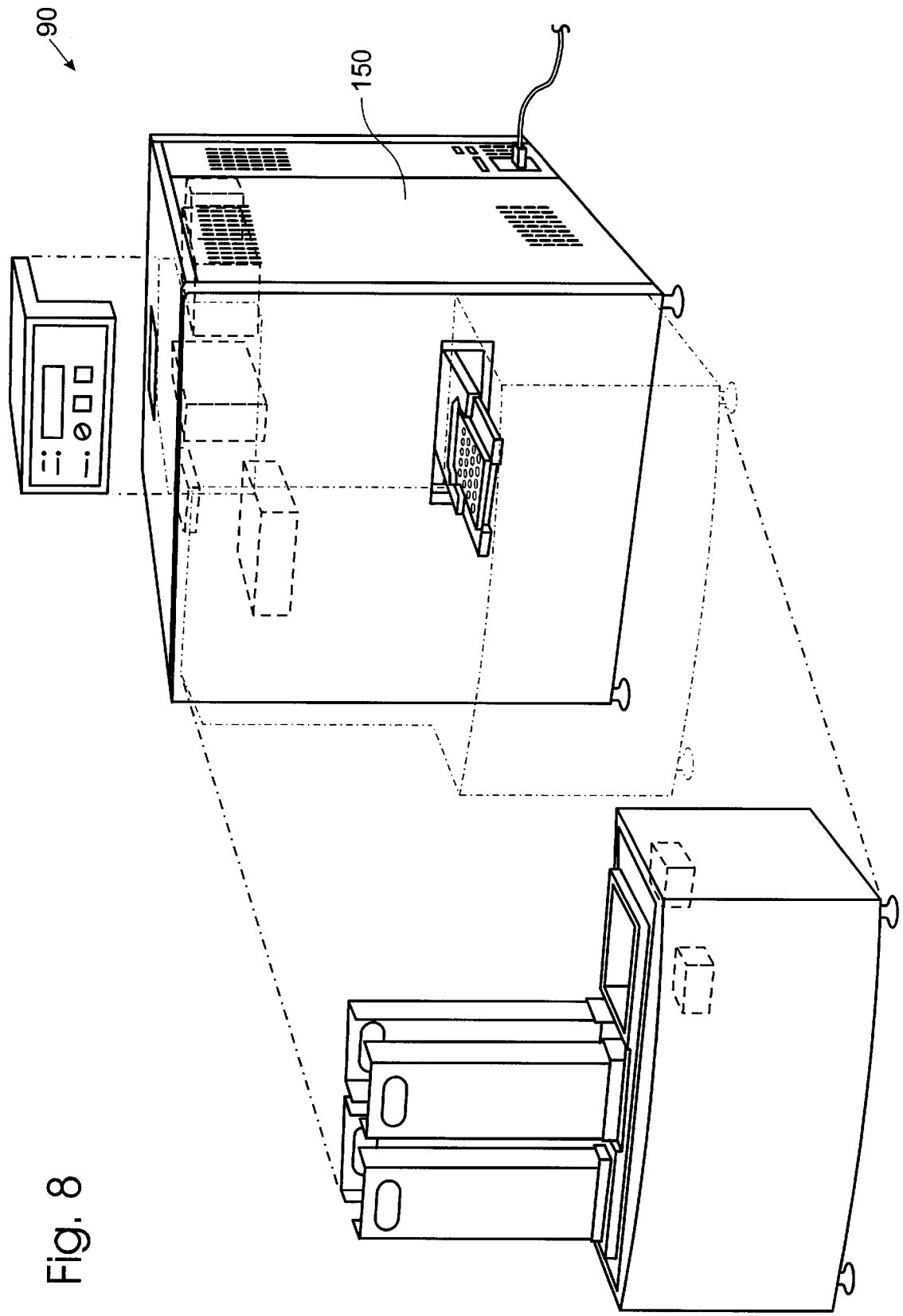
FIG. 8 is a partially exploded perspective view of a housing for the apparatus of FIG. 4.

Housing. FIG. 8 shows a housing 200 and other accessories for the apparatus of FIGS. 4–7. Housing 200 substantially encloses the apparatus, forming (together with light source slots 103a–d) two protective layers around the continuous high color temperature xenon arc lamp. Housing 200 permits automated sample loading and switching among light sources and detectors, further protecting the operator from the xenon arc lamp and other components of the system.

Additional details of an apparatus suitable for implementing features of the invention are shown in U.S. patent application Ser. No. 09/160,533, which is incorporated herein by reference.

C. Apparatus 260

Figure 9:
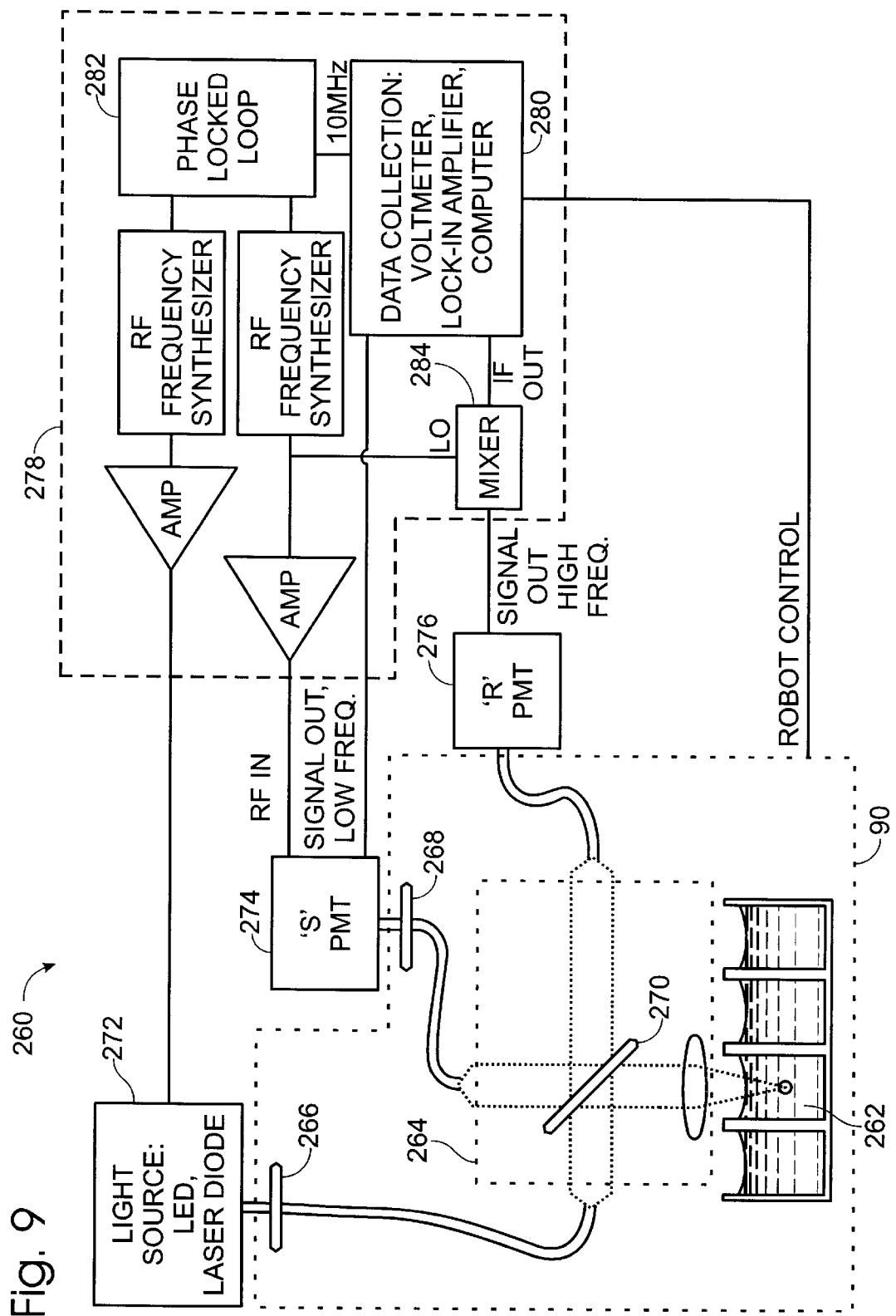
FIG. 9 is a schematic view of another alternative apparatus for detecting light in accordance with the invention.

FIG. 9 shows another alternative apparatus 260 for detecting light transmitted from a composition 262, where the detection and/or processing may be performed in the frequency-domain. Apparatus 260 includes substantial portions of apparatus 90, including its fiber-optic-coupled optics head 264, excitation 266 and emission 268 filters, dichroic beam splitter 270, and mechanisms for sample positioning and focus control. However, apparatus 260 also may include alternative light sources 272, sample ('S') detectors 274, reference ('R') detectors 276, and detection electronics 278. In FIG. 9, alternative components 272–278 are shown outside apparatus 90, but they readily may be included inside housing 250 of apparatus 90, if desired.

Apparatus 260 may provide incident light in various ways, as described above. For example, analytes absorbing blue light may be excited using a NICHIA-brand bright-blue LED (Model Number NSPB500; Mountville, Pa). This LED produces broad-spectrum excitation light, so excitation filter 266 may be selected to block the red edge of the spectrum. If analytes are excited using a laser diode, an excitation filter is not necessary.

Apparatus 260 may detect emitted light and convert it to a signal in various ways. This demodulation/deconvolution may be internal to the photodetector, or it may be performed with external electronics or software. For example, emitted light can be detected using sample detector 274, which may be an ISS-brand gain-modulated PMT (Champaign, Ill.). High-frequency emitted light can be frequency down-converted to a low-frequency signal using a technique called heterodyning. The phase and modulation of the low-frequency signal can be determined using a lock-in amplifier 280, such as a STANFORD RESEARCH SYSTEMS brand lock-in amplifier (Model Number SR830; Sunnyvale, Calif.). Lock-in amplifier 280 is phase locked using a phase-locked loop 282 to the modulation frequency of light source 272. To correct for drift in the light source, the output of light source 272 may be monitored using reference detector 276, which may be a HAMAMATSU-brand PMT (Model Number H6780; Bridgewater, N.J.). If reference detector 276 can respond to high-frequency signals, the heterodyning step can be performed using an external mixer 284. The phase and modulation of reference detector 276 also may be captured by lock-in amplifier 280 and used to normalize the signal from sample detector 274.

Apparatus 260 may be controlled by a computer or processor. The computer may direct sample handling and data collection. Generally, phase and modulation data will be collected at one or more frequencies appropriate for the lifetime of the analyte. In some cases, phase and modulation may be measured at one or a few frequencies and processed by the computer or processor to help reduce detected background.

3. Methods of Measuring Luminescence

The above-disclosed apparatus can be used to conduct a variety of steady-state and time-resolved luminescence assays, including polarization assays. Steady-state assays measure luminescence under constant illumination, using the continuous light source. Time-resolved polarization assays measure luminescence as a function of time under time-varying illumination, using either the continuous light source, with its intensity appropriately modulated, or the time-varying light source.

Intensity assays can be conducted by monitoring the intensity of the luminescence emitted by the composition.

Polarization assays can be conducted as follows. Excitation light from the continuous light source is directed through an excitation filter, low-luminescence fiber optic cable, and excitation polarization filter. Excitation light then is directed to a beamsplitter, which reflects most of the light onto a composition and transmits a little of the light into a light monitor. Emitted light from the composition is directed back through the beamsplitter and then is directed through another low-luminescence fiber optic cable, an emission filter, and a polarization filter (in either the S or P orientation) before detection by a photomultiplier tube or other detector. Two measurements are performed for each composition, one with excitation and emission polarizers aligned and one with excitation and emission polarizers crossed. Either polarizer may be static or dynamic, and either polarizer may be set in the S or P orientation, although typically the excitation polarizer is set in the S orientation. In some applications, polarized light may be transmitted to and detected from a fixed assay or examination site as successive samples are automatically, serially aligned in an optical path intersecting the examination site.

Additional luminescence assays can be conducted using procedures outlined in various patent applications cross-referenced above, Joseph R. Lakowicz, *Principles of Fluorescence Spectroscopy* ($2^{nd}$ Ed. 1999) and/or generally known to persons of ordinary skill in the art. Such additional assays include fluorescence resonance energy transfer (FRET), fluorescence lifetime (FLT), total internal reflection fluorescence (TIR), fluorescence correlation spectroscopy (FCS), and fluorescence recovery after photobleaching (FRAP), as well as their analogs based on phosphorescence and higher-order electronic transitions.

4. Signal Enhancement

Enhancements of signal-to-noise and signal-to-background ratios may be important in polarization and other luminescence assays, especially those involving dilute samples. For example, binding assays can be used to probe binding between molecules having subnanomolar dissociation coefficients, if acceptable signal-to-noise and signal-to-background ratios can be obtained from compositions having subnanomolar luminophore concentrations. The methods for enhancing signal-to-noise and signal-to-background ratios described below are especially useful with such dilute samples, thereby minimizing reagent cost that otherwise can be considerable.

Sensitivity and dynamic range can be enhanced by selecting optical components having low intrinsic luminescence and high intrinsic throughput; such as the fiber optic cables and beamsplitters described above. In such an approach, some components may be shared by different modes, whereas other components may be unique to a particular mode. For example, photoluminescence intensity and steady-state photoluminescence polarization modes may share a continuous light source; time-resolved luminescence modes may share a time-varying light source, and chemiluminescence modes may not use a light source. Similarly, photoluminescence and chemiluminescence modes may use different detectors, each selected for the application.

Sensitivity also can be enhanced by reducing the contribution of noise to the measurements. In luminescence polarization assays, various factors contribute to noise, such as (1) background noise and (2) intensity noise. Background noise refers to contributions to the signal from luminescent species other than the luminescent species of interest, including luminescent species in the apparatus and sample holder. Intensity noise refers to fluctuations in light intensity, including those arising from photon noise.

Background noise can be reduced by reducing autoluminescence from the apparatus and sample holder. For example, the apparatus may use low luminescence components, such as fused silica fiber optic cables. Similarly, the sample holder or substrate may be constructed of low luminescence materials, such as black polystyrene.

Background noise also can be reduced by reducing detection of luminescence from components of the sample that are bound to the sample holder and immobilized, spuriously increasing polarization. For example, the walls of the sample holder may be constructed or treated to reduce binding. Alternatively, in apparatus capable of detecting light transmitted substantially exclusively from a sensed volume (such as apparatus 90 and 260 described above), the sensed volume may be positioned near the center of the composition, away from the walls of the sample holder.

Intensity noise can be reduced by correcting for fluctuations in light source intensity, among others. Light source fluctuations arise due to fluctuations in power from the power supply and drift in the position of the arc in arc lamps, among others. Light source fluctuations can lead to luminescence fluctuations, because the amount of luminescence is proportional to the amount of excitation light. Luminescence fluctuations are especially problematic in luminescence polarization assays, because such assays involve comparing the magnitude of successively measured luminescence signals. Light source fluctuations can be reduced by choosing a stable light source and by resealing the luminescence signal using information obtained from a light source monitor, as described above.

Intensity noise also can be reduced by increasing the number of photons (i.e., the amount of light) detected, which reduces photon noise. Photon (or shot) noise arises due to the statistical nature of light and can be described by the same statistical law used to describe radiation decay. In particular, if an average of N photons are detected during a given time interval, the standard deviation in that number due to photon noise will be $\sqrt{N}$. The relative significance of photon noise decreases as the number of detected photons increases, because the ratio of the standard deviation in the signal to the signal goes as $\sqrt{N}/N=1/\sqrt{N}$. Although there may be many sources of intensity noise, the limit set by photon noise can never be overcome; however, the significance of photon noise can be reduced by increasing the number of photons collected by the detector. The number of photons collected can be increased by increasing the intensity of the light source, the efficiency of the detector, and/or the throughput of components of the optical relay structure, such as the beamsplitter, among others.

Photon noise creates noise in luminescence polarization assays. To a very good approximation, the noise in the polarization is proportional to the noise in the luminescence intensities from which the polarization is calculated and corresponds to seven mP standard deviation in polarization for every one percent standard deviation in intensity. This relationship essentially is independent of the degree of polarization. Photon noise puts a premium on simply collecting enough light, especially in rapid high-throughput screening measurements using the optically restrictive microplate format. For additional information, see the calculation in U.S. Provisional patent application Ser. No. 60/063,811, which is incorporated herein by reference.

Most well-developed polarization assays have maximum polarization changes of between 100 mP and 200 mP, so acceptable standard deviations in the polarization should be no greater than about 5 mP to 10 mP. This requires detection of at least 10,000 photons per intensity measurement to reduce intensity noise to about 1%. The inefficiency of polarization optical systems increases the problem. The number of photons collected is proportional to both the concentration and the detection time, leading to trade-offs between probe concentration and screening throughput. High concentrations of reagents not only are expensive, but also produce insensitive binding assays if they exceed the dissociation constant of the binding reaction.

Figure 10:
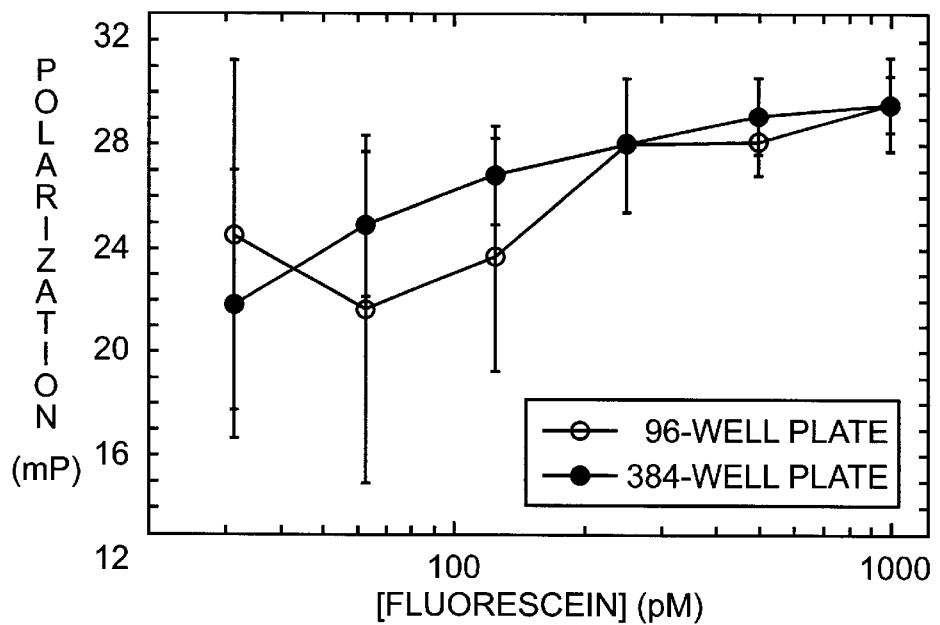
FIG. 10 is a graph of polarization versus fluorescein concentration measured in 96-well and 384-well microplates, showing the sensitivity of the apparatus.
Figure 11:
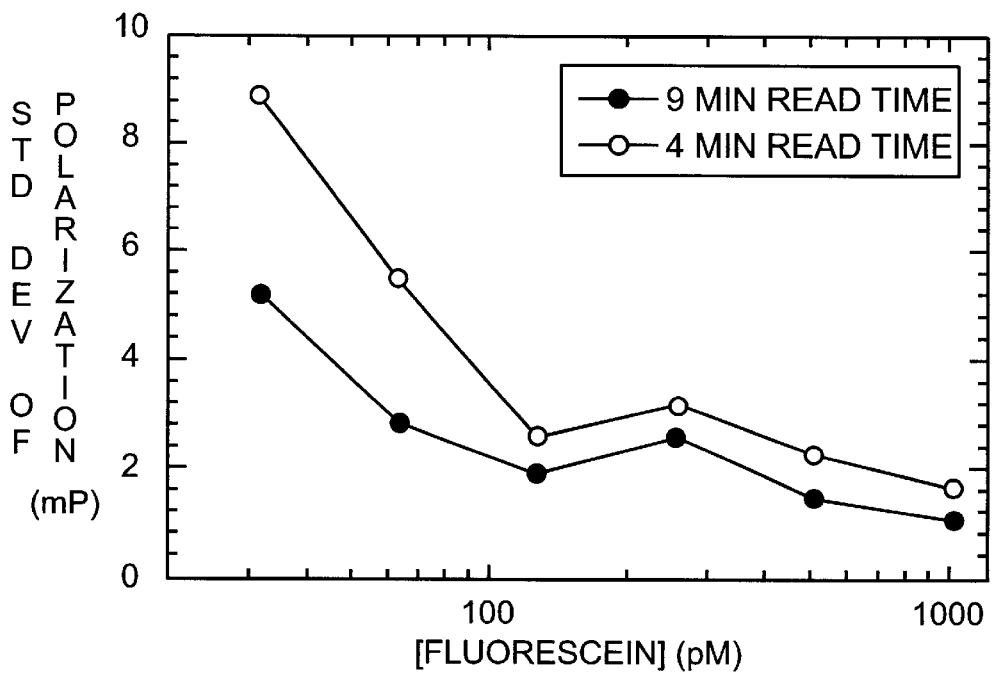
FIG. 11 is a graph of the standard deviation of polarization versus fluorescein concentration measured in 384-well microplates, determined after 4-minute and 9-minute whole microplate read times, showing the sensitivity of the apparatus.

FIGS. 10–11 show results that characterize a luminescence polarization apparatus constructed in accordance with the invention. Data were collected at room temperature using the preferred apparatus shown in FIGS. 4–9.

FIG. 10 is a graph showing polarization in a serial dilution of fluorescein in 96- and 384-well microplates. The graph demonstrates that the polarization of fluorescein can be measured with adequate accuracy and precision down to, or below, 100 pM, because the measured value is substantially independent of concentration down to, or below, this concentration.

FIG. 11 is a graph showing the noise (or standard deviation) in polarization in a serial dilution of fluorescein in 384-well microplates. As described above, noise below 5–10 mP is sufficiently small for most practical polarization assays. Good precision may be obtained at subnanomolar label concentrations in rapidly scanned 384-well microplates, and even better precision may be obtained in more slowly scanned microplates. The size of the error bars shows that the number of photons collected by the detector exceeds 10,000 in 100 milliseconds from a 100 picomolar fluorescein solution at pH 7.5.

5. Description of Preferred Light Sources

Photon noise can be reduced by using a sufficiently high-intensity light source, such as a continuous high color temperature xenon arc lamp or a laser, among others, as described above. The following table compares the preferred continuous and time-varying light sources used in apparatus 90 and 260.

| Summary | Continuous Light Source | Flash Lamp Light Source | Comparison (Flash/Continuous) |
|---|---|---|---|
| Life of light source | 300 hrs | 10,000 hrs | 6% |
| Total power of light source | 13,000 mW | 830 mW | 5% |
| Visible power (390–770 nm) | 5100 mW | 230 mW | 3% |
| Infrared power(>770 nm) | 7300 mW | 190 mW | 11% |
| Ultraviolet power (300–390 nm) | 620 mW | 68 mW | 4% |
| Apparatus power (485 nm) | 7.1 mW | 0.29 mW | 4% |
|  | $1.7 \times 10^{16}$ photons/sec | $7.1 \times 10^{14}$ photons/sec |  |

-continued

| Summary | Continuous Light Source | Flash Lamp Light Source | Comparison (Flash/ Continuous) |
|---|---|---|---|
| Photons/sec from a 1 nM luminophore solution (estimated) | $1 \times 10^8$ photons/sec | $5 \times 10^6$ photons/sec | 5% |
| Photons/sec from a 10 pM luminophore solution (estimated) | $1 \times 10^6$ photons/sec | $5 \times 10^4$ photons/sec | 5% |

The lifetime of the continuous lamp is only 1/33 the lifetime of the flash lamp. The lifetime of the continuous lamp was taken directly from the manufacturer's specifications. The lifetime of the flash lamp was computed using the manufacturer's specification. Specifically, the flash lamp is run at 100 flashes per second, using 250 mJ of electrical power per flash; at this power level, the lifetime of the flash lamp is rated at $1 \times 10^{9}$–$1 \times 10^{10}$ flashes, corresponding to a lifetime of about 10,000 hours ($5 \times 10^9$ flashes/[100 flashes/sec×3600 sec/hour]).

The continuous lamp provides about 20 times more light than the flash lamp. The total optical power of the continuous lamp (collected by a F/1.0 optical system) is 13 W over the wavelength range 300–4000 nm. The total optical power of the flash lamp (collected by a F/1.0 optical system) is 830 mW over the wavelength range 100–4000 nm. The total optical power of the flash lamp was derived from the electrical energy, the electrical-to-optical conversion efficiency, the optical collection efficiency, and the repetition rate (250 mJ×50%×6.6%×100 Hz). The optical powers of the different spectra of the flash lamp were derived by multiplying the total optical power of the flash lamp by the fraction of the power in each wavelength range, i.e., ultraviolet (300–390 nm) 8.3%, visible (390–770 nm) 28%, and infrared (770+nm) 24%.

The optical power in the preferred apparatus was determined after passage through a bandpass filter (center 485 nm, bandwidth 20 nm). The optical power in photons per second was calculated by assuming that all photons had a wavelength of 485 nm (energy=1240 eV×nm/wavelength).

High-throughput screening requires that light be collected quickly and efficiently, so that assays can be accurately and rapidly performed. A 1% error in intensity, corresponding to a 7 mP error in polarization, requires collection of at least 10,000 photons, as described above. For high-throughput screening, these photons should be collected within 100 ms, corresponding to a collection rate of 100,000 photons/sec. Both lamps produce more than 100,000 photons/sec, but the criterion is to collect 100,000 luminescence photons/sec, not to produce 100,000 excitation photons/sec. Specifically, the criterion is to count at least 10,000 photons in 100 msec ($1 \times 10^5$ photon/sec) for low concentrations of luminophore (less than 1 nM). The preferred apparatus achieves this photon limit at roughly 10–100 pM for polarization assays.

The detection efficiency is given by the product of an emission efficiency, a collection efficiency, a transmission efficiency, and a detector quantum efficiency, as calculated below.

The emission efficiency is determined by a product of the fractional absorption and quantum yield. The fractional absorption is determined by the Beer-Lambert law, $-\log[I/I_0] = \epsilon cL$ where I is transmitted intensity, $I_0$ is incident intensity, $\epsilon$ is extinction coefficient, c is concentration, and L is path length. The molar extinction coefficient of typical luminophores is about 50,000 per molar per centimeter, and the path length in typical microplates is about 5 mm. Thus, the fraction of photons absorbed is about $6 \times 10^{-5}$ in a 1 nM solution and about $6 \times 10^{-7}$ in a 10 pM solution. The quantum yield (ratio of photons emitted to photons absorbed) of typical luminophores is 0.9, so that about $5 \times 10^{-5}$ of the incoming photons are converted to luminescence emission photons (at 1 nM). This is effectively the emission efficiency.

The collection efficiency is determined by numerical aperture. Luminescence is emitted over all angles, whereas luminescence is collected over limited angles. Specifically, luminescence is collected over a cone angle θ given by the formula $\theta = 2\arcsin[(NA)/n)]$, where NA is numerical aperture and n is index of refraction. The optical collection efficiency is about 3% for an NA of 0.39 and about 1% for an NA of 0.22.

The transmission efficiency is determined by the optics through which the light passes between the sample and detector. The transmission efficiency in the preferred apparatus probably is about 2%.

The detector quantum efficiency is determined by the detector. The detector quantum efficiency of the photomultiplier tube (PMT) in the preferred apparatus typically is 20–25%.

Thus, the overall detection efficiency assumes values as follows:

| Concentration | Detection Efficiency (Estimated) |
|---|---|
| 1 nM | $5 \times 10^{-5} \times 0.03 \times 0.02 \times 0.25 = 8 \times 10^{-9}$ |
| 10 pM | $5 \times 10^{-7} \times 0.03 \times 0.02 \times 0.25 = 8 \times 10^{-11}$ |

To determine if the continuous and/or flash lamps satisfy the collection criterion of 100,000 photons per second, the detection efficiency was multiplied by the excitation flux to yield an estimated measurable flux at 1 nM and 10 pM (measured in photons/sec). The estimated measurable flux shows that the continuous lamp fails the criterion of 100,000 photons per second somewhere below 10 pM for a typical luminophore, whereas the flash lamp fails the criterion somewhere near 200 pM (roughly 20 times higher). Thus, the continuous lamp satisfies the collection criteria, whereas the flash lamp does not. Specifically, the flash lamp has enough optical power to make statistically significant measurements at 1 nM, but not at 10 pM, where it leads to the collection of fewer than $1 \times 10^5$ photons/sec.

In summary, the continuous lamp has a power of greater than 1 watt over the visible wavelength range of 390 to 770 nm, and is sufficient to reduce photon noise to less than 1 percent of a light signal emitted from a 100 picomolar fluorescein solution at pH 7.5.

6. Description of Microplates

FIGS. 12–24 show microplates for supporting samples for luminescence assays in a plurality of wells or assay sites. These microplates differ in their well shape, well size, and well density, among other parameters. The remainder of this section describes microplates constructed in accordance with aspects of the invention, including (A) 96-well microplates, (B) 384-well microplates, (C) 1536-well microplates, and (D) miscellaneous microplates.

A. 96-Well Microplates

FIG. 12 is a top view of a 96-well microplate 200 constructed in accordance with aspects of the invention. Microplate 200 includes a frame 202 and a plurality of sample wells 204 disposed in the frame. In some embodiments, microplate 200 may include one or more reference fiducials 206 disposed in the frame.

Frame 202 is the main structural component of microplate 200. The frame may have various shapes and various dimensions. In microplate 200, frame 202 is substantially rectangular, with a major dimension X of about 127.8 mm and a minor dimension Y of about 85.5 mm. Frame 202 may be adapted for ease of use and manufacture. For example, frame 202 may include a base 208 to facilitate handling and/or stacking, and frame 202 may include notches 210 to facilitate receiving a protective lid. Frame 202 may be constructed of a material, such as a thermoplastic, that is sturdy enough for repeated, rugged use and yet minimally photoluminescent to reduce background upon illumination.

Frame 202 includes a sample well region 212 and an edge region 214 forming a perimeter 216 around the sample well region. Sample wells may be disposed in the sample well region in various configurations. In microplate 200, sample wells 204 are disposed in sample well region 212 in a substantially rectangular 8×12 array, with a pitch (i.e., center-to-center interwell spacing) along both X and Y of about 9 mm. This pitch corresponds to a density of wells of about one well per 81 mm$^2$.

Reference fiducials 206 may be used for identification, alignment, and/or calibration of the microplate. Reference fiducials may be disposed in the sample well region and/or the edge region in various configurations. In microplate 200, reference fiducials 206 are disposed in edge region 214, substantially aligned with a row of sample wells along the X dimension. Reference fiducials preferentially are positioned in corners of the microplate, near where optical analysis begins, so that they may quickly be identified and analyzed. Reference fiducials may be positioned in rotationally symmetric positions, so that microplates may be loaded into an optical device and analyzed backwards without difficulty. Further aspects of reference fiducials are described in U.S. patent application Ser. No. 09/156,318 and PCT patent application Ser. No. PCT/US99/08410, which are incorporated herein by reference.

FIG. 13 is a cross-sectional view of microplate 200, showing sample wells 204, reference fiducial 206, and base 208. In microplate 200, frame 202 has a top 218, a substantially parallel bottom 220, and substantially perpendicular sides 222. Top 218 may have various shapes, although it typically is flat. (Top 218 may be surrounded by a raised edge to facilitate stacking.) Frame 202 has a height H of about 12 mm, corresponding generally to the separation between top 218 and bottom 220. This height is large enough to facilitate handling by sample handlers and/or a stage, and yet small enough to permit optical analysis of the entire well. Sample wells 204 are disposed with open, optically transparent ends 224 directed toward top 218, and closed, optically opaque ends 226 directed toward bottom 220. In some embodiments, optically opaque ends 226 may be replaced by optically transparent ends to permit bottom illumination and/or detection. Reference fiducial 206 is disposed on top 218, although reference fiducials also may be disposed on bottom 220 and/or sides 222.

FIG. 14 is a first enlarged portion of the cross-sectional view in FIG. 13, showing details of sample wells 204. Sample wells may have various shapes and various dimensions, as described in detail in subsequent sections. In microplate 200, sample wells 204 are substantially frusto-conical, with substantially straight side walls 228 and a substantially flat bottom wall 230. In microplate 200, optically opaque ends 226 are positioned about 6.7 mm below top 218, and about 5.3 mm above bottom 220. Sample well 204 is characterized by a top diameter $D_{T,96}$, a bottom diameter $D_{B,96}$, a height $H_{96}$, and a cone angle $\theta_{96}$. Here, $\theta_{96}$ is the included angle between side walls 228. In microplate 200, $D_{T,96}$ is about 4.5 mm, $D_{B,96}$ is about 1.5 mm, $H_{96}$ is about 6.7 mm, and $\theta_{96}$ is about 25.4°. Sample well 204 has a total volume of about 50 μL, and a smallest practical working volume of about 1–20 μL.

FIG. 15 is a second enlarged portion of the cross-sectional view in FIG. 13, showing details of reference fiducial 206. Reference fiducials may have various shapes and various dimensions, as described in detail in subsequent sections. In microplate 200, reference fiducial 206 is substantially frusto-conical, with substantially straight side walls 232 and a substantially flat bottom wall 234. Reference fiducial 206 is characterized by a top diameter $D_{T,RF,96}$, a bottom diameter $D_{B,RF,96}$, a height $H_{RF,96}$, and a cone angle $\theta_{RF,96}$. Here, $D_{B,RF,96}$ and $\theta_{RF,96}$ are substantially equal to $D_{B,96}$ and $\theta_{96}$, the corresponding values for sample well 204. $H_{96}$ is about 1 mm, and $D_{T,RF,96}$ is specified by the other parameters.

B. 384-Well Microplates

FIGS. 16–19 are views of a 384-well microplate 300 constructed in accordance with aspects of the invention. Microplate 300 is similar in many respects to microplate 200 and includes a frame 302 and a plurality of sample wells 304 disposed in a sample well region 312 of the frame. In some embodiments, microplate 300 may include one or more reference fiducials 306 disposed in an edge region 314 or other region of the frame.

The external dimensions of microplate 300 are similar to the external dimensions of microplate 200. However, the density of sample wells in microplate 300 is four times higher than the density of sample wells in microplate 200. Consequently, the pitch (i.e., the center-to-center interwell spacing) in microplate 300 is about 4.5 mm, or about one-half the pitch in microplate 200. This pitch corresponds to a density of wells of about four wells per 81 mm$^2$. In microplate 300, reference fiducial 306 is positioned about midway between two rows of sample wells along the X direction; in contrast, in microplate 200, reference fiducial 206 is positioned about in line with a row of sample wells along the X direction. This is because the reference fiducials are positioned in approximately the same position in each microplate, but the center line of one row of sample wells in microplate 200 because the center line between two rows of sample wells in microplate 300 as the density of wells is quadrupled.

Sample wells 304 in microplate 300 are similar to sample wells 204 in microplate 200. Sample wells 304 may be characterized by a top diameter $D_{T,384}$, a bottom diameter $D_{B,384}$, a height $H_{384}$, and a cone angle $\theta_{384}$. The preferred values of $D_{B,384}$ and $\theta_{384}$ for microplate 300 are substantially similar to the preferred values of $D_{B,96}$ and $\theta_{96}$ for microplate 200. However, the preferred value for $D_{T,384}$, which is about 4.7 mm, is smaller than the preferred value for $D_{T,384}$, which is about 6.7 mm. In microplate 300, the upper diameter must be smaller than the upper diameter of the sample wells in microplate 200, because the sample wells are close packed, leaving no more interwell spacing than necessary for moldability. In turn, the preferred value for $H_{384}$ is about 4.7 mm, so that the wells are elevated by about 7.3 mm. Sample well 304 has a total volume of about 25 µL, and a smallest practical working volume of about 1–12 µL.

Reference fiducial 306 in microplate 300 may be essentially identical to reference fiducial 206 in microplate 200.

C. 1536-Well Microplates

FIGS. 20–24 are views of a 1536-well microplate 350 constructed in accordance with aspects of the invention. Microplate 350 is similar in many respects to microplates 200 and 300, and includes a frame 352 and a plurality of sample wells 354 disposed in the frame. The pitch in microplate 350 is about 2.25 mm, or about one-half the pitch in microplate 300 and about one-fourth the pitch in microplate 200. This pitch corresponds to a density of wells of about sixteen wells per 81 mm².

Sample wells 354 may be exclusively frusto-conical, like sample wells 204 in microplate 200 and sample wells 304 in microplate 300. However, due to spatial constraints, the volume of such wells would have to be small, about 1–2 µL. Alternatively, sample wells 354 may have a frusto-conical lower portion 306 coupled to a cylindrical upper portion 308. The volume of such wells may be larger, for example, about 7–8 µL. The larger wells permit use of smaller or larger sample volumes. Larger sample volumes may be useful if the microplate is used in conjunction with standard fluid dispensing equipment, or if reagents are to be added to the well from stock solutions, such as 100X DMSO or DMF stock solutions.

Reference fiducials in microplate 350 may be essentially identical to reference fiducials 206 in microplate 200 and reference fiducials 306 in microplate 300.

D. Miscellaneous Microplates

The invention also may provide additional new microplate designs that are useful for high-efficiency sample analysis in luminescence polarization assays. These designs include:

(i) A microplate having a frame portion and a top portion, where an array of wells is formed in the top portion. The wells are organized in a density of at least about 4 wells per 81 mm². Each well has a bottom wall that is elevated at least about 7 millimeters above a plane defined by a bottom edge of the frame.

(ii) A microplate having an array of conical wells organized in a density of at least about 4 wells per 81 mm².

(iii) A microplate having an array of conical wells, where each well has a maximum volume capacity of less than about 55 microliters. A preferred small-volume well design has a volume capacity of 1–20 microliters.

(iv) A microplate having an array of wells in the top portion, where each well has a maximum volume capacity of less than about 55 microliters and a well bottom that is elevated at least about 7 millimeters above a plane defined by a bottom edge of the frame.

(v) A microplate having an array of wells in a top portion, organized in a density of at least about 4 wells per 81 mm², where each well has a conical portion characterized by a cone angle of at least about 8°.

(vi) A microplate having an array of conical wells characterized by a cone angle θ, where θ=2 arcsin (NA/n) and NA is equal to or greater than about 0.07.

(vii) A microplate having an array of wells organized in a density of at least about 16 wells per 81 mm², where each well has a frusto-conical bottom portion and a substantially cylindrical upper portion.

(viii) A microplate comprising a frame and a plurality of frusto-conical sample wells disposed in the frame, where the sample wells are characterized by a cone angle of at least about 8°. The microplate further may include a reference fiducial that provides information to facilitate sample analysis.

7. Application of Sensed Volumes

The invention provides a system for detecting light transmitted from a sensed volume. The system comprises (1) an optical device capable of detecting light substantially exclusively from a sensed volume, and (2) a sample holder configured to support a sample so that the shape of the sample conforms to the shape of at least a portion of the sensed volume. The sample holder may be a sample well in a microplate and may have a conical or frusto-conical shape, so that the sample conforms to a portion of an hourglass-shaped sensed volume.

Figure 25:
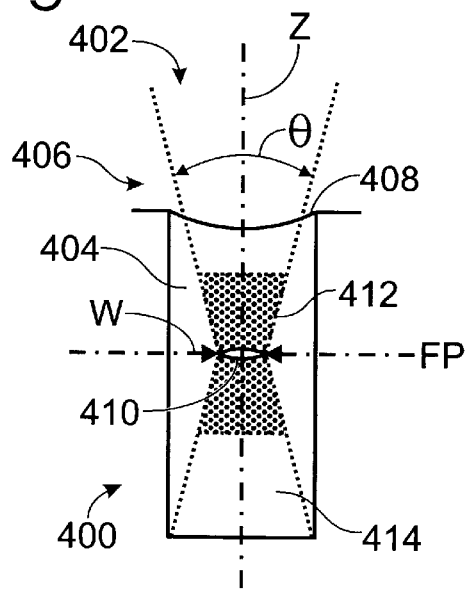
FIG. 25 is a partially schematic cross-sectional view of a standard microplate well.

FIG. 25 is an enlarged cross-sectional view of a standard cylindrical or square microplate well 400, showing air 402 above the sample well, a sample 404 within the sample well, and a light beam 406 passing through the sample well. The interface between air 402 and sample 404 is termed a meniscus 408 and may be convex, plan, or concave.

Light beam 406 is created by an optical device, such as luminescence apparatus 90 described above. The optical device focuses the light so that the light beam has an hourglass shape along a cone or optical axis Z. Light beam 406 is narrowest at its "waist" 410, which has a diameter W and which is located in a focal plane FP of the optical device. Light beam 406 increases in width monotonically above and below waist 410, having a total included angle θ. Angle θ is the cone angle of the "maximum cone" defined by the "marginal rays" of the optical device, and is twice the angle between the marginal rays and the optical axis Z. The marginal rays trace the path of the most outlying light rays normally detectable by the system. The maximum cone defines the outer boundary of the hourglass-shaped light beam and is the volume into which light may be delivered and from which light may be transmitted by the optical device. Angle θ also is the angle subtended at focal plane FP by the light-gathering components (e.g., the objective lens) of the optical device.

Values of W and θ depend on components and properties of the optical device and may be varied by varying these components. For example, cone angle θ is given by the formula θ=2 arcsin(NA/n), where "NA" is the numerical aperture of the optical device, and "n" is the index of refraction of the medium adjacent the optical device. Generally, the numerical aperture lies in the range 0.07–1.4, with a preferred range of 0.1 to 0.5 and a preferred value of NA=0.22, corresponding to the numerical aperture of a low-luminescence fused-silica fiber optic cable. The value NA=0.22 is a good compromise, creating a sensed volume that fits into sample wells in a 384-well microplate without hitting walls, and creating a sensed volume that can read to the bottom of microplates conforming to Society of Biomolecular Screening size standards. Generally, the index of refraction lies in the range 1.0–1.6, with a preferred value of n=1.0 corresponding to the index of refraction of air. The preferred numerical aperture and preferred index of refraction correspond to a cone angle of about 25.4°.

The portion of the hourglass to which light may be delivered and from which light may be transmitted further may be limited by one or more confocal optics elements within the optical device. Such confocal optics elements may include apertures placed in image planes of the optical device, conjugate to focal plane FP.

The maximum cone and the confocal optics elements combine to create a sensed volume 412. The shape of sensed volume 412, indicated in FIG. 25 by stippling, may differ in directions parallel and perpendicular to the optical axis Z. Parallel to optical axis Z, the shape may be a Lorentzian, among others. Perpendicular to optical axis Z, the shape may be a Gaussian, or it may be a rounded pulse function, among others. A laser beam might give rise to a Gaussian, whereas a fiber optic bundle might give rise to a rounded pulse function. Generally, lower numerical apertures will create sensed volumes shaped more like cylinders, whereas higher numerical apertures will create sensed volumes shaped more like hourglasses.

Outside the hourglass-shaped beam and sensed volume 412 are optically inaccessible regions 414, from which luminescence is neither excited nor detected. Sample in these regions effectively is wasted, because it does not contribute to the signal. To reduce such waste, the shape and volume of the sample holder may be chosen or designed to conform to the shape and volume of the sensed volume.

Figure 26:
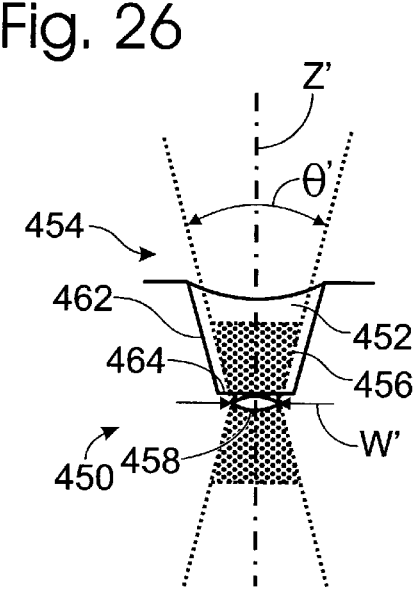
FIG. 26 is a partially schematic cross-sectional view of a sample holder constructed in accordance with the invention.

FIG. 26 is a partially schematic cross-sectional view of a sample holder 450 constructed in accordance with the invention. Sample holder 450 supports a sample 452 illuminated by a light beam 454 forming a sensed volume 456. Sensed volume 456 is shaped substantially like an hourglass, having a waist 458 with diameter W' and conical margins 460 characterized by a cone angle 74 ' and a cone or optical axis Z'.

Sample holder 450 is configured to support sample 452 so that the shape of the sample conforms to the shape of at least a portion of sensed volume 456. Light is delivered to a sensed volume of the sample from a light source, and transmitted from a sensed volume to a detector. Here, sample holder 450 has a frusto-conical shape configured to conform to substantially one-half of the hourglass shape of sensed volume 456. Specifically, sample holder 450 has conical wall portions 462 that substantially conform to conical margins 460 of sensed volume 456, and a planar bottom portion 464 that substantially conforms to waist 458 of sensed volume 456. For example, the cone angle associated with conical margins 462 substantially equals cone angle θ' of sensed volume 456. In other embodiments, the sample holder may have a purely conical shape or an hourglass shape, so that it conforms to a larger portion of the sensed volume. In yet other embodiments, the sample holder may have yet other shapes, to conform to alternatively shape sensed volumes. Optically inaccessible regions within sample holder 450 are reduced, so that most of the sample contributes to the analysis, reducing sample waste.

Figure 27:
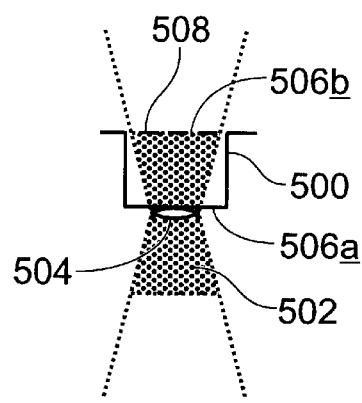
FIG. 27 is a partially schematic cross-sectional view of an alternative sample holder constructed in accordance with the invention.

FIG. 27 is a partially schematic cross-sectional view of an alternative sample holder 500 constructed in accordance with the invention. Sample holder 500 is configured to match substantially half of an hourglass-shaped sensed volume 502. Sample holder 500 is dimensioned so that the waist 504 of the sensed volume may be aligned with the bottom 506a of the sample holder, with the top 508 of the sensed volume substantially aligned with the top 506b of the sample holder. This embodiment may be especially useful for very small sample volumes, such as may be used in 1536-well microplates, because it may increase the sample volume to an amount that may be handled and dispensed more easily.

Figure 28:
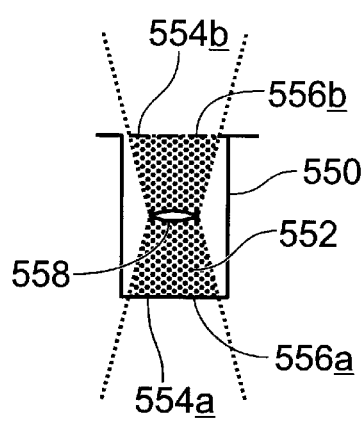
FIG. 28 is a partially schematic cross-sectional view of another alternative sample holder constructed in accordance with the invention.

FIG. 28 is a partially schematic cross-sectional view of another alternative sample holder 550 constructed in accordance with the invention. Sample holder 550 is configured to match substantially all of an hourglass-shaped sensed volume 552. Sample holder 550 is dimensioned so that the bottom and top 554a,b of the sensed volume may be aligned with the bottom and top 556a,b of the sample holder, with the waist 558 of the sensed volume substantially in between. This embodiment also may be especially useful for very small sample volumes.

Preferred sample wells are chosen to optimize lower detection limit, signal-to-noise ratio, and signal-to-background ratio, and to minimize sample volume, for a given sensed volume. Lower detection limit is the lowest concentration of sample that can be measured. Signal-to-noise ratio is the signal from the sample divided by variations in the signal due to noise. Signal-to-background ratio is the signal from the sample divided by the signal from contaminants in the sample, the sample holder, and components of the optical system.

In these wells, the cone angle of the sample holder substantially conforms to the approximately 25° cone angle of the sensed volume of the ANALYST optical device. For frusto-conical wells, optimal cone angles and well bottom diameters will depend on the cone angle and waist diameter of the sensed volume. Cone angles may range from about 8° for a low (0.07) NA optical system, on up. Such cone angles significantly exceed the slight 1–2° angle introduced into molded cylindrical sample holders to permit removal of the sample holder from the molding tool. Bottom diameters may range from about 1 µm for a high NA optical system, on up, though typical values might be 1 mm or 1.5 mm.

The smallest practical working volume for frusto-conical and other sample holders is the volume for which there still is sufficient sample volume to enclose the portion of the sensed volume contained within the sample well, or at least to enclose a sufficient portion of the sensed volume to yield acceptable signal-to-noise and signal-to-background ratios.

If the apparatus is sufficiently flexible, the shape and volume of the sensed volume produced by the apparatus may be adapted like a probe to match the shape and volume of the sample holder. In this way, the sensed volume may be expanded for maximum signal in a large sample holder, and contracted to avoid nearby walls in a small sample holder.

Alternatively, the shape and volume of the sensed volume may be held constant, and the position of the sensed volume varied to match the sample holder and/or assay. In this way, the sensed volume will report on equal volumes of each composition analyzed, so that the apparatus effectively reports "intensive" quantities. Intensive quantities do not depend on the amount of composition in a sample holder; in contrast, extensive quantities do depend on the amount of composition in the sample holder. This approach can be used to facilitate comparison of results obtained from different-sized sample wells. This approach also can be used to facilitate comparison of results obtained from like-sized sample wells containing different volumes of solution.

Figures 29, 30:
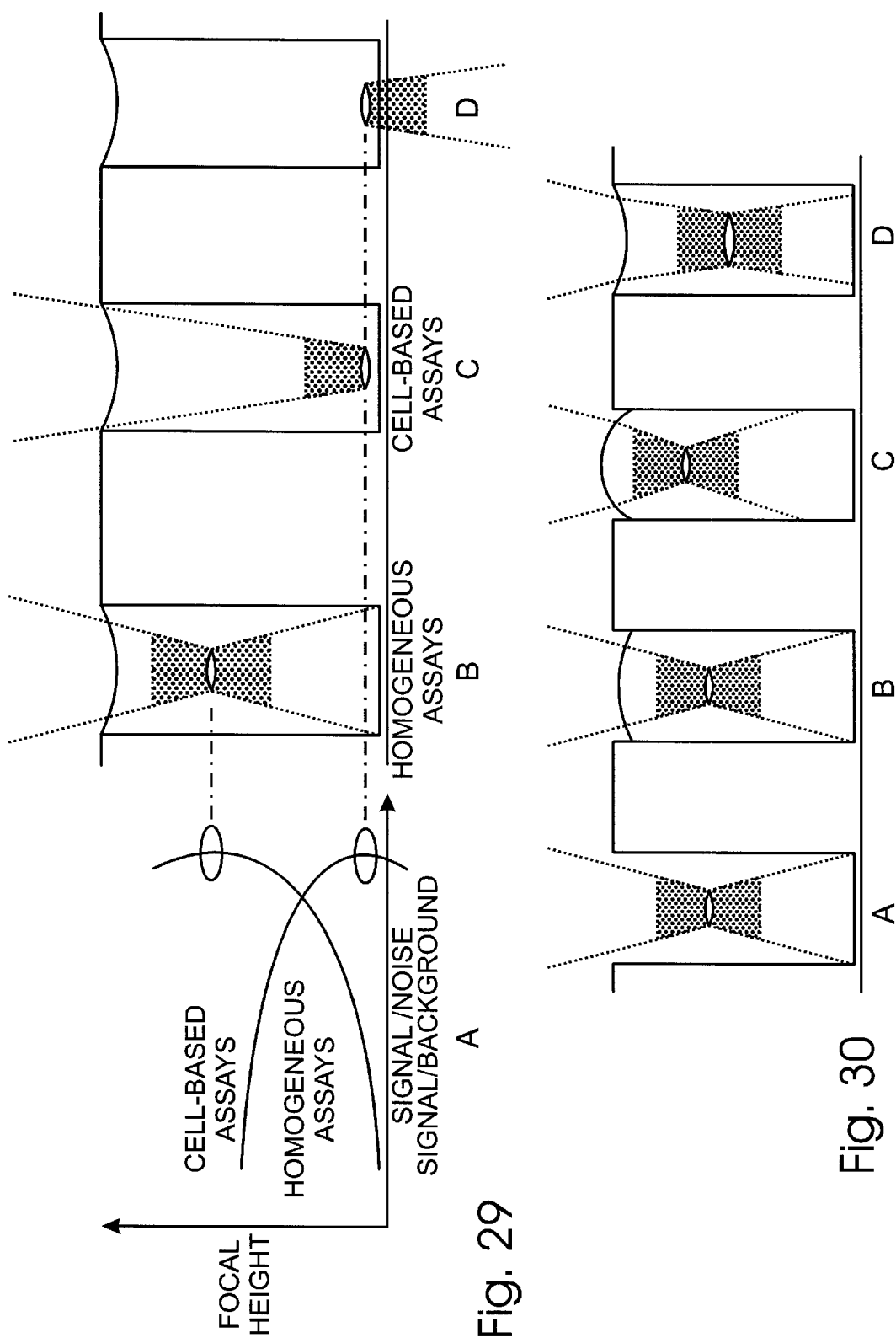
FIG. 29 is a partially schematic cross-sectional view of three sample wells, showing alternative positions of a sensed volume.
FIG. 30 is a partially schematic cross-sectional view of four sample wells, showing how the meniscus affects the shape and position of the sensed volume within a sample well.

FIG. 29 shows how the sensed volume can be directed to different regions of a standard microplate well, and how directing the sensed volume affects signal-to-noise and signal-to-background ratios.

In homogeneous assays (Panel B), photoluminescent molecules are distributed uniformly throughout the composition, and the optimum signal-to-noise and signal-to-background ratios are obtained regardless of well geometry when the sensed volume is positioned in the middle of the composition (Panel A), so that the sensed volume does not overlap with the meniscus or the bottom or sides of the well. If the meniscus is in the sensed volume, light reflected from the meniscus will be detected. This will decrease sensitivity by increasing background and decreasing signal. If the bottom of the well is in the sensed volume, light reflected from the well bottom will be detected. Moreover, noncomposition photoluminescence arising from fluorescent and other photoluminescent materials that are commonly included in the microplate or adsorbed to the walls of the microplate also will be detected. These two effects will decrease sensitivity by increasing background and decreasing signal. Luminescence measured from the microplate walls will lead to spuriously high luminescence intensities and luminescence polarizations.

In cell-based assays (Panels C and D), photoluminescent molecules are concentrated in or near cells growing at the bottom of the well, and the optimum signal-to-noise and signal-to-background ratios are obtained when the sensed-volume is centered about the bottom of the well (Panel A). Such centering may be accomplished either using top optics (Panel C) or bottom optics (Panel D).

For some cell-based assays, microplate wells having a frusto-conically-shaped portion may be particularly advantageous. The conical shape of the well tends to focus cells into a smaller area defined by the substantially flat bottom wall. The conical shape of the well and the selected confocal optics allow substantially all of the cells at the bottom of the well to be detected in the sensed volume, thus maximizing signal sensitivity and reagent utilization regardless of whether the cells are uniformly distributed across the bottom of the well. The conical geometry of the wells also makes it possible to perform cell-based assays from the top without requiring transmission of light through the bottom wall of the well. The geometry is also useful for performing fluorescence polarization assays which may be based on receptor/ligand binding to the bottom of the well.

The shape and position of the sensed volume within the well may be affected by (1) the meniscus and (2) the geometry of the sample well, among other factors.

FIG. 30 shows how the meniscus affects the shape and position of the sensed volume within a sample well. The meniscus affects the sensed volume because light is refracted as it crosses the meniscus boundary between the air and the composition. Specifically, light passing from air (with its lower index of refraction) into the sample (with its higher index of refraction) bends toward the normal, as described by Snell's law. Here, the normal is the direction perpendicular to the surface of the meniscus at a given point. If there is no fluid and hence no meniscus, the beam has a nominal undistorted shape (Panel A). If the meniscus is everywhere perpendicular to the light beam, then light passing through the meniscus will not bend, and the beam will retain its nominal undistorted shape (Panel B). For a converging beam, this will occur when the meniscus is appropriately convex. If the meniscus is more than appropriately convex, light will bend toward the middle of the well as it passes through the meniscus, and the sensed volume will be compressed and raised (Panel C). If the meniscus is less than appropriately convex, flat, or concave, light will bend away from the middle of the well as it passes through the meniscus, and the sensed volume will be stretched and lowered (Panel D).

Sample wells can be configured to account for these changes in the shape and position of the sensed volume created as excitation and emission light passes through the meniscus. The invention includes shaping the sample well to account for changes in the shape and position of the sensed volume, and shaping and treating the sample well to alter the shape of the meniscus, as appropriate.

Figure 31:
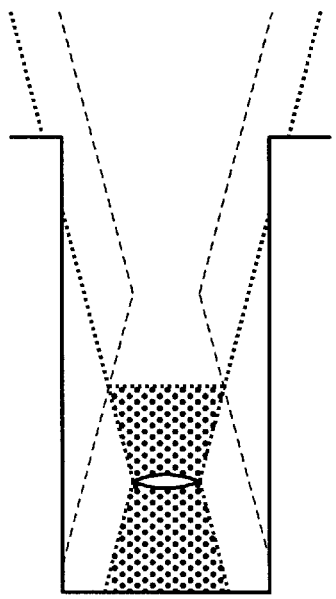
FIG. 31 is a partially schematic cross-sectional view of a sample well, showing how the geometry of the sample well affects the position of the sensed volume.
Figure 32:
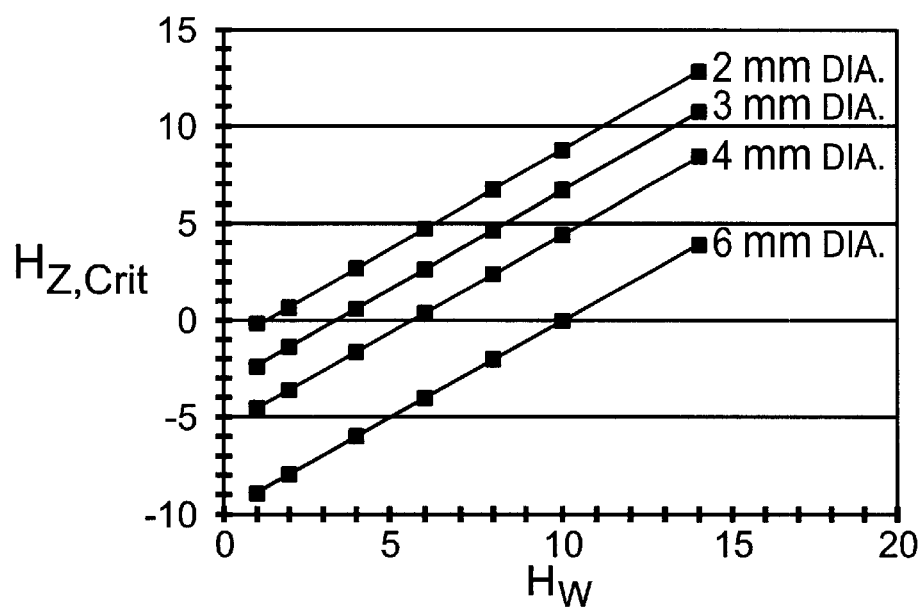
FIG. 32 is a graph showing the relationships between critical Z-height and microplate well height.

FIGS. 31 and 32 show how the geometry of the sample well affects the position of the sensed volume. In particular, if the well is sufficiently narrow relative to the diameter of the beam, or if the well is sufficiently deep relative to the angle made by the beam, then the light beam may impinge upon the top walls of the well. In these cases, setting the Z-height too low can reduce sensitivity (1) by decreasing the desired signal because less light enters the well, and (2) by increasing the background because the light beam illuminates the tops of wells. Many microplates are made from materials that are fluorescent or otherwise photoluminescent, and the instrument will detect this photoluminescence from materials at the tops of wells.

Because beam position is a critical determinant of signal to noise, Z height must be appropriately maintained; Z height should be kept above a critical focal height, $H_{Z,Crit}$ The height at which the beam first impinges on the walls of the well is the critical focal height, $H_{Z,Crit}$. FIG. 32 shows how $H_{Z,Crit}$ depends on the well height $H_W$ and well diameter $D_W$, for a beam of diameter 1.5 millimeters (mm) and a beam angle 25.4°. Similarly, Table 1 shows how $H_{Z,Crit}$ depends on well height and well diameter for four commercially available microplates.

| Plate Type | Well Height (mm) | Well Diameter (mm) | $H_{Z,Crit}$ (mm) |
| --- | --- | --- | --- |
| Costar Black Flat Bottom 96-Well 3915 | 10.71 | 6.71 | −0.85 |
| Dynatech MicroFluor Round Bottom | 9.99 | 6.78 | −1.72 |
| Costar Black 384-Well 3710 | 11.55 | 3.66 | 6.76 |
| Packard White 384-Well #6005214 | 11.57 | 3.71 | 6.67 |

The increase in $H_{Z,crit}$ shows that for a microplate having a standard height and XY area, as the aspect ratio (length/diameter) and density of wells increases, the ability of a confocal optic system to read small volumes in standard straight-walled wells decreases. This may require reading through the bottom of the well for cell-based assays, which is not always convenient or practical.

Z-height can be optimized for a particular microplate and assay by (1) preparing a test microplate with representative assay (e.g., blanks, positive and negative controls, dilution series), (2) and reading the microplate multiple times at different Z-heights to determine the Z-height that gives the best signal-to-background data. Some combinations of assay and microplate are relatively insensitive to Z-height, while others demonstrate a distinct optimum.

8. Background Subtraction

The invention provides methods and apparatus for improving signal resolution in hybridization assays. These improvements may be obtained without using information from a blank, and/or without requiring a determination of the lifetime or intensity of the background. These improvements also may be obtained irrespective of whether a significant amount of the background is being detected by the detector at the same time that light emitted by the analyte is being detected. Consequently, the invention permits discrimination between analyte and background and/or other non-analyte emitters in measurements performed in a single sample container. The invention also permits light to be detected and analyzed continuously, so that signal is not wasted and data collection is not slowed.

A. Overview

Intensity-based method. The following intensity-based method may be used to analyze polarization results:
1. Take polarization measurements on all wells on plate.
2. Identify buffer (background) wells on plate.
3. Determine average intensities of background wells for both S and P channels.
4. Subtract average background ∥ and ⊥ channel intensities from all wells.
5. Calculate polarization for each well using G factor and background-subtracted ∥ and ⊥ intensities.

Here, step 5 is carried out using the following relation between intensity and polarization:

$$P = \frac{(I_\parallel - I_{\parallel 0}) - G(I_\perp - I_{\perp 0})}{(I_\parallel - I_{\parallel 0}) + G(I_\perp - I_{\perp 0})}, \quad (6)$$

where the ∥ and ⊥ subscripts indicate the ∥ and ⊥ intensities, respectively, and the 0 subscript indicates a background intensity.

Anisotropy-based method. A novel alternative anisotropy-based procedure also may be used to analyze polarization results. A basic difference between the intensity-based and anisotropy-based procedures is how the background is subtracted: in the intensity-based procedure, intensities are subtracted, whereas in the anisotropy-based procedure, anisotropies are subtracted. The anisotropy-based procedure may provide the following benefits: (1) a more robust method for background subtraction, and (2) insight into how hot wells affect polarization measurements, and a mechanism to address them.

Derivation of anisotropy-based method. To simplify the math, the anisotropy-based method is derived in terms of anisotropy rather than polarization, with the understanding that we can readily convert between anisotropy and polarization.

$$R = \frac{2P}{3-P}, \quad P = \frac{3R}{2+R}, \quad \frac{2}{R} = \frac{3}{P} - 1. \quad (7)$$

The underlying assumption for this analysis is that the assay system can be decomposed into two components: (1) the label of interest, and (2) everything else, which is lumped together as background. This typically would include autoluminescence from the microplate or other substrate and from the optical elements of the light detection device. (The same assumption is used in the intensity-based background-subtraction analysis.) The average anisotropy for the system is then given by the following expression:

$$R_T = f_L R_L + f_0 R_0 \quad (8)$$

where the multiplier f indicates the fractional intensity of a given component, and the subscripts T, L, and 0 indicate total, label of interest, and background, respectively. Solving for the anisotropy of the label of interest and invoking the relationship $f_L = 1 - f_0$ yields:

$$R_L = \frac{R_T - f_0 R_0}{f_L} = \frac{R_T - f_0 R_0}{1 - f_0}, \quad (9)$$

The preceding equation indicates that background can be subtracted by manipulating anisotropies rather than intensities. The anisotropy of the label ($R_L$) can be estimated from the total anisotropy ($R_T$) if the background anisotropy ($R_0$) and background relative intensity ($f_0$) are known.

Before proceeding, it is instructive to review typical values for the parameters in this equation. $R_L$ depends on the label of interest; for free fluorescein in PBS, it is about 0.02 (27 mP), and for the antibody-bound tracer in the TKX™ assay kit marketed by LJL BioSystems, it is about 0.1 (140 mP). $R_0$ can range from about 0.400 (500 mP) for PBS in black plates to less than about 0.015 (22 mP) for white plates. $f_0$ has an absolute range of 0.0 to 1.0, but will be small in most applications. For instance, in the TKX assay, the average background intensity is typically about 0.006. In the fluorescein dilution series used to test the light detection device presented above, the buffer wells are roughly the same brightness as 6 pM fluorescein, so that $f_0$ is about 0.06 when compared with our performance specification of 100 pM.

A potential advantage of the anisotropy-based procedure is that it may be more robust than the intensity-based procedure. If intensities vary for some reason, such as a change in lamp power or alignment, the intensity-based background-subtraction procedure may give erroneous results. However, the anisotropy-based background-subtraction procedure will still give correct results because the background anisotropy and relative background intensity should remain unchanged.

Propagation of error. We want to be sure that anisotropy-based background subtraction does not introduce unacceptably high errors into our results. Error propagation can be estimated by $$\Delta R_L = \sqrt{\left(\frac{1}{1-f_0}\right)^2 (\Delta R_T)^2 + \left(\frac{f_0}{1-f_0}\right)^2 (\Delta R_0)^2 + \left(\frac{R_T - R_0}{(1-f_0)^2}\right)^2 (\Delta f_0)^2} \quad (10)$$

For small $f_0$, this simplifies to $$\Delta R_L = \sqrt{(\Delta R_T)^2 + f_0^2 (\Delta R_0)^2 + (R_T - R_0)^2 (\Delta f_0)^2} \quad (11)$$

This equation shows that:
1. Errors in $R_T$ (instrument errors) translate directly into errors in $R_L$.
2. Errors in the background anisotropy have only a small effect on our determination of $R_L$; for instance, if $f_0$ is 0.01 and $\Delta R_0$ is 0.1 (150 mP), the effect on $R_L$ is <0.001 (1.5 mP).
3. Errors in $f_0$ (hot wells) give appreciable errors in $R_L$ whenever $R_T$ and $R_0$ are significantly different. For instance, if $R_T = 0.1$, $R_0 = 0.4$ and $\Delta f_0 = 0.1$, the error in $R_L$ is <0.03 (45 mP).

Note that $\Delta R_L$ skyrockets when the background is bright. For instance, if the background and label have equal brightness ($f_0 = 0.5$), then $$\Delta R_L = \sqrt{(2\Delta R_T)^2 + (\Delta R_0)^2 + (R_T - R_0)^2 (4\Delta f_0)^2} \quad (12)$$

This may explain why the current lower-detection limit (LDL) of the fluorescein polarization is about 30 pM; because the background has a brightness of about 6 pM, the errors begin to accumulate as we approach this concentration.

Application: treated plates for control of hot wells in polarization. Assume that we can fabricate or treat microplates in such a way that their background anisotropy is controllable. For instance, we could add some titanium dioxide to a black plate to cause scattering, which would reduce background polarization. Specifically, consider a plate designed to work with the TKX assay. In the TKX assay, we look for a decrease in anisotropy from a nominal value of 0.100 (140 mP) to some lower value. The plate is designed with a background anisotropy of about 0.100 (140 mP) so that it provides a background that matches the assay. Now we see from Equations 8 and 9 that all "non-hit" wells give $R_T = R_L = R_0 = 0.100$.

Next, look at the behavior of a hot well. It can be extremely bright, say $f_0 = 0.5$, but because its anisotropy is the same as background, it is not detected as a "hit," because by Equations 8 and 9 it still gives $R_T = R_L = R_0 = 0.100$. This hot-well immunity is also evidenced in Equation 12: when $R_T$ and $R_0$ are about the same, errors in $f_0$ (hot wells) do not propagate to $R_L$.

If it is not technically feasible to make microplates with controlled anisotropy, then the same effect might be achieved by adding polarized components to the assay chemistry to achieve the desired background anisotropy.

Experimental results. Six 96-well microplates were filled with PBS (250 μL/well) and read on Analyst S/N E003. The following table shows intensity and polarization data for each plate.

|  | S Channel cps | | P Channel cps | | Polarization (mP) | |
| --- | --- | --- | --- | --- | --- | --- |
| Plate | Avg | StDev | Avg | StDev | Avg | StDev |
| white plate | 616624 | 20276 | 637303 | 19092 | 8 | 14 |
| black plate 1 | 49303 | 2272 | 17369 | 1212 | 498 | 18 |
| black plate 2 | 48805 | 1257 | 16718 | 525 | 508 | 14 |
| black plate 3 | 48907 | 1471 | 16984 | 799 | 503 | 18 |
| black plate 4 | 48401 | 1122 | 16647 | 478 | 506 | 14 |
| black plate 5 | 48581 | 1484 | 16833 | 810 | 504 | 17 |

The data indicate that:

1. The background polarization of the of the black plates is very high (about 500 mP).
2. The background polarization of the of the black plates is consistent from plate to plate.
3. The background polarization of the white plate is very low.

These data indicate that background anisotropy could be measured less frequently. Moreover, the consistency in the S and P intensities suggests that a similar approach could be implemented with our current intensity-based background-subtraction methodology. That is, S and P channel background intensities could be measured less frequently than every plate.

In other experiments, the background (buffer well) intensity was compared with that of Fluorescein. Four different plates were read on 4 different Analyst units. In all cases, the brightness was similar (about 6 pM Fluorescein), even though different instruments were used.

|  | Buffer brightness (pM) | |
| --- | --- | --- |
| Unit | 96 wells | 384 wells |
| AN0085 | 4.8 | 4.0 |
| AN0086 | 7.8 | 4.9 |
| AN0088 | 5.1 | 4.5 |
| AN0090 | 6.8 | 6.4 |

FLAMe method. Another method to remove unwanted fluorescence background is to employ the fluorescence lifetime anisotropy method (FLAMe). This method can eliminate the effect of background fluorescence in a polarization assay if the background has an average lifetime distinct from the analyte lifetime.

FLAMe uses the time-resolved fluorescence anisotropy measured in the frequency domain to distinguish the long and short lifetime components. The measurement is then manipulated to establish the ratio of bound probe molecules to the sum of the bound and free molecules (the fraction of bound molecules). The goal of the method is to establish a way to measure the fraction of bound molecules (or free ones) without interference from other fluorescing compounds.

Derivation of the FLAMe method. The lifetime discriminated intensity (LDI) may be used for the rejection of short lifetime background when a long lifetime analyte is used (also the reverse is possible). The LDI can be substituted anywhere a conventional intensity would be used. For a polarization assay, the LDI of the parallel intensity and the LDI of the perpendicular intensity can replace the parallel and perpendicular intensity values used to calculate the polarization (or anisotropy).

$$P = \frac{(LDI_\parallel) - G(LDI_\perp)}{(LDI_\parallel) + G(LDI_\perp)} \qquad (13)$$

Figure 33:
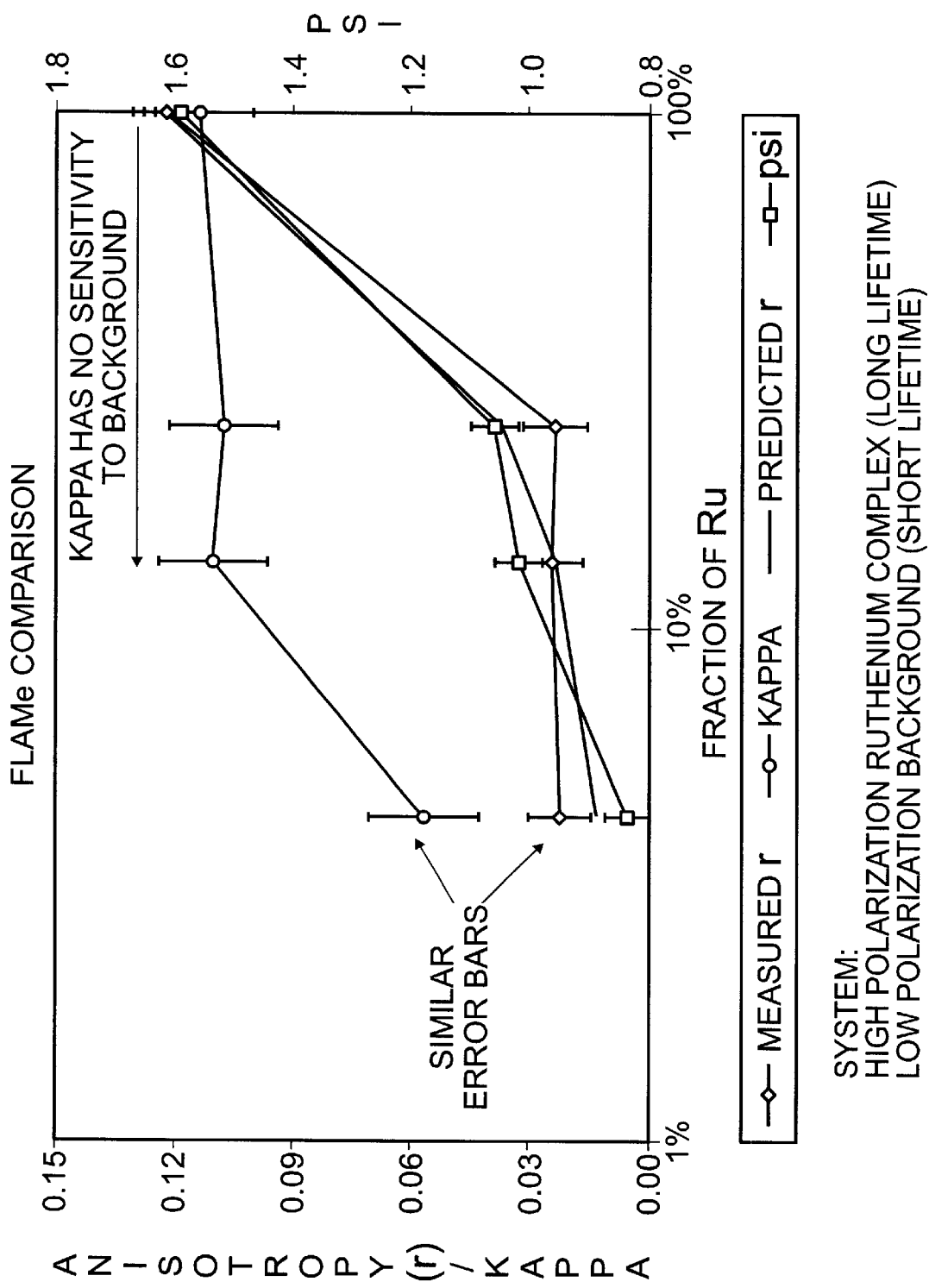
FIG. 33 is a graph of experimental results showing that short-lifetime background with low polarization does not significantly affect performance of FLAMe methods.

FIG. 33 shows using experimental results that short-lifetime background with low polarization does not significantly affect performance of FLAMe methods.

B. Intensity Assays

The apparatus and methods provided by the invention can be used to discriminate between analyte and background in intensity assays. Background-corrected intensities derived from such intensity assays can be used directly, as intensities, or they can be used indirectly to determine quantities such as polarization and luminescence lifetime. Generally, the invention permits determination of background-corrected intensities for systems having one or more analytes and one or more background components.

Two-component analysis. In systems having two detectable components, such as analyte and background, the contribution of each component to the total intensity can be determined using the intensity, phase, and modulation of the system, measured at a single angular modulator frequency $\omega$. This embodiment of the invention may be termed lifetime-discriminated intensity (LDI).

In the time domain, the luminescence of a complex luminophore or of a mixture of luminophores normally decays as a series of exponentials.

$$I(t) = \sum_i \alpha_i e^{-t/\tau_i} \quad (14)$$

Here, I(t) is the time-dependent luminescence intensity, $a_i$ is a preexponential factor, and $\tau_i$ is the luminescence lifetime of the ith component. The fraction of the steady-state luminescence intensity contributed by each component may be found by integrating Equation 14 over time.

$$f_i = \alpha_i \tau_i \Big/ \sum_j \alpha_j \tau_j \quad (15)$$

Here, $f_i$ is the fractional intensity of the ith component.

In the frequency domain, the phase and modulation phasor of a complex luminophore or a mixture of luminophores is a vector sum of the phase and modulation of the individual components, weighted by the individual components' fractional contributions to the total intensity.

Figure 34:
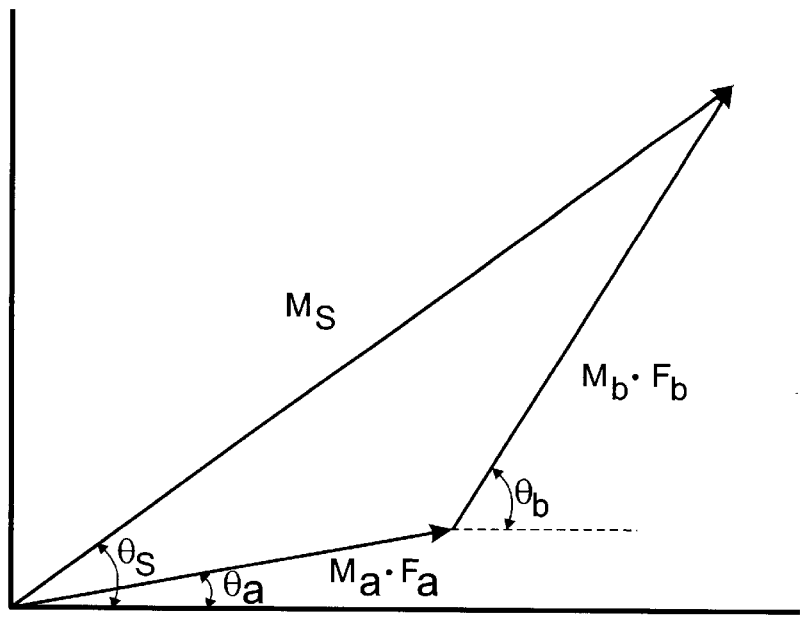
FIG. 34 is a phasor diagram showing phase and modulation phasors for a system having an analyte and background.
Figure 35:
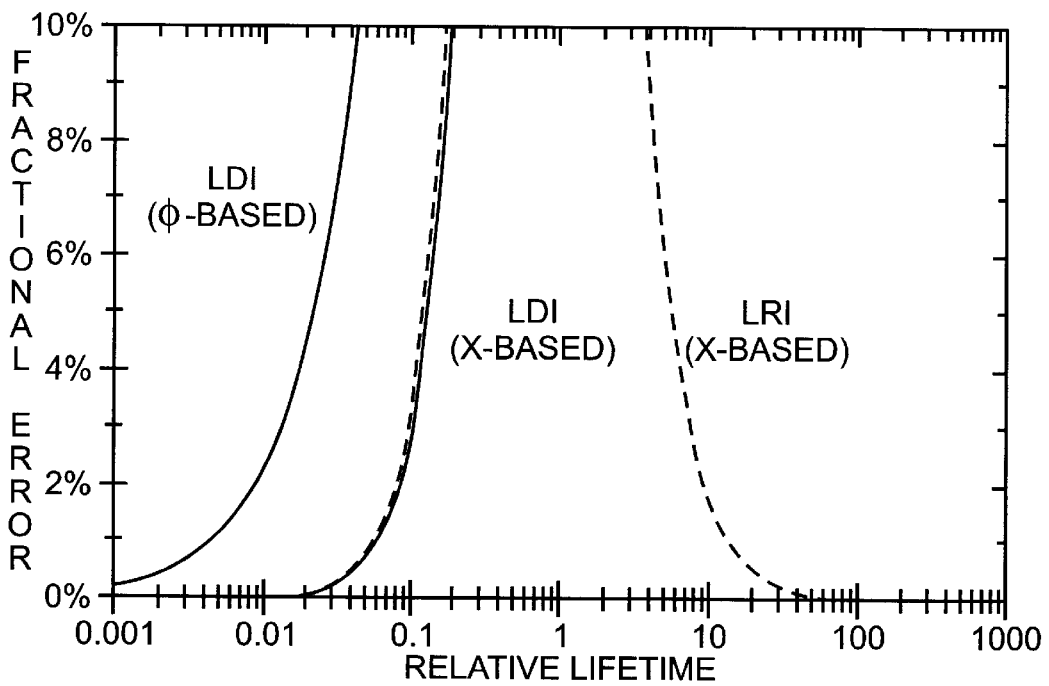
FIG. 35 is a graph of simulation results showing how the invention discriminates between an analyte and background for three zeroth-order embodiments of the invention, as described in Equations 13 (LDI, $M_x$-based), 15 (LDI, $\phi$-based), and 16 (LRI).

FIG. 34 shows phase and modulation for a system containing two luminophores, such as an analyte and background. The phase and modulation of the system can be expressed in terms of X and Y components of the phasor.

$$M_s = \sqrt{M_{s,x}^2 + M_{x,y}^2} \quad (16)$$

$$\phi_s = \arctan\left(\frac{M_{s,y}}{M_{s,x}}\right) \quad (17)$$

Here 's' denotes system, and 'x' and 'y' denote X and Y components. The X and Y components for the system can be expressed in terms of X and Y components for the analyte and background alone.

$$M_{s,x} \equiv M_s \cdot \cos\phi_s = f_a \cdot M_a \cdot \cos\phi_a + (1-f_a) \cdot M_b \cdot \cos\phi_b \quad (18)$$

$$M_{s,y} \equiv M_s \cdot \sin\phi_s = f_a \cdot M_a \cdot \sin\phi_a + (1-f_a) \cdot M_b \cdot \sin\phi_b \quad (19)$$

Here 'a' denotes analyte, and 'b' denotes background.

Equations 18 and 19 can be rearranged to solve for the fractional intensities of the analyte and background. The fractional intensity $f_a$ of the analyte is $$f_a = \frac{M_{b,i} - M_{s,i}}{M_{b,i} - M_{a,i}} \quad (20)$$

Here 'i' denotes x or y, corresponding to X or Y components. To calculate fractional intensity using Equation 15, three quantities must be known: $M_{s,x}$, corresponding to the system; $M_{a,x}$, corresponding to analyte alone; and $M_{b,x}$, corresponding to background alone. $M_{s,x}$ is determined for each sample, by making a measurement on each sample. $M_{a,x}$ is determined for each analyte, not for each sample, either (1) by measuring the modulation using a blank containing the analyte "without" background (possibly at high concentration), or (2) by calculating the modulation using Equations 4–5 and the analyte lifetime as measured above without background. The assumption is that the analyte is the same in every sample but that the background is different in every sample. $M_{b,x}$ is estimated for each sample, by making a measurement on a blank for each sample. $M_{b,x}$ typically varies from sample to sample, because the background may include contributions both from the composition and from the holder and optics surrounding the composition. $M_{b,x}$ may be estimated by making a measurement on a blank and assuming that the measured value can be applied to each sample.

The apparatus and methods provided by the invention allow a more elegant and accurate solution to background correction, which does not require the use of a blank. Equation 8 can be rewritten as a power series of $\omega\tau_b$ if the background has a short lifetime ($\omega\tau_b \ll 1$), and as a power series of $1/\omega\tau_b$ if the background has a long lifetime ($1/\omega\tau_b \ll 1$). If the background has a short lifetime, the analyte fractional intensity is $$f_a = \frac{1 - M_{s,x}}{1 - M_{a,x}} + \frac{M_{a,x} - M_{s,x}}{(1 - M_{a,x})^2} \cdot (\omega\tau_b)^2 + \ldots \xrightarrow{\lim_{\omega\tau_b \to 0}} \frac{1 - M_{s,x}}{1 - M_{a,x}} \quad (21)$$

If the background has a long lifetime, the analyte fractional intensity is $$f_a = \frac{M_{s,x}}{M_{a,x}} + \frac{M_{s,x} - M_{a,x}}{M_{a,x}^2} \cdot \frac{1}{(\omega\tau_b)^2} + \ldots \xrightarrow{\lim_{\omega\tau_b \to 0}} \frac{M_{s,x}}{M_{a,x}} \quad (22)$$

Equations 20 and 21 discriminate between light emitted by the analyte and short- or long-lifetime background, based on differences in lifetime, without requiring the lifetime or intensity of the background. If the value of the background lifetime is unknown, Equation 21 can be evaluated by setting $\omega\tau_b$ equal to zero (short lifetimes), and Equation 22 can be evaluated by setting $\omega\tau_b$ equal to infinity (long lifetimes). If the value of the background lifetime is known, Equations 21 and 22 can be evaluated exactly, yielding an improved value of $f_a$.

Equations 16, 17, and 19 also can be rewritten as power series. In this way, various equations can be derived. For example, in a phase-based formulation, if the background has a short lifetime, the analyte fractional intensity is $$f_a = \frac{\tan\phi_s}{M_{a,y} + (1 - M_{a,x}) \cdot \tan\phi_s} + \frac{M_{a,y} + (2 - M_{a,x}) \cdot \tan\phi_s}{(M_{a,y} + (1 - M_{a,x}) \cdot \tan\phi_s)^2} \cdot \omega\tau_b \quad (23)$$

Variations in the intensity and lifetime of the background do not affect the determination of $f_a$, as long as $\omega\tau_b$ is small (Equations 21 and 23) or large (Equation 22). This is true even if the background includes multiple components, as long as the lifetime of each component is short (Equations 21 and 23) or long (Equation 22). In this case, it is appropriate to use the average or effective lifetime of the background in evaluating Equations 21–23.

Various factors determine which equation is best for discriminating between analyte and background. One factor is background lifetime: if background lifetime is short, an equation expanded in $\omega\tau_b$ should be used; if background lifetime is long, an equation expanded in $1/\omega\tau_b$ should be used. Another factor is knowledge of background lifetime: if $\tau_b$ is unknown, Equations 21 and 22 generally should be used, because they are second (and higher) order in lifetime and so relatively insensitive to the value of the lifetime. Yet another factor is experimental: to avoid recording average intensity and to permit detection electronics to be optimized for AC operation, Equation 23 generally should be used. Yet another factor is the nature of the background: if the background has both short- and long-lifetime components, Equations 21 and 23 will overestimate analyte intensity, because long-lifetime background will be confused with analyte, and Equation 22 will underestimate analyte intensity, because short-lifetime background will be confused with analyte. In such situations, a three-component analysis should be used.

Three-component analysis. In a system having three detectable components, such as an analyte and both short- and long-lifetime backgrounds, the contribution of each component to the total intensity can be determined using the intensity, phase, and modulation of the system, measured at two angular modulation frequencies ($\omega_1, \omega_2$). In this case, the fractional intensity of the analyte is $$f_a = p(\omega_1) - q(\omega_1) \cdot \frac{p(\omega_2) - p(\omega_1)}{q(\omega_2) - q(\omega_1)} \quad (24)$$

$$p(\omega) \equiv \frac{1 - M_{s,x}}{1 - M_{a,x}} + \frac{M_{a,x} - M_{s,x}}{(1 - M_{a,x})^2} \cdot (\omega \tau_{bs})^2 \quad (25)$$

$$q(\omega) \equiv \frac{\frac{1}{(\omega \tau_{bl})^2} - 1}{1 - M_{a,x}} + \frac{\frac{1}{(\omega \tau_{bl})^2} - M_{a,x}}{(1 - M_{a,x})^2} \cdot (\omega \tau_{bs})^2 \quad (26)$$

Here 'bs' and 'bl' denote short- and long-lifetime background, respectively. Equations 25 and 26 are correct to third order for single exponential backgrounds. If the short- and/or long-lifetime background include multiple components, the average or effective lifetime of the short components and the average or effective lifetime of the long components should be used for $\tau_{bs}$ and $\tau_{bl}$, respectively. This embodiment of the invention may be termed lifetime-resolved intensity (LRI).

Practical considerations. FIG. 25 shows simulation results demonstrating the ability of the invention to discriminate between an analyte and a background. Results are shown for three zeroth-order embodiments of the invention, as described in Equations 21 (LDI, $M_x$-based), 23 (LDI, $\phi$-based), and 25 (LRI). The error is determined by the choice of frequency and analyte lifetime. When the lifetimes of the analyte and background differ by more than a factor of ten for the equations based on the X components of the modulation, the error is low enough (<2%) for HTS applications.

The choice of frequency also is important for small systematic errors. In the lifetime-discriminated case (Equation 21), the frequency must be chosen so that the measured quantity ($M_{s,x}$) is useable. The errors in $M_{s,x}$ must not translate into a large uncertainty in the derived fractional intensity. If the fraction of analyte is large, any frequency appropriate for measuring the analyte will suffice. For example, if the analyte has a lifetime of 100 nanoseconds, any frequency in the range of 300 kHz to 8 MHz is appropriate (from ⅕ to 5× the inverse lifetime).

If the fraction of analyte is low, however, the frequency selection is constrained by the fact that $M_{s,x}$ is dominated by the short lifetime background. Its value will be too close to the upper limit (1.000) if the frequency is too small. A normal value for the error in M would be 0.005. With this size error, it is not reasonable to make a precise measurement of M when its value is greater than 0.980. This upper limit will make low frequencies unusable. For a ruthenium-complex analyte having a lifetime of 360 nanoseconds and a background having a lifetime of <5 nanoseconds, a reasonable frequency is 2–3 MHz.

In the lifetime-resolved case (Equation 25), the choice of frequencies is more difficult. Roughly, one frequency is needed to discriminate between the long and intermediate lifetimes, and one frequency is needed to discriminate between the intermediate and short lifetimes. Each frequency may be chosen as for a two-component system. However, using an optimization program to choose the frequencies may be more reliable and robust. The program optimizes the frequencies to minimize systematic error due to finite lifetimes of the short and long components, while also minimizing the error due to changes in analyte lifetime.

Experimental verification. The luminescence intensity due to the analyte can be found by multiplying the total intensity by the calculated fractional intensity, using Equations 20 (LDI), 22 (LDI), or Equation 23 (LRI), among others. Total intensity is obtained from the steady-state value of the luminescence emission, without performing a separate experiment. To test these concepts, we built a phase and modulation fluorometer capable of measuring samples in a microplate, as described above. The instrument uses epi-luminescence geometry, an intensity-modulated blue LED, and a gain-modulated PMT.

Experiments were conducted to assess the ability of the apparatus and methods to discriminate between analyte and background. The analyte was $[Ru(bpy)_3]Cl_2$ (ruthenium tris-2,2'-bipyridyl chloride), which has a long lifetime in buffer (measured at 330 nanoseconds at a temperature of 26–28° C. in 20 millimolar PBS, pH 7.4). The background was from the sample container and/or added R-phycoerythrin. R-phycoerythrin was used as an intentional background contaminant because its excitation and emission spectra overlap those of $Ru(bpy)_3$ and because it has a short lifetime in buffer (measured at 2.9 nanoseconds in 20 millimolar PBS, pH 7.4). All samples were prepared with 20 mM PBS, pH 7.4, and all data were collected with a 400 millosecond integration time in COSTAR-brand flat-black 96-well microplates.

Ruthenium is a good long-lifetime probe for several reasons. First, ruthenium has a long lifetime. Second, ruthenium's lifetime is not extremely sensitive to oxygen concentration, even though ruthenium sometimes is used as an oxygen sensor. This is because ruthenium's lifetime is short relative to good oxygen sensors. In particular, ruthenium's lifetime is not particularly sensitive to normal changes in oxygen content in air-equilibrated buffer, so that no special measures must be taken to remove oxygen from the system. Third, ruthenium is an atomic luminophore, so that it is not subject to the common problem of photobleaching. Finally, the ruthenium complex has a convenient excitation spectrum (460 nanometer peak) and a large (140 nanometer) Stokes' shift. (The Stokes' shift is the separation between maxima in excitation and emission spectra.)

Conventional background subtraction fails when the background concentration is too large due to fluctuations in background intensity and variations from sample to sample. A 1% variation between samples will make it impossible to measure an analyte whose intensity is only 1% of the background signal. To have confidence that a signal exists, a three standard-deviations rule may be used. The minimum resolvable signal is defined as a signal that is three standard deviations larger than the average background.

For a background-subtracted value, our confidence limit translates to a fractional error (or coefficient of variation, CV) of about 47%. (Both sample and background were assumed to have the same error with the difference three times the error; $CV=\sqrt{3}/2$.) Such a large CV is usable only for qualitative measurements. For quantitative measurements, a smaller CV is desired. Typical dispensing errors, concentration errors, and instrument drift can combine to give an error of several percent. Considering these other errors, it is practical to use data with a 10% CV for quantitative work, which may be considered the limit for precise data. These confidence and precision limits allow quantitatively comparison of data from background-subtracted intensity, lifetime-discriminated intensity, and lifetime-resolved intensity measurements.

Figure 36:
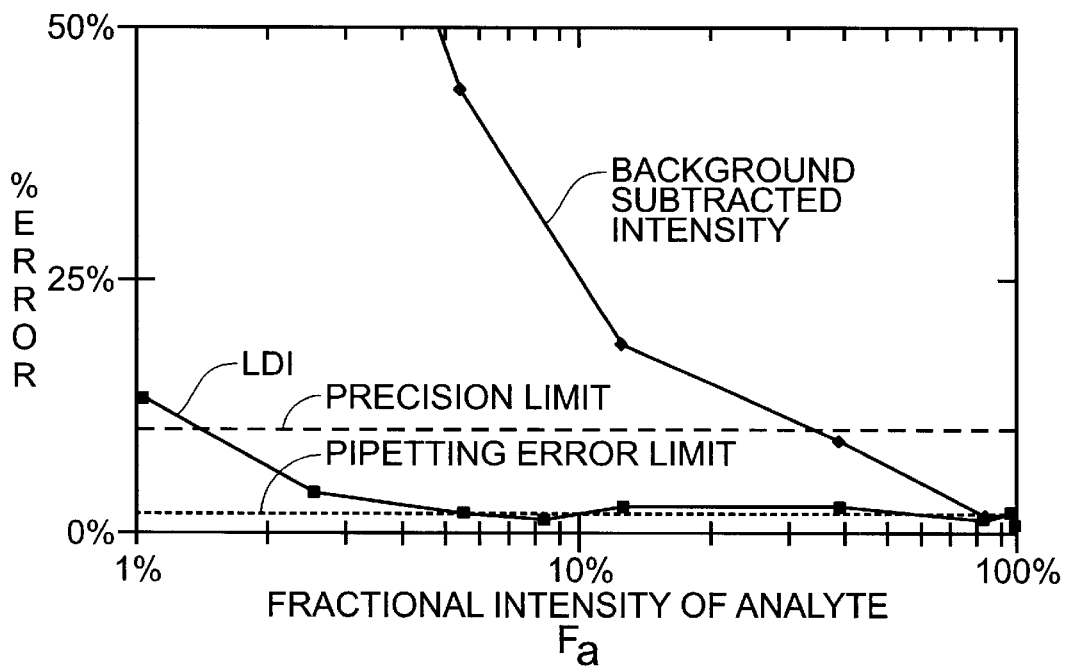
FIG. 36 is a graph of experimental results showing how the invention discriminates between a long-lifetime ruthenium-complex analyte and a short-lifetime R-phycoerythrin background, for a constant concentration of analyte and an increasing concentration of background. Results are shown for embodiments described under FIG. 35.

FIG. 36 shows experimental results demonstrating sensitivity to background, determined by adding increasing concentrations of R-phycoerythrin to a constant concentration of Ru(bpy)$_3$. The result was a series of solutions with increasing total intensity but constant analyte intensity. All solutions were prepared in duplicate, and errors in the average were compared with expected values. FIG. 9 shows three curves. LDI corresponds to Equation 21, evaluated at 2.85 MHz. LRI corresponds to Equation 25, evaluated at $f_1$=0.35 MHz and $f_2$=4.33 MHz. BSI corresponds to the background-subtracted intensity, computed using a blank. The ability of a method to discriminate analyte and background is given by the analyte fractional intensity at which measurement error exceeds the confidence limit. The background-subtraction method can discriminate between analyte and background only if the analyte fractional intensity exceeds 17%, whereas LDI and LRI can discriminate between analyte and background if the analyte fractional intensity exceeds 2% and <0.8%, respectively. Therefore, both methods are less than one-tenth as responsive to background luminescence as background subtraction. This reduced responsivity is achieved while reducing experimental complexity. Under the proper conditions, LDI and LRI do not require any measurement of the background luminescence, including its lifetime and intensity. The contribution of background to the measured intensity is removed simply because of its short lifetime.

Figure 37:
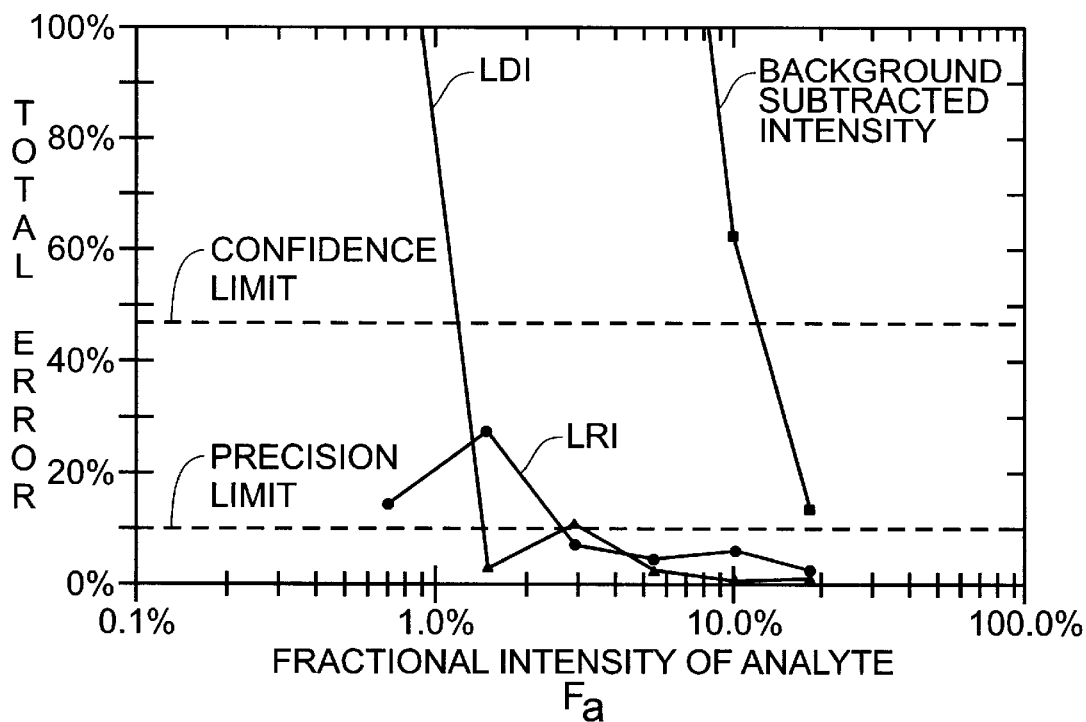
FIG. 37 is a graph of experimental results showing how the invention discriminates between a long-lifetime ruthenium-complex analyte and a short-lifetime R-phycoerythrin background, for a constant concentration of background and an increasing concentration of analyte. Results are shown for embodiments described under FIG. 35.

FIG. 37 shows experimental results demonstrating sensitivity to analyte, determined by adding increasing concentrations of Ru(bpy)$_3$ to a constant (1 nanomolar) concentration of R-phycoerythrin. The result was a series of solutions with increasing total intensity but constant background intensity. This setup permits a determination of the minimum resolvable fraction of analyte in the presence of background. All solutions were prepared in duplicate, and errors in the average were compared with expected values. We measured the LDI was measured at 2.85 MHz, and LRI was measured at 0.35 and 2.85 MHz. The difference between methods is again substantial. Background subtraction quickly fails to resolve the analyte (at a fractional intensity of 13% or 100 micromolar of ruthenium complex). LDI reports the correct analyte intensity down to a fractional intensity of 1% (10 $\mu$M), while LRI reports the correct intensity down to less than 0.7% (5 micromolar). This is a greater than tenfold increase in the sensitivity to the analyte for either method. These consistent results suggest that LDI and LRI measurements can be a significant improvement over conventional background subtraction.

The invention is robust, simple, and fast, making it ideal for high-throughput screening. LDI is able accurately to distinguish short- and long-lifetime components using phase and modulation at only a single frequency. LRI is able accurately to separate three lifetime components using phase and modulation at two frequencies. Extension to even more components also is possible. Knowledge of the lifetime of one component is used to determine the intensity of each component, without requiring a determination of the lifetime or intensity of the other component.

C. Polarization Assays

The apparatus and methods provided by the invention also can be used to discriminate between analyte and background in polarization assays. Generally, the invention permits determination of background-corrected polarizations for systems having one or more analytes and one or more background components.

Background-corrected steady-state polarizations (or anisotropies) may be determined using Equation 1, where $I_\parallel$ and $I_\perp$ may be determined using appropriate combinations of parallel and perpendicular excitation and emission polarizers, and the apparatus and methods described above for computing background-corrected intensities. Such corrections are important, because steady-state anisotropies are intensity-weighted averages of the anisotropies of all components present, so that background affects the measured anisotropies directly.

Background-corrected time-resolved polarizations (or anisotropies) may be determined using time-domain or frequency-domain techniques. In the time domain, background-corrected polarizations may be determined using Equation 1, where $I_\parallel$ and $I_\perp$ are replaced by $I_\parallel(t)$ and $I_\perp(t)$. In the frequency domain, background-corrected polarizations may be determined using appropriate combinations of parallel and perpendicular phase $\phi_p$ and parallel and perpendicular modulation $M_p$. Here 'p' denotes parallel or perpendicular, corresponding to parallel and perpendicular components. $\phi_p$ and $M_p$ are determined using the same apparatus and methods as $\phi$ and M, with the addition of parallel and perpendicular polarizers, as appropriate. $\phi_p$ and $M_p$ may be rewritten in terms of $\omega$ and $I(t)$.

$$\phi_{p\omega} = \tan^{-1}(N_{p\omega}/D_{p\omega}) \tag{27}$$

$$M_{p\omega} = \sqrt{N_{p\omega}^2 + D_{p\omega}^2}/J_p \tag{28}$$

$$J_p = \int_0^\infty I_p(t)\,dt \tag{29}$$

$$N_{p\omega} = \int_0^\infty I_p(t)\sin(\omega t)\,dt \tag{30}$$

$$D_{p\omega} = \int_0^\infty I_p(t)\cos(\omega t)\,dt \tag{31}$$

Experimental results may be interpreted using a differential phase angle $\Delta_\omega$ and a ratio $\Lambda_\omega$ of the parallel and perpendicular AC components of the polarized emission.

$$\Delta_\omega = \phi_{\perp\omega} - \phi_{\parallel\omega} \tag{32}$$

$$\Lambda_\omega = \frac{AC_\parallel}{AC_\perp} = \frac{\sqrt{N_{\parallel\omega}^2 + D_{\parallel\omega}^2}}{\sqrt{N_{\perp\omega}^2 + D_{\perp\omega}^2}} \tag{33}$$

$\Lambda_\omega$ may be used to define a frequency-dependent quantity $r_\omega$, called the modulated anisotropy.

$$r_\omega = \frac{\Lambda_\omega - 1}{\Lambda_\omega + 2} \tag{34}$$

$r_\omega$ tends to the fundamental anisotropy $r_0$ at high frequency and to the steady-state anisotropy $r_{ss}$ at low frequency.

Frequency-domain time-resolved polarization may be used to investigate the motional properties of biological molecules in more detail than steady-state polarization. For example, a biophysical model may be used to generate functional forms of $I_\parallel(t)$ and $I_\perp(t)$, using parameters such as lifetimes and rotational correlation times. This model can be used to predict $\Delta_\omega$ and $\Lambda_\omega$. Experiments then can be done to measure $\Delta_\omega$ and $\Lambda_\omega$, at one or more modulation frequencies. Experimental results may be fitted to the model by adjusting the parameters to give the best fit between predicted and observed values of $\Delta_\omega$ and $\Lambda_\omega$ or $r_\omega$, for example, by using nonlinear least-squares optimization algorithms.

Alternatively, a simpler approach may be used, in which experiments are conducted at one or a few modulation frequencies, and experimental results are interpreted without resort to fitting to detailed models. Such an approach may be sufficient quickly to assay for significant changes in molecular mobility, for example, as occurs upon binding. Such binding may be to a target molecule as part of an assay, or to walls of the sample container, among others.

Figure 38A:
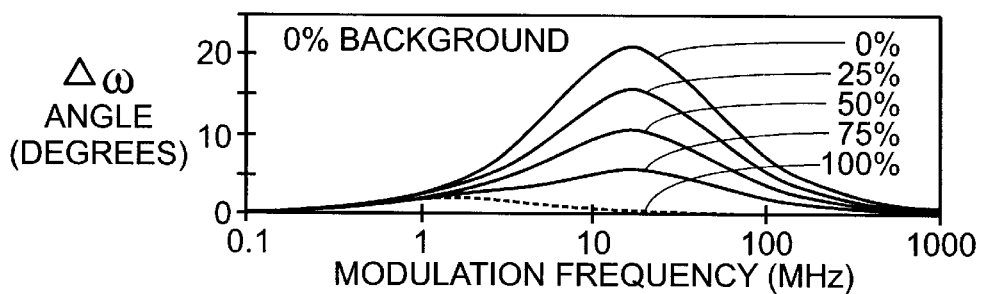
FIG. 38 is a graph of simulation results showing how binding affects differential phase (Panel A) and modulated anisotropy (Panel B) in the presence of 0% background in a frequency-domain binding experiment, for 0–100% binding as shown.
Figure 38B:
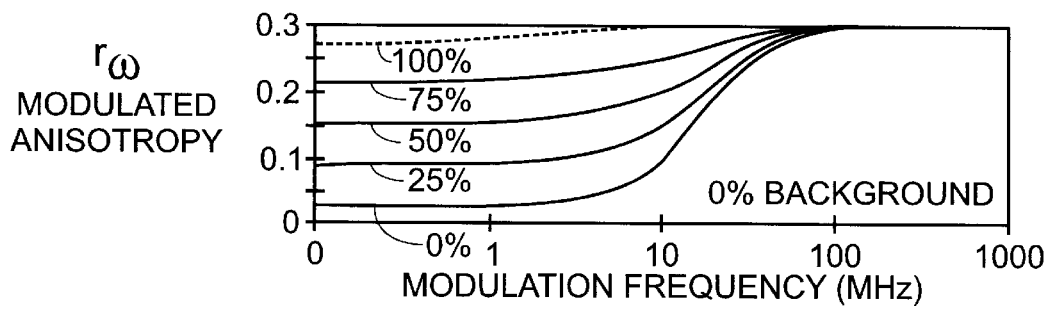

FIG. 38 shows how $\Delta_\omega$ (Panel A) and $r_\omega$ (Panel B) depend on $\omega$ for a simple binding system in the absence of background. Here, the labeled molecule has a fundamental anisotropy $r_o=0.3$, a luminescence lifetime $\tau=100$ nanoseconds, and a rotational correlation time $\tau_{rot}=10$ nanoseconds in the free state and 1000 nanoseconds in the bound state. FIG. 38 shows results for 0%, 25%, 50%, 75%, and 100% binding. The extent of binding of the labeled molecule can be determined quickly and sensitively by measuring $\Delta_\omega$ and $r_\omega$ at a single suitable frequency (e.g., ~20 MHz for $\Delta_\omega$, and <~10 MHz for $r_\omega$), and then reading off the extent of binding from an empirical calibration curve. Alternatively, binding could be determined using LDI and LRI, among others, if the binding is associated with a change in analyte lifetime.

Figure 39A:
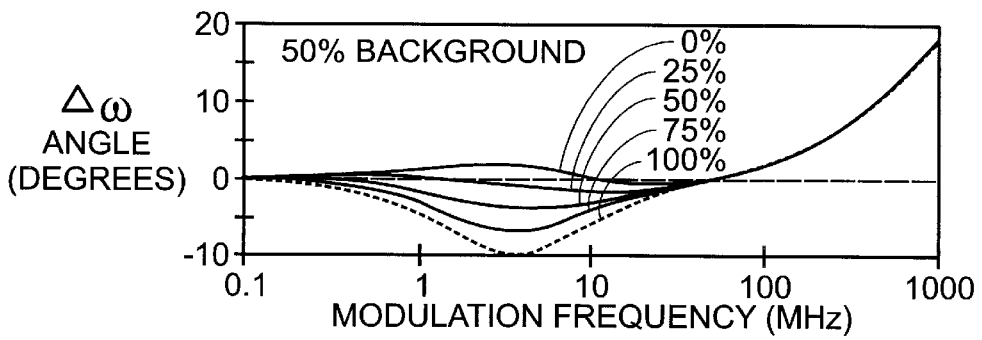
FIG. 39 is a graph of simulation results showing how binding affects differential phase (Panel A) and modulated anisotropy (Panel B) in the presence of 50% background in the frequency-domain binding experiments shown in FIG. 38.
Figure 39B:
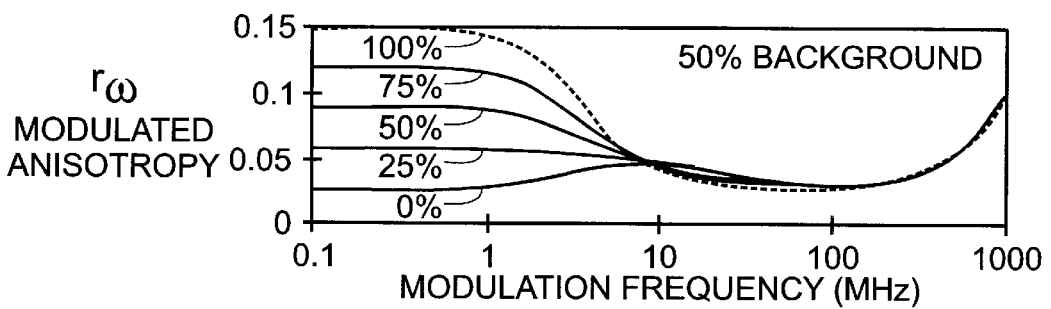

FIG. 39 shows how $\Delta_\omega$ (Panel A) and $r_\omega$ (Panel B) depend on $\omega$ for a simple binding system in the presence of 50% background. Here, the background has a fundamental anisotropy $r_o=0.3$ a luminescence lifetime $\tau=1$ nanosecond, and a rotational correlation time time $\tau_{rot}=0.1$ nanosecond. These conditions correspond to compositions having a long-lifetime analyte and a short-lifetime background; the effective luminescence lifetime of the background usually is short, probably 0.1 to 10 nanoseconds. Unfortunately, a comparison of FIGS. 38 and 39 shows that there are no frequencies at which either $\Delta_\omega$ or $r_\omega$ is unaffected by the background. This greatly diminishes the utility of $\Delta_\omega$ or $r_\omega$, especially because background varies from sample to sample, and so generally cannot be included in a calibration curve.

These shortcomings are addressed by the invention, which provides alternative functions that better discriminate between analyte and background, without requiring information from a blank and without requiring a determination of the lifetime or intensity of the background. Two such functions, denoted "psi" and "kappa" functions, are described below.

Psi function. The psi function, or $\Psi_\omega$, is a ratio of the parallel and perpendicular AC intensities, weighted by the sines of the parallel and perpendicular phases, respectively.

$$\Psi_\omega = \frac{AC_\| \sin(\phi_{\|\omega})}{AC_\perp \sin(\phi_{\perp\omega})} \tag{35}$$

$\Psi_\omega$ may be shown to be a ratio of the sine Fourier transforms $N_{p\omega}$ of the intensity decays in associated parallel and perpendicular measurements. To see this, simple trigonometry and the relationship $\phi_{p\omega}=\tan^{-1}(N_{p\omega}/D_{p\omega})$ give $$\sin(\phi_{p\omega}) = \frac{N_{p\omega}}{\sqrt{N_{p\omega}^2 + D_{p\omega}^2}} \tag{36}$$

Then, using Equation 36 defining $\Lambda_\omega$ gives $$\Psi_\omega = \frac{AC_\| \sin(\phi_{\|\omega})}{AC_\perp \sin(\phi_{\perp\omega})} = \frac{\sqrt{N_{\|\omega}^2 + D_{\|\omega}^2}}{\sqrt{N_{\perp\omega}^2 + D_{\perp\omega}^2}} \frac{\sin(\phi_{\|\omega})}{\sin(\phi_{\perp\omega})} = \frac{N_{\|\omega}}{N_{\perp\omega}} \tag{37}$$

Figure 40:
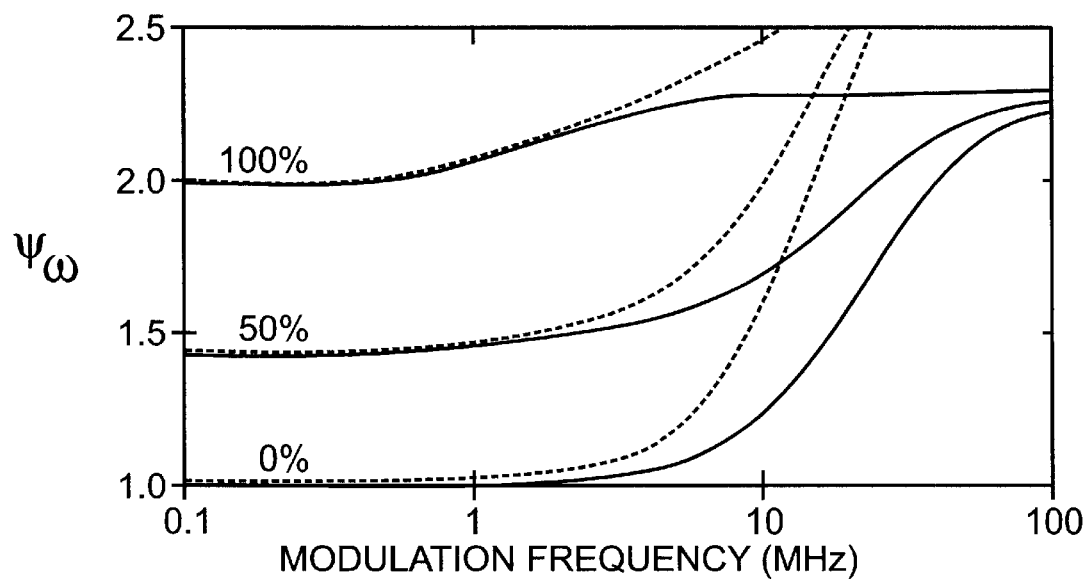
FIG. 40 is a graph of simulation results showing how binding affects $\Psi_\omega$ in the presence of 0% (solid lines) and 50% (dashed lines) background in the frequency-domain experiments of FIG. 38, for 0–100% binding as shown. $\Psi_\omega$ is defined and evaluated in accordance with the invention.

FIG. 40 shows how $\Psi_\omega$ depends on $\omega$ for the system of FIGS. 11 and 12, in the presence of 0% (Panel A) and 50% (Panel B) background. Generally, the lower the frequency, the less $\Psi_\omega$ is affected by the (short-lifetime) background. In particular, below $\omega \sim 10$ MHz, $\Psi_\omega$ is much less affected by background than $\Delta_\omega$ and $r_\omega$. However, as $\omega$ becomes small, $\theta_p$ also becomes small, and measurement of the sine becomes imprecise. The optimum modulation frequency will be determined by a balance of these factors, among others.

The behavior of $\Psi_\omega$ for short-lived signals can be understood as follows. Assume that there are n molecular components, each with a single luminescence lifetime $\tau_i$ and a single rotational correlation time $\tau_{rot,i}$. The fraction of the steady-state luminescence intensity (no polarizers) contributed by each component is given by Equation 8. In the time domain, the anisotropy of each component is given by $$r_i(t) = r_{oi} e^{-t/\theta_i} \tag{38}$$

Then by the standard relationships $$I_\|(t) = \frac{1}{3} I(t)(1 + 2r_i(t)); \quad I_\perp(t) = \frac{1}{3} I(t)(1 - r_i(t)) \tag{39}$$

Taking the sine Fourier transform gives $$N_{\|\omega} = \frac{1}{3} \left\{ \sum_i a_i \tau_i \left[ L(\omega\tau_i) + 2r_{oi} \frac{\sigma_i}{\tau_i} L(\omega\sigma_i) \right] \right\} \tag{40}$$

$$N_{\perp\omega} = \frac{1}{3} \left\{ \sum_i a_i \tau_i \left[ L(\omega\tau_i) - r_{oi} \frac{\sigma_i}{\tau_i} L(\omega\sigma_i) \right] \right\} \tag{41}$$

Here, $L(x)=x/(1+x^2)$. For $|x|<<1$, $L(x)\sim x$ and $L(0)=0$. $L(x)$ reaches a maximum value of ½ at $x=1$. For $|x|>>1$, $L(x)\sim 1/x$, and $L(\infty)=0$. The rotational correlation time enters the system only through $$\sigma_i = \frac{\tau_i \theta_i}{\tau_i + \theta_i} \tag{42}$$

Because ½ $\min(\tau_i,\theta_i) \leq \sigma_i < \min(\tau_i,\theta_i)$, $\sigma$ always is smaller than either $\tau$ or $\sigma$. The ratio $\sigma_i/\tau_i=\theta_i/(\tau_i+\theta_i)<1$. $\Psi_\omega$ can be formed by taking a ratios of the N's and recalling that $$a_i \tau_i = f_i \sum_j a_j \tau_j.$$

$$\Psi_\omega = \frac{N_{\|\omega}}{N_{\perp\omega}} = \frac{\sum_i f_i \left[ L(\omega\tau_i) + 2r_{oi}\frac{\sigma_i}{\tau_i}L(\omega\sigma_i) \right]}{\sum_i f_i \left[ L(\omega\tau_i) - r_{oi}\frac{\sigma_i}{\tau_i}L(\omega\sigma_i) \right]} \quad (43)$$

Here, the normalizing sum canceled out of all the terms.

Based on the behavior of L(x) for small x, $\Psi_\omega$ gives small weight to signals from short-lived species ($\omega\tau_i$ or $\omega\sigma_i \ll 1$), in comparison to signals for which $\omega\tau_i$ or $\omega\sigma_i \sim 1$. $\Psi_\omega$ also gives small weight to the anisotropy contributions of long-lived components that have extremely short rotational correlation times (i.e., $\omega\sigma_i \ll 1$, $\sigma_i/\tau_i \ll 1$).

Kappa function. The kappa function, or $K_\omega$, is a ratio involving the parallel and perpendicular AC intensities, weighted in part by the cosines of the parallel and perpendicular phases, respectively.

$$K_\omega = \frac{I_\| - AC_\| \cos\phi_{\|\omega} - (I_\perp - AC_\perp \cos\phi_{\perp\omega})}{I_\| + AC_\| \cos\phi_{\|\omega} + 2(I_\perp - AC_\perp \cos\phi_{\perp\omega})} \quad (44)$$

$K_\omega$ may be shown to be a ratio involving lifetime-discriminated intensities, as defined above, in associated parallel and perpendicular measurements.

$$K_\omega = \frac{LDI_\| - LDI_\perp}{LDI_\| + 2LDI_\perp} \quad (45)$$

Equation 45 is analogous to anisotropy, as may be seen by comparing Equation 45 for $K_\omega$ with Equation 2 for r.

Figure 41:
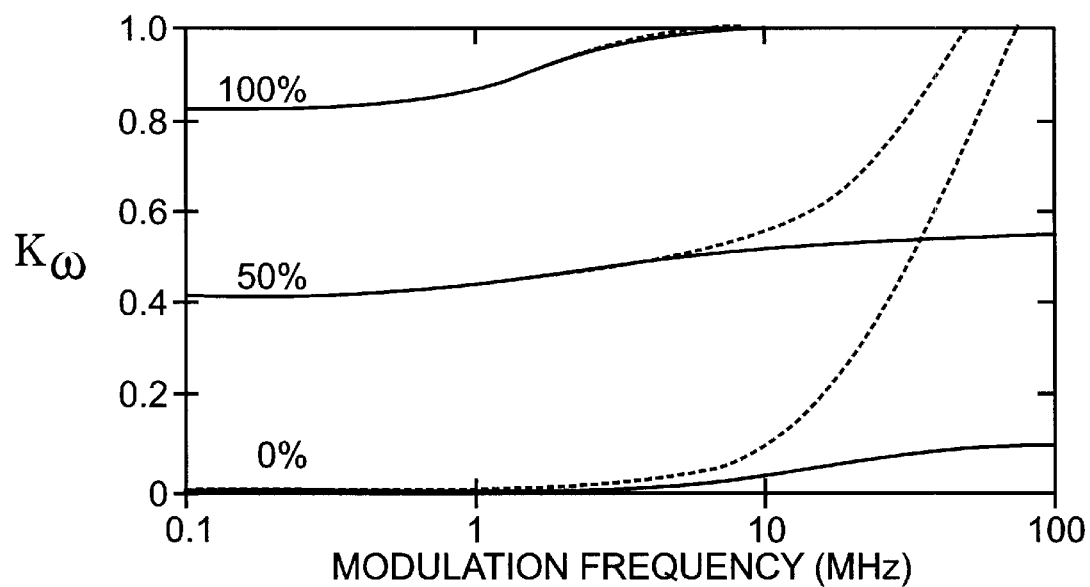
FIG. 41 is a graph of simulation results showing how binding affects $K_\omega$ in the presence of 0% (solid lines) and 90% (dashed lines) background in the frequency-domain binding experiments of FIG. 38. $K_\omega$ is defined and evaluated in accordance with the invention.

FIG. 41 shows how $K_\omega$ depends on $\omega$ for the system of FIGS. 38 and 39, in the presence of 0% (solid lines) and 90% (dashed lines) background. Results for $K_\omega$ are similar to results for $\Psi_\omega$, except that $K_\omega$ may be less sensitive than $\Psi_\omega$ to frequency for low frequencies, and to binding for high binding. Neither the kappa nor the psi function depends on properties of the background, so neither function requires use of a blank or a determination of the lifetime or intensity of the background.

D. Additional Methods

The invention provides additional new methods for discriminating between analyte and background in intensity (and thus indirectly in polarization) assays. Generally, these methods permit determination of background-corrected intensities for systems having one or more analytes and one or more background components. The remainder of this section is divided into three sections, which describe different methods provided by the invention: (A) "exact" algorithms for analyzing FLARe™ data, (B) correction of lifetime measurements for short-lived background, and (C) third-order FLDI (fluorescence lifetime discriminated intensity) algorithm for analyzing FLARe™ data. "Exact" Algorithms for Analyzing FLARe™ Data. A sample in a fluorometric assay may contain multiple fluorescent components. Some are present intentionally, and the characteristics of their emissions form the basis of the assay. Others constitute background and interfere with the interpretation of the assay. Sources of background include the optical components of the detection instrument, contaminants in the sample container, and various components of the assay solution. Where the background is the same in every sample being assayed (e.g., a predictable emission from the sample container), a separate measurement coupled with background subtraction can sometimes improve performance. However, a particular problem occurs during high-throughput screening for new pharmaceuticals, where the library compound being assayed is fluorescent. Background subtraction would necessitate doubling the number of assays performed (true measurement and background measurement for each compound), and background subtraction is in any event of limited utility.

Here we describe how arbitrarily accurate solutions to realistic models for the time-dependent fluorescence of mixtures of fluorophores can significantly reduce the effects of background without requiring the preparation of additional samples containing library compounds for background analysis.

We retain the fairly standard nomenclature that we have used in previous patent applications involving FD measurements of the type discussed here:

ν modulation frequency in Hz

ω modulation frequency in radians/s, $=2\pi\nu$

τ lifetime in ns or s

θ phase angle (equivalent to φ above)

M modulation n number of spectroscopically distinct types of fluorophores in the sample $f_i$ fraction of the steady-state fluorescence contributed by the $i^{th}$ fluorophore For an FD measurement, we define the quantities:

$$N = f_1 \omega \tau_1 / [1+(\omega\tau_1)_2] + f_2 \omega \tau_2 / [1+(\omega\tau_2)^2] + \ldots f_n \omega \tau_n / [1+(\omega\tau_n)^2] \quad (46)$$

$$D = f_1 / [1+(\omega\tau_1)^2] + f_2 / [1+(\omega\tau_2)^2] + \ldots f_n / [1+(\omega\tau_n)^2] \quad (47)$$

Then it can be shown (see J. Lakowicz, Principles of Fluorescence Spectroscopy, $2^{nd}$ Ed., 1999) that the observed phase and modulation are:

$$\theta = \arctan(N/D); \quad (48)$$

$$M = (N^2 + D^2)^{1/2} \quad (49)$$

Estimates of the intensity and lifetime parameters can be extracted from phase and modulation measurements by, e.g., nonlinear least-squares fitting of predicted to observed data.

For this to work, the number of unknowns must in general not exceed the number of independent data points. There are at most $2n-1$ unknowns (fractional intensities and lifetimes, reduced by one because the fractions must sum to unity). If reference measurements have already determined the values of parameters for individual components or subsets of components, this number can be reduced. The number of independent data points can be increased by making measurements at multiple modulation frequencies. For example, using two modulation frequencies generates four data points (θ and M each at two values of ω).

In general, these solutions are numerical rather than analytical, and generating them may be time consuming computationally. Simplifications can result from the fact that it is not necessary to determine the parameters for background components, only to correct for the effects of background on the signal of interest. Various approximations in the equations can also simplify the computational task.

Correction of Lifetime Measurements for Short-Lived Background. A single FD measurement with angular modulation frequency ω gives, in addition to FLINT, modulation M and phase θ that can be used (starting from Equations 4 and 5) to calculate a mean lifetime τ for the sample:

$$\tau = \tan(\theta)/\omega \quad (50)$$

$$\tau = \sqrt{1/M^2 - 1}\,\omega \quad (51)$$

If the fluorescence signal is produced by a single fluorophore exhibiting a single-exponential decay, these two equations yield the same value of the lifetime, the time constant for the decay.

When the fluorescence signal is more complicated, the two equations typically give different values of τ. Relating the measurement to the underlying molecular processes is more complicated and in general requires measurements at multiple wavelengths or modulation frequencies that are interpreted by fitting to some model. For example, when there are two fluorophores with distinct lifetimes, the measured values of phase and modulation are weighted averages of the phase and modulation results that would be obtained in experiments on the separate components. Moreover, the weighting is different for phase and modulation. Two separate FD measurements at appropriately chosen modulation frequencies are required to resolve the lifetimes and relative contributions to the FLINT of the two components.

The need to make multiple measurements on a sample slows the analytical process and is a disadvantage in applications, such as high-throughput screening, where it is important to minimize the assay time. Under some conditions, however, it is possible to resolve some of the molecular information from a complex sample with a single measurement.

For example, as shown above, it is possible to resolve the FLINT contributed by a long-lived label of interest in the presence of short-lived fluorescence background in a single FD measurement. This case has practical utility, because most fluorophores that contribute to contaminating background fluorescence in drug-discovery applications have lifetimes that are shorter than those of some of the available labels (especially metal-ligand complexes involving transition metals such as Ru, Os, and Re without limitation).

Here we report that under similar conditions, i.e., a label with a lifetime that is significantly longer than the lifetimes of all other contaminating signals, it is possible resolve the lifetime of that label in a single FD measurement, relatively free of interference from short-lived contaminants. This is contrasted with our previous work, which showed only that the FLINT of the label could be resolved from interference due to short-lived background.

The lifetime-measurement method that we describe here, which we call Fluorescence Lifetime Discriminated Lifetime (FLDL), is an approximation that works best when the ratio of background to label lifetimes is small and the ratio of background to label FLINT is small. However, when the lifetimes are well separated it is possible to resolve the label lifetime to a good approximation even when the FLINT from the background is significantly greater than that of the label.

Following is the theoretical development of the method.

Signals from an analyte A and background B combine to give the signal from the total system S. The lifetime of the analyte is $\tau_A$, and that of the background $\tau_B$. We assume that $\tau_B < \tau_A$, preferably $\tau_B << \tau_A$. We treat the background as a single component without significant loss of generality as long as the assumptions about lifetimes apply to all the background components (in which case the representation is of an averaged background).

Further definitions are: the fraction of the FLINT from the analyte is fA. We define the quantities $X_i = M_i \cos(\theta_i)$ and $Y_i = M_i \sin(\theta_i)$, where i can equal A, B, or S. The values of $M_A$, $\theta_A$, $M_B$, and $\theta_B$ are those that would obtain if the A and B components were present separately.

From above, we know that under the restrictions on relative lifetimes imposed above the following two expressions hold to a good approximation:

$$f_A = (1 - X_S)/(1 - X_A) \tag{52}$$

and $$\tan(\theta_A) = Y_S/(X_S - 1 + f_A) \tag{53}$$

Substituting Equation 52 into Equation 53 gives $$\tan(\theta_A) = [Y_S/(1 - X_S)][(1 - X_A)/X_A] \tag{54}$$

Now from elementary trigonometry and Equation 50 we have $$\cos(\theta_A) = (1 + (\omega \tau_A)^2)^{-1/2} \tag{55}$$

and $$M_A = (1 + (\omega \tau_A)^2)^{-1/2} \tag{56}$$

so that $$X_A = (1 + (\omega \tau_A)^2)^{-1} \tag{57}$$

and $$1 - X_A = (\omega \tau_A)^2/(1 + (\omega \tau_A)^2) \tag{58}$$

Substituting Equation 50 for component A along with Equations 57 and 58 into Equation 54 and rearranging to solve for $\tau_A$, we finally have $$\tau_A = (1 - X_S)/Y_S = (1 - M_s \cos(\theta_S))/(M_s \sin(\theta_S)) \tag{59}$$

In other words, we have an expression for the label lifetime $\tau_A$ purely in terms of quantities that can be obtained in a single FD measurement on the system that contains both analyte and background.

Figure 42:
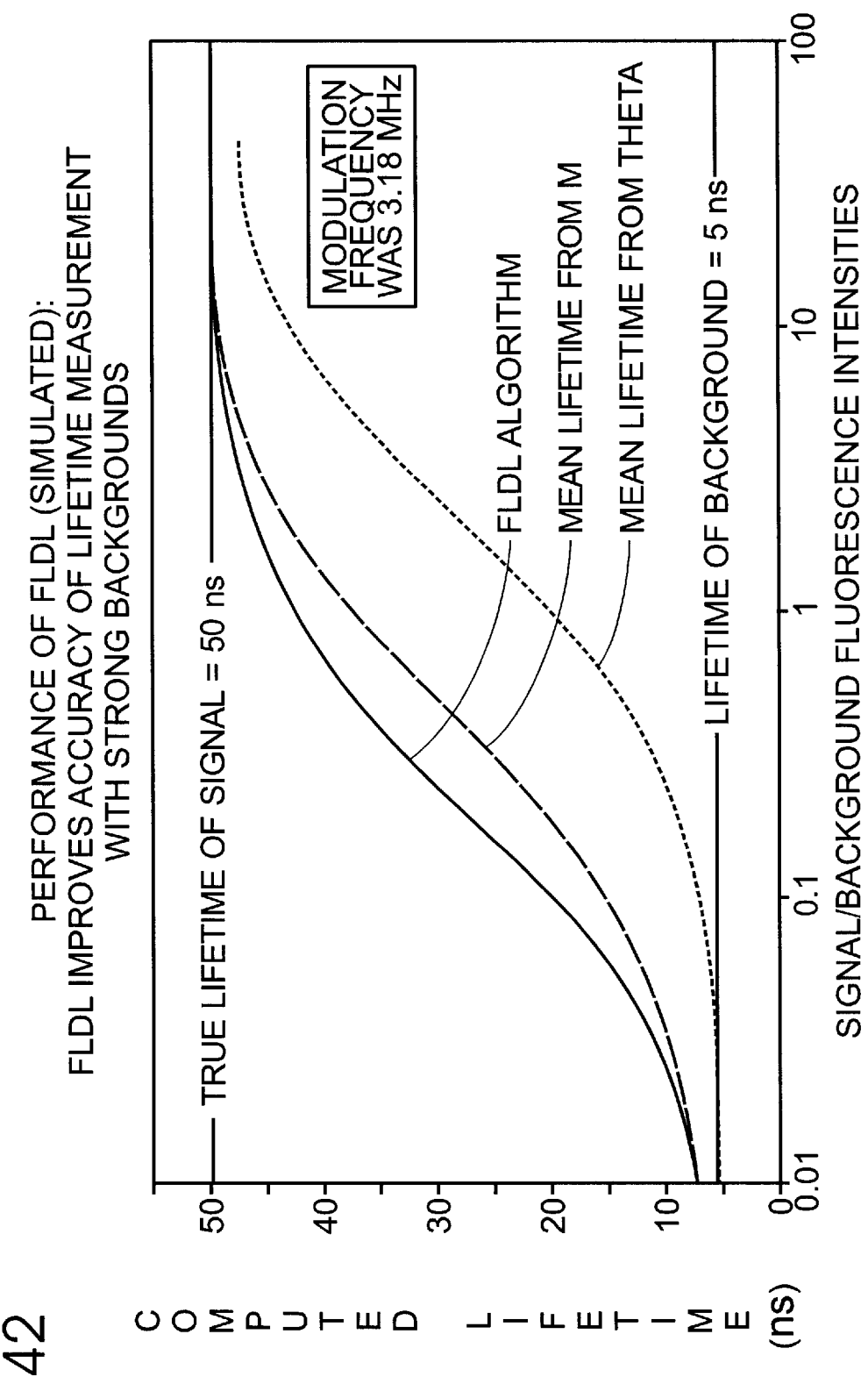
FIG. 42 is a graph of computed lifetime versus signal-to-background fluorescence intensities for simulated parameters, showing how the FLDL method improves the accuracy of lifetime measurement with strong backgrounds.

FIG. 42 shows the performance that can be expected of the algorithm, obtained using a simulation of FD experiments on a two-component system containing analyte (fluorescent label) and a fluorescent background in varying proportions. The FLDL algorithm demonstrates its superiority to the application of Equations 50 or 51 in that the lifetime of the analyte calculated with FLDL is much closer to the true value than the lifetime calculated with Equation (4) or (5) when there is appreciable background fluorescence.

Third-order FLDI (Fluorescence Lifetime Discriminated Intensity) Algorithm for Analyzing FLARe™ Data. The goal of this work is to derive methods to improve the accuracy of fluorescence-intensity and fluorescence-lifetime measurements of compounds of interest (called analytes, or, equivalently, labels) in the presence of unwanted background fluorescence. Among the fields in which these methods can be applied is drug discovery, particularly in high-throughput screening assays.

Our previous FLDI methods were based on measuring fluorescent systems, containing fluorescence both from analyte, A, and background, B. An expression for the fraction $f_A$ of the fluorescence intensity contributed by A was obtained as a series expansion in $\omega \tau_B$, where this product was <1. This expansion contained only even powers of the product. Truncating before the second-order term thus gave an expression that was good to first order in $\omega \tau_B$. A benefit of this method is that there is no need to determine the value of $\tau_B$.

The present invention truncates the expansion before the fourth-order term and thus is good to third order in $\omega \tau_B$. This improves the ability of the method to determine analyte intensity in the presence of background fluorescence. In contrast to previous work, however, $\tau_B$ now appears in the formulas and must be measured explicitly or implicitly.

This can be done by making measurements at two modulation frequencies, $\omega_1$ and $\omega_2$. The series expansion can then be used to generate two equations (on for each frequency) in two unknowns ($f_A$ and $\tau_B$). Elimination of the lifetime yields an equation for $f_A$.

Here are the details. The earlier series expansion can be written in the form:

$$f_A = \alpha(\omega) + \beta(\omega)\tau_B^2 \quad (60)$$

Here $\alpha(\omega)$ and $\beta(\omega)$ are the following expressions, where dependence on $\omega$ is written explicitly:

$$\alpha(\omega) = [1 - X_S(\omega)]/[1 - X_A(\omega)] \quad (61)$$

$$\beta(\omega) = \omega^2 [X_A(\omega) - X_S(\omega)]/[1 - X_A(\omega)]^2 \quad (62)$$

Eliminating $\tau_B^2$ yields the expression:

$$f_A = [\alpha(\omega_1)\beta(\omega_2) - \alpha(\omega_2)\beta(\omega_1)]/[\beta(\omega_2) - \beta(\omega_1)] \quad (63)$$

This form of the equation requires measurement of the analyte fluorescence in the absence of background, which is generally not difficult and, moreover, can be done once and stored for reference and inclusion in the analysis of many samples.

Despite being based on a truncated power series in $\tau_B^2$, this result gives accuracy comparable to that obtained with much more complicated expressions derived from exact equations for the behavior of two-component systems.

E. Reference Compounds

The apparatus, methods, and compositions of matter provided by the invention also can be used to correct for modifications in analyte signal from scattering, absorption, and other modulators, including background, through use of a reference compound. These modifications may affect intensity and polarization, among others.

The compositions of matter provided by the invention may include first and second luminophores having emission spectra that overlap significantly, but luminescence emissions that may be resolved using lifetime-resolved methods. The first and second luminophores may include an analyte and a reference compound. The analyte may be designed to participate in an assay, and the reference compound may be designed to participate in an assay, and the reference compound may be designed to be inert and constant from assay to assay.

The apparatus provided by the invention may include a stage, light source, detector, processor, and first and second optical relay structures. These components are substantially as described above, especially in supporting and inducing an emission from a composition, and in detecting and converting the emission to a signal. The emission may include fluorescence or phosphorescence.

The processor may use information in the signal to determine the intensity of the light emitted by the analyte and the intensity of the light emitted by the reference compound. The analyte and reference compound have luminescence lifetimes that are resolvable by lifetime-resolved methods, so that the intensities of the analyte and reference compound may be determined using lifetime-resolved methods. These methods may include frequency-domain methods, such as those described above for distinguishing analyte and background.

In the presence of a signal modulator, such as scattering or absorption, the apparent intensity $I_c'$ of light detected from a composition will equal the product of a transmission factor T and the true intensity $I_c$ of the light emitted from the composition.

$$I_c' = T \cdot I_c \quad (64)$$

The transmission factor may include contributions from changes in the excitation light and changes in the emission light. The transmission factor typically (but not always) will range from zero to one.

If the composition contains both an analyte and a reference compound, the apparent intensity of the composition will equal the product of the transmission factor and the sum of the true intensity $I_A$ of the analyte and the true intensity $I_R$ of the reference compound.

$$I_c' = T \cdot (I_a + I_r) \quad (65)$$

The apparent intensity $I_a'$ of the analyte will equal the apparent intensity of the composition minus the apparent intensity of the reference compound. Similarly, the apparent intensity $I_r'$ of the reference compound will equal the apparent intensity of the composition minus the apparent intensity of the analyte.

These intensities may be computed using LDI or LRI methods, among others. For example, a typical experiment may include a short-lifetime analyte and a long-lifetime reference compound, although other combinations also may be used. In this case, the apparent intensity of the analyte may be calculated using Equation 22, where the reference compound effectively is treated as long-lifetime background.

$$I_a' = T \cdot I_a = T \cdot (I_c - I_r) = I_c' \cdot \left(1 - \frac{1 - X_c}{1 - X_r}\right) \quad (66)$$

Similarly, the apparent intensity of the reference compound may be calculated using Equation 21, where the analyte effectively is treated as short-lifetime background.

$$I_r' = T \cdot I_r = T \cdot (I_c - I_a) = I_c' \cdot \frac{1 - X_c}{1 - X_r} \quad (67)$$

The processor also uses information in the signal to calculate a quantity that expresses the intensity of the analyte as a function of the intensity of the reference compound. This quantity may be a ratio of the intensity of the analyte to the intensity of the reference compound, among others.

$$\frac{I_a}{I_r} = \frac{I_a'}{I_r'} = \frac{X_c - X_r}{1 - X_c} \quad (68)$$

Such a ratio is independent of the degree of modulation in the sample, and thus will be comparable for every sample in a family of samples, if for example every sample has the same concentration of reference compound.

The processor also is capable of discriminating between the light emitted by the analyte, the light emitted by a reference compound, and a background, if all three have different lifetimes, using the dual-frequency lifetime-resolved methods described above (e.g., Equation 25).

The methods provided by the invention may include various steps, including (1) providing a composition that includes the analyte and a reference compound, (2) illuminating the composition, so that light is emitted by the analyte and reference compound, (3) detecting the light emitted by the analyte and reference compound and converting it to a signal, (4) processing the signal to determine the intensity of the light emitted by the analyte and the intensity of the light emitted by the reference compound, and (5) calculating a quantity that expresses the intensity of the analyte as a function of the intensity of the light emitted by the reference compound. The methods also may include additional or alternative steps. The methods may be practiced using the apparatus described above.

The invention may handle a variety of analytes, reference compounds, and backgrounds. Generally, the excitation and emission spectra of the reference compound should be the same as the excitation and emission spectra of the analyte, so that the intensity of the reference compound will be modulated by the same amount as the intensity of the analyte. (Because the factors that modulate detection of luminescence are generally wavelength dependent, reference compounds having different spectra than the analyte provide only a partial solution, at best.) For optimal resolution, the lifetime of the reference compound should be significantly larger or significantly smaller than the lifetime of the analyte, and the lifetimes of the reference compound and analyte should be greater than the lifetime of the background. Also for optimal resolution, the specific lifetime of the background should be confined to a range. These conditions apply for most assays of commercial interest; for example, in most high-throughput assays, the background from the microplate and assay components is under 10 nanoseconds. These are preferred conditions; because the lifetime-resolved methods described above are so sensitive, the composition actually need include only a small amount of the reference compound (roughly 2% of the total intensity), and the lifetimes of analyte, reference compound, and background can be reasonably similar.

The reference compound may be associated with the composition using a variety of mechanisms. The reference compound may be associated with the composition directly, for example, by dissolving or suspending (e.g., as a micelle) the reference compound in the composition. The reference compound also may be associated with the composition indirectly, for example, by incorporating the reference compound into or onto beads, other carriers, or sample containers associated with the composition.

Associating the reference compound with beads or other carriers has a number of advantages. The carriers may be suspended in the composition or allowed to sink to the bottom of the sample container holding the composition. The carriers also may be attached to the walls or bottom of the sample container, for example, by chemical linkages such as biotin-streptavadin. The carriers also may be rendered magnetic, so that they may be pulled to one part of the sample container (e.g., a side or bottom) to permit the composition to be analyzed with and without the reference compound.

Associating the reference compound with the sample container also has a number of advantages. The reference compound may be layered onto the surface of the sample container, or formed into the plastic or other material used to form the sample container. Such approaches eliminate the need to add the reference compound to the composition, and they may prevent the reference compound from interacting with components of the composition and affecting the associated assay.

Although the invention has been disclosed in its preferred forms, the specific embodiments thereof as disclosed and illustrated herein are not to be considered in a limiting sense, because numerous variations are possible. Applicants regard the subject matter of their invention to include all novel and nonobvious combinations and subcombinations of the various elements, features, functions, and/or properties disclosed herein. No single feature, function, element or property of the disclosed embodiments is essential. The following claims define certain combinations and subcombinations of features, functions, elements, and/or properties that are regarded as novel and nonobvious. Other combinations and subcombinations may be claimed through amendment of the present claims or presentation of new claims in this or a related application. Such claims, whether they are broader, narrower, equal, or different in scope to the original claims, also are regarded as included within the subject matter of applicants' invention.

We claim:

1. A method of detecting a polynucleotide, the method comprising:
   providing a substrate having at least two assay sites;
   locating a different reference polynucleotide at each assay site;
   depositing substantially equal amounts of a sample polynucleotide at each assay site under conditions conducive to hybridization, wherein at least one of the reference and sample polynucleotides at each assay site is labeled with a luminophore;
   illuminating each assay site with polarized light;
   detecting polarized light transmitted from each assay site; and
   deriving information relating to the sequence of the sample polynucleotide by comparing the extent of polarization of the light emitted from each assay site.

2. The method of claim 1, wherein the substrate is a microplate having a plurality of wells, and wherein each assay site is located in a different one of the wells.

3. The method of claim 2, wherein each well has a frusto-conical shape.

4. The method of claim 2, wherein the wells are organized in a density of at least about 4 wells per 81 $mm^2$.

5. The method of claim 2, wherein each well has a maximum volume capacity of less than about 55 microliters.

6. The method of claim 1, wherein the substrate is a chip.

7. The method of claim 1, wherein the reference polynucleotides are bound to the substrate at each assay site.

8. The method of claim 1, wherein the reference polynucleotides are in solution at each assay site.

9. The method of claim 1, wherein the reference polynucleotides are selected from the group consisting of DNA, RNA, and PNA.

10. The method of claim 1, wherein the reference polynucleotides are oligonucleotides.

11. The method of claim 1 further comprising:
   amplifying the sample polynucleotide using the polymerase chain reaction prior to the step of depositing the sample polynucleotide at each assay site.

12. The method of claim 1, wherein the sample polynucleotides are selected from the group consisting of DNA, RNA, and PNA.

13. The method of claim 1, wherein the sample polynucleotides are labeled with the luminophore.

14. The method of claim 1, wherein the reference polynucleotides are labeled with the luminophore.

15. The method of claim 1 further comprising:
   permitting the sample and reference polynucleotides to hybridize prior to the step of illuminating each assay site.

16. The method of claim 1 further comprising:
   forming a complex between the sample polynucleotide, the reference polynucleotide, and a mass label prior to the step of illuminating each assay site.

17. The method of claim 1, wherein the concentration of reference polynucleotide is sufficient relative to the concentration of sample polynucleotide to produce detectable hybridization between the reference and sample polynucleotides.

18. The method of claim 1, the reference polynucleotides being double-stranded, further comprising the step of treating the reference polynucleotides to increase binding by the sample polynucleotides.

19. The method of claim 1, wherein the step of deriving information relating to the sequence includes the step of assaying for single nucleotide polymorphisms.

20. The method of claim 1, wherein the steps of illuminating and detecting are performed on a site-by-site basis.

21. The method of claim 1, wherein the steps of illuminating and detecting are performed on at least two sites simultaneously.

22. The method of claim 1, wherein the extent of polarization is assessed by determining a polarization or an anisotropy.

23. The method of claim 1 further comprising:
converting the light detected from each assay site to a signal; and
discriminating between a first portion of the signal that is attributable to light emitted by the luminophore and a second portion of the signal that is attributable to a background.

24. The method of claim 23, wherein the step of discriminating is performed without requiring a determination of the lifetime or intensity of the background.

25. The method of claim 23, wherein the step of discriminating is performed without requiring use of information obtained from a blank, irrespective of whether a significant amount of the background is being detected by the detector at the same time that light emitted by the analyte is being detected.

26. The method of claim 23, wherein the step of discriminating is performed in the frequency-domain without requiring a determination of the intensity of the background.

27. The method of claim 23, wherein the step of discriminating is performed in the frequency-domain without requiring use of information obtained from a blank.

28. The method of claim 23, wherein the background is attributable to the substrate.

29. A method of detecting a polynucleotide, the method comprising:
contacting a sample polynucleotide with a reference polynucleotide at an assay site, wherein at least one of the reference and sample polynucleotides is labeled with a luminophore;
illuminating the assay site with light capable of stimulating luminescence from the luminophore;
detecting light transmitted from the assay site;
converting the detected light to a signal;
discriminating between a first portion of the signal that is attributable to light emitted by the luminophore and a second portion of the signal that is attributable to a background; and
deriving information relating to the extent of hybridization between the sample polynucleotide and the reference polynucleotide based on the extent of polarization of the light emitted from the hybrid.

30. The method of claim 29, wherein the discriminating step uses lifetime-resolved methods.

31. The method of claim 30, wherein the discriminating step uses frequency-domain methods.

32. The method of claim 29 further comprising:
performing each of the steps at a second assay site, wherein the reference polynucleotide is different at the two sites and the sample polynucleotide is the same at the two sites.

33. The method of claim 32 further comprising:
obtaining information concerning the sequence of the sample by comparing the extent of hybridization between the sample polynucleotide and the reference polynucleotide at each site.

34. The method of claim 29, wherein the discriminating step is performed without using information obtained from a blank.

35. The method of claim 29 further comprising:
combining a luminescent reference compound with the sample polynucleotide and the reference polynucleotide; and
determining the intensity of light emitted from the luminophore as a function of the intensity of light emitted from the reference compound.

36. The method of claim 35, wherein the determining step uses lifetime-resolved methods.

37. The method of claim 35 further comprising:
calculating a ratio of the intensity of light emitted from the luminophore to the intensity of light emitted from the reference compound.

38. A method of detecting hybridization between first and second polynucleotides, the method comprising:
providing a substrate containing at least two assay sites, each assay site being located in a well having a shape;
contacting a first polynucleotide with a second polynucleotide at each assay site, wherein at least one of the two polynucleotides is bound to a luminophore;
directing a light beam to each assay site, wherein the light beam has a shape that substantially matches the shape of the well; and
determining the extent of hybridization between the first polynucleotide and the second polynucleotide based on detecting polarized light emitted from the luminophore at each assay site.

* * * * *